US010140418B2

(12) United States Patent
Van Laar

(10) Patent No.: US 10,140,418 B2
(45) Date of Patent: *Nov. 27, 2018

(54) SYSTEM AND METHOD FOR CLASSIFICATION OF PATIENTS

(71) Applicant: Quest Diagnostics Investments LLC, Secaucus, NJ (US)

(72) Inventor: Ryan L. Van Laar, Brooklyn, NY (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 739 days.

This patent is subject to a terminal disclaimer.

(21) Appl. No.: 14/549,069

(22) Filed: Nov. 20, 2014

(65) Prior Publication Data

US 2015/0154351 A1 Jun. 4, 2015

Related U.S. Application Data

(63) Continuation of application No. 13/498,965, filed as application No. PCT/AU2010/001286 on Sep. 30, 2010, now Pat. No. 8,999,648.

(60) Provisional application No. 61/247,802, filed on Oct. 1, 2009.

(51) Int. Cl.
*G06F 19/20* (2011.01)
*G06F 19/24* (2011.01)

(52) U.S. Cl.
CPC .............. *G06F 19/20* (2013.01); *G06F 19/24* (2013.01)

(58) Field of Classification Search
None
See application file for complete search history.

(56) References Cited

U.S. PATENT DOCUMENTS 8,999,648 B2 * 4/2015 Van Laar ................. G06F 19/20
435/6.12
2004/0058340 A1 3/2004 Dai et al.

FOREIGN PATENT DOCUMENTS

WO  WO 2006/002240 A2  1/2006
WO  WO 2012/040784 A1  4/2012

OTHER PUBLICATIONS

Miller, L., et al., "An expression signature for p53 status in human breast cancer predicts mutation status, transcriptional effects, and patient survival," *Proceedings of the National Academy of Sciences, USA*, vol. 102 No. 38, pp. 13550-13555 (2005).
International Search Report for International Application No. PCT/AU2010/001286, dated Nov. 18, 2010.
Notification Concerning Transmittal of International Preliminary Report on Patentability and Written Opinion of the International Searching Authority for International Application No. PCT/AU2010/001286, dated Apr. 12, 2012.
D'Alfonso, T. M., et al., "BreastPRS is a gene expression assay that stratifies intermediate-risk Oncotype DX patients into high- or low-risk for disease recurrence," *Breast Cancer Research and Treatment*, 139(3): 705-715 (2013).
Desmedt, C., et al., "Strong Time Dependence of the 76-Gene Prognostic Signature for Node-Negative Breast Cancer Patients in the TRANSBIG Multicenter Independent Validation Series," *Clinical Cancer Research*, 13: 3207-3214 (2007).
Ivshina, A. V., et al., "Genetic Reclassification of Histologic Grade Delineates New Clinical Subtypes of Breast Cancer," *Cancer Research*, 66: 10292-10301 (2006).
Jorissen, R. N., et al., "Metastasis-Associated Gene Expression Changes Predict Poor Outcomes in Patients with Dukes Stage B and C Colorectal Cancer," *Clinical Cancer Research*, 15: 7642-7651 (2009).
Pawitan, Y., et al., "Gene expression profiling spares early breast cancer patients from adjuvant therapy: derived and validated in two population-based cohorts," *Breast Cancer Research*, 7: R953-R964 (2005).
Schmidt, M., et al., "The Humoral Immune System Has a Key Prognostic Impact in Node-Negative Breast Cancer," *Cancer Research*, 68: 5405-5413 (2008).
Shedden, K., et al., "Gene Expression-Based Survival Prediction in Lung Adenocarcinoma: A Multi-Site, Blinded Validation Study," *Nature Medicine*, 14: 822-827 (2008).
Van Laar, R. K., "Design and Multiseries Validation of a Web-Based Gene Expression Assay for Predicting Breast Cancer Recurrence and Patient Survival," *The Journal of Molecular Diagnostics*, 13(3): 297-304 (2011).
Zhu, C.-Q, et al., "Prognostic and Predictive Gene Signature for Adjuvant Chemotherapy in Resected Non-Small-Cell Lung Cancer," *Journal of Clinical Oncology*, 28(29): 4417-4424 (2010).
Affymetrix HG-U133A & HG-U133B Probe Sequences, published Aug. 20, 2008 [Retrieved from Internet Oct. 9, 2013]. <URL:http://www.affymetrix.com/Auth/analysis/downloads/data/HG-U133A.probe_fasta.zip> & <URL:http://www.affymetrix.com/Auth/analysis/downloads/data/HG-U133B.probe_fasta.zip>.

(Continued)

*Primary Examiner* — James S Ketter
(74) *Attorney, Agent, or Firm* — Foley & Lardner LLP

(57) ABSTRACT

A system (100) for classifying a biological test sample, including a database (112) populated with reference expression data. The reference expression data includes expression levels of a plurality of molecules (polynucleotides or polypeptides), including a set of marker molecules, in a plurality of reference samples. Each reference sample has a pre-assigned value for each of one or more clinically significant variables. The system includes at least one processor (110) and at least one storage medium containing program instructions for execution by said processor (110). The program instructions cause the processor to accept (122) input expression data including a test vector of expression levels of the marker molecules in the biological test sample; and pass the input expression data to one or more analysis programs (130*a*, 130*b*, 135). The analysis programs include at least one statistical classification program (135) for assigning a value of at least one of said clinically significant variables to the test sample.

15 Claims, 9 Drawing Sheets
(1 of 9 Drawing Sheet(s) Filed in Color)

(56) References Cited

OTHER PUBLICATIONS

International Search Report from International Application No. PCT/AU2011/001250, titled "Gene Marker Sets and Methods for Classification of Cancer Patients," dated Nov. 24, 2011.
International Preliminary Report on Patentability and Written Opinion of the International Searching Authority from International Application No. PCT/AU2011/001250, titled "Gene Marker Sets and Methods for Classification of Cancer Patients," dated Apr. 11, 2013.
Office Action dated Jul. 30, 2013 in U.S. Appl. No. 13/498,965.
Notice of Allowance dated Nov. 27, 2013 in U.S. Appl. No. 13/498,965.
Office Action issued dated May 20, 2014 in U.S. Appl. No. 13/498,965.
Notice of Allowance dated Dec. 9, 2014 in U.S. Appl. No. 13/498,965.

\* cited by examiner

SYSTEM AND METHOD FOR CLASSIFICATION OF PATIENTS

RELATED APPLICATION(S)

This application is a continuation of U.S. application Ser. No. 13/498,965, which is the U.S. National Stage Application of International Application No. PCT/AU2010/001286, filed on Sep. 30, 2010, published in English, which claims the benefit of U.S. Provisional Application No. 61/247,802, filed Oct. 1, 2009.

FIELD OF THE INVENTION

The present invention relates to classification of patients on the basis of expression of multiple biological markers. It is particularly suited to expression data from microarrays and other high-throughput platforms, although it will be appreciated that the invention may have wider applicability.

BACKGROUND TO THE INVENTION

It has long been recognised that diagnosis and treatment of disease on the basis of epidemiologic studies may not be ideal, especially when the disease is a complex one having multiple causative factors and many subtypes with possibly wildly varying outcomes for the patient. This has recently led to an increased emphasis on so-called "personalised medicine", whereby specific characteristics of the individual are taken info account when providing care.

An important development in the move towards personalised care has been the ability to identify molecular markers which are associated with a particular disease state or which are predictive of the individual's response to a particular treatment.

For example, in relation to breast cancer, the estrogen receptor (ER) or HER2/neu (ErbB-2) status of a tumour can be used in determining a patient's suitability for therapies that target these molecules in the tumor cells. These molecular markers are examples of "companion diagnostics" which are used in conjunction with traditional tests such as histological status in order to guide treatment regimes.

In cancer cases where a tumour has metastasized, it is important to determine the tissue of origin of the tumour. The current diagnostic standard in such cases includes imaging, serum tests and immunohistochemistry (IHC) using one or more of a panel of known antibodies of different tumour specificity (Pavlidis et al, Eur J Cancer 39, p 1990 (2003); Burton et al, JAVA 280, p 1245 (1998); Varadhachary et al, Cancer 100, p 1776 (2004)). For approximately 3-5% of all cases, known as Cancer of Unknown Primary (CUP), these conventional approaches do not reach a definitive diagnosis, although some may eventually be solved with further, more extensive investigations (Horlings et al, J Clin Oncol 26, p 4435 (2008); Raab et al, Cancer 104, p 2205 (2005)). The range of tests able to be performed can depend not only on an individual patient's ability to tolerate potentially invasive, costly and time consuming diagnostic procedures, but also on the diagnostic tools at the clinician's disposal, which may vary between hospitals and countries.

To date, most diagnostic protocols are primarily reliant on microscopy, single gene or protein biomarkers (IHC) and imaging techniques such as MRI and PET Scan. Unfortunately, these techniques all have limitations and may not on their own provide adequate information to diagnose widely metastasized tumours, poorly differentiated malignancies, rare subtypes or unusual presentations of common cancers.

It has been hypothesized that the information gained from gene expression profiling can be used as a companion diagnostic to the above protocols, helping to confirm or refine the predicted primary origin in a focused and efficient manner.

Since the advent of various robotic and high throughput genomic technologies, including RT-PCR and microarray, several groups (van Laar et al, Int J Cancer 125, p 1390 (2009); Rosenfeld et al, Nature Biotechnology 26, p 462 (2008); Tothill et al, Cancer Res 65, p 4031 (2005); Bloom at al, Am J Pathol 164, p 9 (2004); Monzon et al, J Clin Oncol 27, p 2503 (2009); Ramaswamy et al, PNAS 98, 15149 (2001)) have investigated the use of gene expression data to predict the primary origin of a metastatic tumor. Prediction accuracies in the literature, range from 78% to 89%.

A number of gene expression based, commercial diagnostic services have arisen since the sequencing of the human genome, offering a range of personalized diagnostic and prognostic assays. These services represent a significant advance in patient access to personalized medicine. However the requirement of shipping fresh or preserved human tissue to an interstate or international reference laboratory has the potential to expose sensitive biological molecules to adverse weather conditions and logistical delays, in some parts of the world it may also be prohibitively expensive to ship human tissue to a reference laboratory in a timely fashion, thus limiting access to this new technology.

Most current commercially available gene-expression based cancer tests use a proprietary "diagnostic" microarray or PCR-based assay (van Laar et al; Rosenfeld et al; Dumur et al, J Mol Diagn 10, p 67 (2008)). Such arrays allow assaying of a small set of genes chosen for a particular purpose and are custom manufactured for that purpose. Because of the limited set of genes that are quantified by these existing assays, the data generated generally cannot be used for multiple diagnostic or prognostic analyses if a different set of genes is required. Furthermore, whatever data is generated, it is generally not accessible to the clinician requesting the test should it be desired to conduct further investigations or compile a custom database of gene expression data for research purposes.

In view of the above deficiencies, it is desirable to provide a more flexible and efficient method and system for diagnosis and prognosis of a patient based on expression of multiple biological markers.

SUMMARY OF THE INVENTION

Accordingly, in a first aspect, the present invention provides a system for classifying a biological test sample, including:

a database populated with reference expression data, the reference expression data including expression levels of a plurality of molecules (polynucleotides or polypeptides) in a plurality of reference samples, the molecules including a set of marker molecules, each reference sample having a pre-assigned value for each of one or more clinically significant variables;

at least one processor; and at least one storage medium containing program instructions for execution by said processor, said program instructions causing said processor to execute the steps of:

accepting input expression data, the input expression data including a test vector of expression levels of the marker molecules in the biological test sample; and passing the input expression data to one or more analysis programs, the analysis programs including at least one statistical classification program which has been trained to distinguish among said pre-assigned values on the basis of that part of the reference data corresponding to expression levels of the marker molecules; and assigning one of said pre-assigned values to the test sample for at least one of said clinically significant variables using the statistical classification program.

By providing a reference data set with known clinical annotation in a single database in combination with the ability to accept input data from a user of the system, it is possible to have a centralised repository of disease classification which can be used to conduct different diagnostic or prognostic analyses (using different classification programs) with different sets of marker molecules. The system thus provides flexibility in that different tests may be conducted using the same reference data and input data without needing to re-assay the biological test sample.

Preferably, one of said analysis programs includes instructions for assessing the quality of the input expression data. The quality of the input expression data may be at least partly assessed according to the distribution across reference samples of one or more statistics derived from the reference data, the statistics including (for example) background intensity, percentage of molecules above detection threshold, ratio of 3' expression level to 5' expression level, slope of RNA degradation curve, normalisation factor, and log (base 10) ratio of mean intensity to mean background intensity.

Providing a quality control module as one of the analysis programs allows the clinician or other user to check that the data, as a whole, fall within acceptable ranges so that low-quality data are not passed to the classifier or classifiers. Use of low-quality data could lead to a diagnosis which is inconsistent with other tests which may have been conducted, such as imaging or immunohistochemistry.

One of the classification programs may be a prediction of patient gender. This serves as a further quality check since, for example, if a female patient is predicted as male (on the basis of comparison to the reference data which are stratified according to gender), the fidelity of the data is cast into doubt.

In one embodiment, one of said analysis programs includes instructions for normalising the distribution of the input expression data to be comparable with the distribution of the reference expression data. This can help to increase the likelihood that differences between the input and reference data are due to real biological differences, and not due to mere statistical artifacts or to differences in the laboratory protocols used in generating the two data sets.

In a particularly preferred embodiment, each analysis program is executed on a different one of said processors. This can vastly improve the speed of the analysis.

In another aspect, the present invention provides a method for classifying a biological test sample, including the steps of:

choosing a set of marker molecules;

providing a database populated with reference expression data, the reference expression data including expression levels of a plurality of molecules in a plurality of reference samples, the plurality of molecules including at least the marker molecules, each reference sample having a pre-assigned value for each of one or more clinically significant variables;

accepting input expression data, the input expression data including a test vector of expression levels of the marker molecules in the biological test sample; and assigning one of said pre-assigned values to the test sample for at least one of said clinically significant variables by passing the test vector to a statistical classification program;

wherein the statistical classification program has been trained to distinguish among said pre-assigned values on the basis of that part of the reference data corresponding to expression levels of the marker molecules.

The database may be in communication with a server computer which is interconnected to at least one client computer by a data network, said server computer being configured to accept the input expression data from the client computer.

Hosting the database on a server and allowing remote upload can improve the speed and efficiency of diagnosis. The clinician, having conducted a biopsy and assayed the sample (either themselves, or via a service laboratory located on site or nearby) to obtain a data file containing the expression levels of the marker molecules, can then simply upload the data file to the server for analysis and receive the test results within a short space of time, possibly within seconds. The server may reside on an internal network to which the clinician has access, or may be located on a wide area network, for example in the form of a Web server. The latter is particularly advantageous as it allows hosting and maintenance of a server accessing a large database of samples in one location, while a clinician located anywhere in the world and having access to relatively modest local resources can upload a data file to obtain a diagnosis based on a comprehensive set of annotated samples, such an analysis otherwise being inaccessible to the clinician.

The or each clinically significant variable may be selected from the group including disease state, disease prognosis, and treatment response. For example, the disease may be cancer, and the clinically significant variables may be organised according to a hierarchy, the levels of which may be selected from the group consisting of anatomical system, tissue type and tumour subtype. In that case, the classification program may include a multi-level classifier which classifies the test sample according to anatomical system, then tissue type, then tumour subtype. This provides a multi-marker, multi-level classification which is analogous to, but independent of, traditional approaches to diagnosis of tumour origin.

The marker molecules may include any combination of 100 or more of the polynucleotides listed in Table 4. We have found that sets of 100 or more of these molecules can provide a classification accuracy of greater than 85% for anatomical system and greater than 75% for tissue type.

In another embodiment, the disease is breast cancer, in which case the clinically significant variable may be risk of recurrence of the disease. The marker molecules in this embodiment may include the polynucleotides listed in Table 5. This is a prognostic, rather than diagnostic, application of the invention.

The invention is further applicable to other contexts in which predictive analysis is desired. For example, if a reference data set including expression levels for cancer patients having undergone one or more of various drug treatments is available, and the patients are annotated according to response to treatment, it would be possible to build and train a classifier to predict response of a patient who had not yet undergone the treatment, based on the expression levels of marker molecules in that patient.

In a particularly preferred embodiment, the reference expression data may be generated using a platform selected from the group including cDNA microarrays, oligonucleotide microarrays, protein microarrays, microRNA (miRNA) arrays, and high-throughput quantitative polymerase chain reaction (qPCR).

Oligonucleotide microarrays are particularly preferred for use in the present invention. If this type of microarray is used, each molecule being assayed is a polynucleotide, which may either be represented by a single probe on the microarray or by multiple probes, each probe having a different nucleotide sequence corresponding to part of the polynucleotide. If multiple probes are present, one of said analysis programs might include instructions for summarising the expression levels of the multiple probes into a single expression level for the polynucleotide.

Oligonucleotide microarrays such as those manufactured by Affymetrix, Inc and marketed under the trademark GeneChip currently represent the vast majority of microarrays in use for gene (and other nucleotide) expression studies. As such, they represent a standardised platform which particularly lends itself to collation of large databases of expression data, for example from cancer patients, in order to provide a basis for diagnostic or prognostic applications such as those provided by the present invention.

Preferably, the input expression data are generated using the same platform as the reference expression data. If the input expression data are generated using a different platform, then the identifiers of the molecules in the input data are matched to the identifiers of the molecules in the reference data prior to performing classification, for example on the basis of sequence similarity, or by any other suitable means such as on the basis of GenBank accession number, Refseq or Unigene ID.

Preferably, the statistical classification program includes an algorithm selected from the group including k-nearest neighbours (kNN), linear discriminant analysis, principal components analysis, nearest centroid classification and support vector machines.

In a further aspect of the present invention, there is provided a method of classifying a biological test sample from a cancer patient, including the step of:

comparing expression levels of a set of marker molecules in the test sample to expression levels of said set of marker molecules in a set of reference samples, each member of the set of reference samples having a known clinical annotation, to assign a clinical annotation to the test sample, wherein the clinical annotation is selected from the group including anatomical system, tissue of origin, tumour subtype and risk of breast cancer recurrence.

In a yet further aspect, the present invention provides a system for classifying a biological test sample from a cancer patient, including:

a database populated with reference data, the reference data including expression levels of a set of marker molecules in a set of reference samples, each member of the set of reference samples having a known clinical annotation;

at least one processor; and at least one storage medium containing program instructions for execution by said processor, said program instructions causing said processor to execute steps including;

accepting input data in the form of expression levels of the set of marker molecules in the test sample; and assigning a clinical annotation to the test sample on the basis of the similarity of the input data to the expression levels of the set of marker molecules in the reference data;

wherein the clinical annotation is selected from the group including anatomical system, tissue of origin, tumour subtype and risk of breast cancer recurrence.

The marker molecules may include any combination of 100 or more of the polynucleotides listed in Table 4, or may include the polynucleotides listed in Table 5.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF PREFERRED EMBODIMENTS

In the following discussion, embodiments of the invention will be described mostly by reference to examples employing Affymetrix GeneChips. However, it will be understood by the skilled person that the methods and systems described herein may be readily adapted for use with other types of oligonucleotide microarray, or other measurement platforms.

The terms "gene", "probe set" and "molecule" are used interchangeably for the purposed of the preferred embodiments described herein, but are not to be taken as limiting on the scope of the invention.

Figure 1:
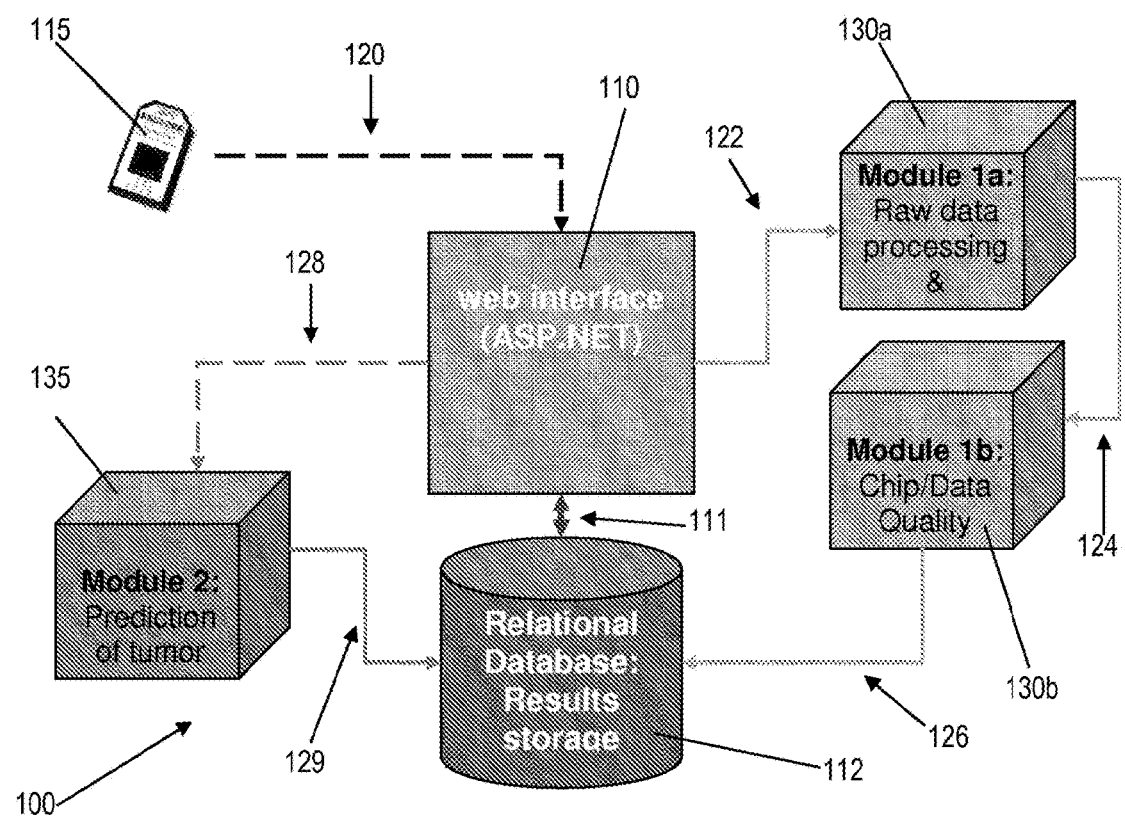
FIG. 1 is a schematic of a system according to one embodiment of the present invention.
Figure 2:
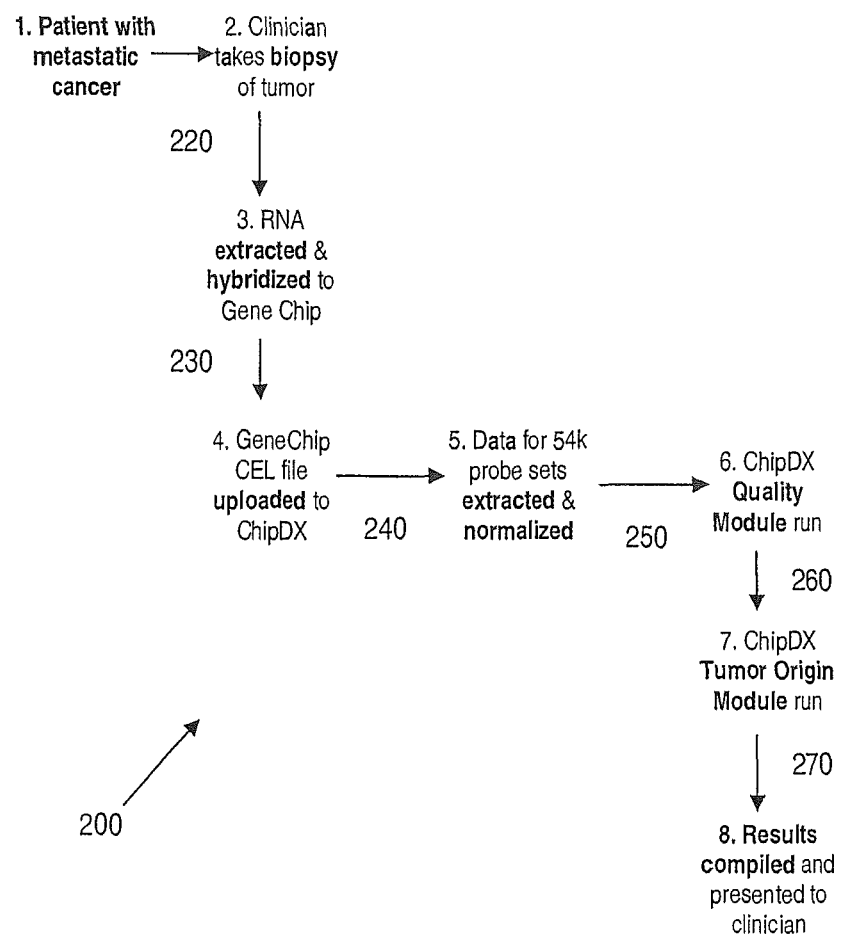
FIG. 2 schematically shows the steps of an exemplary method in accordance with the invention.

Referring to FIGS. 1 and 2, there is shown in schematic form a system 100 and method 200 for classifying a biological test sample. The sample is acquired 220 by a clinician and then treated 230 to extract, fluorescently label and hybridise RNA to microarray 115 according to standard protocols prescribed by the manufacturer of the microarray. Following hybridisation, the surface of the microarray is scanned at high resolution to detect fluorescence from regions of the surface corresponding to different RNA species. In the case of Affymetrix arrays, each scanned "feature" region contains hundreds of thousands of identical oligonucleotides (25 mers), which hybridise to any complementary fluorescently labelled molecules present in the test sample. The fluorescence intensity detected from each feature region is thus correlated with the abundance (expression level) of the complementary sequence in the test sample.

The scanning step results in the production of a raw data file (a CEL file), which contains the intensity values (and other information) for each probe (feature region) on the array. Each probe is one of the 25 mers described above and forms part of one of a multiplicity of "probe sets". Each probe set contains multiple probes. Usually 11 or more for a gene expression microarray. A probe set usually represents a gene or part of a gene. Occasionally, a gene will be represented by more than one probe set.

Once the CEL file is obtained, the user may upload it (step 120 or 240) to server 110.

Accepting Input Data

In the preferred embodiments, the system is implemented using a network including at least one server computer 110, for example a Web server, and at least one client computer. Software running on the Web server can be used to accept the input data file (CEL file) containing the multiple molecule abundance measurements (probe signals) for a particular patient from the client computer over a network connection. This information is stored in the system user's dedicated directory on a file server, with upload filenames, date/time and other details stored in a relational database 112 to allow for later retrieval.

The Web server 110 subsequently allows the user to select individual CEL files for analysis by a list of available diagnostic and prognostic methods, the list being able to be configured to add new methods as they are implemented. Results from the specific analysis requested, in the format of text, numbers and images, are also stored in the relational database 112 and delivered to the user via the Web server 110. All data generated by a particular user is linked to a unique identifier and can be retrieved by the user by logging into to the Web server 110 using a username and password combination.

When an analysis is requested by the user, at step 122, the raw data from the CEL file are passed to a processor, which executes a program 130a contained on a storage medium, which is in communication with the processor.

Accepting Clinical Data Input

In conjunction with the file that contains the multiple molecule abundance measurements (probe signals) for a particular patient, the user can also be asked to input other information about the patient. This information can be used for predictive, prognostic, diagnostic or other data analytical purposes, independently or in association with the molecular data. These variables can include patient age, gender, tumor grade, estrogen receptor status, Her-2 status, or other clinicopathological assessments. An electronic form can be used to collect this information, which the user can submit to a secure relational database.

Algorithms that combine traditional clinical variables or patient demographic data and molecular data can result in more statistically significant results than algorithms that use only one or the other. The ability to collect and analyse all three types of data is a particularly advantageous aspect of at least some embodiments of the invention.

Low Level Analysis

Program 130a is a low-level analysis module, which carries out steps of background correction, normalisation and probe set summarisation (grouped as step 250 in FIG. 2).

Background adjustment is desirable because the probe signals (fluorescence intensities) include signal from non-biological sources, such as optical and electronic noise, and non-specific binding to sequences which are not exactly complementary to the sequence of the probe. A number of background adjustment methods are known in the art. For example, Affymetrix arrays contain so-called 'MM' (mismatch) probes which are located adjacent to 'PM' (perfect match) probes on the array. The sequence of the MM probe is identical to that of the PM probe, except for the $13^{th}$ base in its sequence, and accordingly the MM probes are designed to measure non-specific binding. A number of known methods use functions of PM-MM or $\log_2(PM)$-$\log_2(MM)$ to derive a background-adjusted probe signal, for example the ideal Mismatch (IM) method used by the Affymetrix MAS 5.0 software (Affymetrix, "Statistical Algorithms Description Document" (2002), Santa Clara, Calif., incorporated herein in its entirety by reference). Other methods ignore MM, for example the model-based adjustment of Irizarry et al (Biostatistics 4, p 249 (2003)), or use sequence-based models of non-specific binding to calculate an adjusted probe signal (Wu et al, JASA 99, p 909 (2004)).

Normalisation is generally required in order to remove systematic biases across arrays due to non-biological variation. Methods known in the art include scaling normalisation, in which the mean or median log probe signal is calculated for a set of arrays, and the probe signals on each array adjusted so that they all have the same mean or median; housekeeping gene normalisation, in which the probe or probe set signals for a standard set of genes (known to vary little in the biological system of interest) in the test sample are compared to the probe signals of that same set of genes in the reference samples, and adjusted accordingly; and quantile normalisation, in which the probe signals are adjusted so that they have the same empirical distribution in the test sample as in the reference samples (Bolstad et al, Bioinformatics 19, p 185 (2003)).

If the arrays contain multiple probes per probe set, then these can be summarised by program 130a in any one of a number of ways to obtain a probe set, expression level, for example by calculating the Tukey biweight of the log (PM-IM) values for the probes in each probe set (Affymetrix, "Statistical Algorithms Description Document" (2002)).

Quality Control

Once the low-level analysis is completed, the background-corrected, normalised and, if necessary, summarised, data are passed (step 124) to program 130b, which is a quality control (QC) module. The execution of program 130b is depicted as step 260 in FIG. 2.

Quality data from an individual array can be used to infer the reliability and reproducibility of the entire molecular/genomic profile. One way to do this is to establish ranges for each quality metric that correspond to acceptable, warning and unacceptable levels. By analysing a large number of genomic profiles from reference samples comprising disparate tissue types and laboratory locations, a large body of quality data can be accumulated and stored in database 112.

Figure 4:
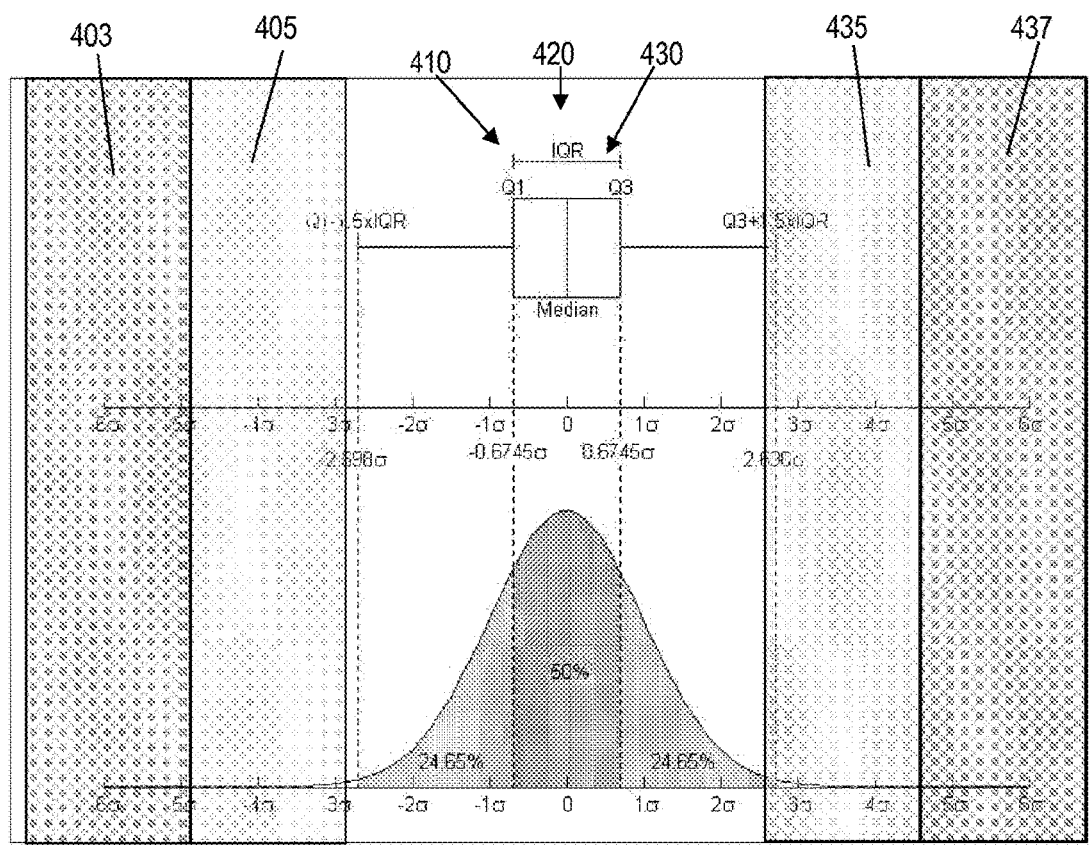
FIG. 4 illustrates selection of ranges for a quality control module for use with some embodiments of the present system and method.

The data for each of the quality metrics used herein approximately follow a log-normal distribution, as illustrated schematically in FIG. 4. Acceptable, warning and unacceptable ranges for each metric are thus calculated by determining the $25^{th}$ percentile (Q1, indicated by 410), $75^{th}$ percentile (Q3, indicated by 430) and corresponding interquartile range (IQR, indicated by 420) of the log-transformed values. Acceptable values are defined as those which lie between Q1−1.5*IQR and Q3+1.5*IQR.

Values in the ranges 405, 435 corresponding to ranges (Q1−1.5*IQR) to (Q1−3.0*IQR) or (Q3+1.5*IQR) to (Q3+3.0*IQR) are referred to as outliers, and are given a warning label. Values which lie to the left 403 or right 437, respectively, of those ranges are referred to as "far outliers" and are deemed to be unacceptably outside of the range of values used to develop and validate the gene expression test for which the test sample is being submitted.

The median, Q1/Q3 and IQR rather than mean and standard deviation are used to determine thresholds as the former are robust to outliers. This prevents the ranges from being overly influenced by a small number of samples that may not be representative of the true general distribution.

Table 1 is an example output from program 130b which describes each quality measurement (Q1 to Q8) and shows the value determined from the specific array being investigated. It also identifies the acceptable range and a variable classifier (Ok/Warning/Reject) column, which may change colour based on the contents of each cell. This allows the end user to rapidly determine if their input data is suitable for further analysis.

TABLE 1 example QC output

| Assessment | Example Result | Acceptable range | Within range? |
|---|---|---|---|
| QC1. Percentage of total gene set detected | 41.50 | 28% to 62% | OK |
| QC2. Background intensity (Average, Log 10) | 2.7 | 1.2 to 2.2 | REJECT |
| QC3. Normalization factor (MAS5, log10) | −0.06 | −0.99 to 1.3 | OK |
| QC4. Ratio of GAPDH 3':5' probes | 1.01 | 0.9 to 1.5 | OK |
| QC5. Ratio of B-actin 3':5' probes | 1.7 | 0.7 to 1.6 | WARNING |
| QC6. RNA degradation analysis | 1.98 | −0.4 to 8.3 | OK |
| QC7. Housekeeping genes normalization factor | −0.45 | −1.1 to 0.9 | OK |
| QC8. Signal to noise ratio (log10) | 1.66 | 1.0 to 2.1 | OK |

Predictive Analysis

If a test sample passes the QC checks of program 130b it can then proceed (step 270) to predictive analysis as carried out by statistical classification program 135, which is used to assign a value of a clinically relevant variable to the sample. Such clinical parameters could include:

The primary tissue of origin for a biopsy of metastatic cancer;

The molecular similarity to patients who do or do not experience disease relapse with a defined time period after their initial treatment;

The molecular similarity to patients who respond poor or well to a particular type of therapeutic agent;

The status of clinicopathological markers used in disease diagnosis and patient management, including ER, PR, Her2, angiogenesis markers (VEGF, Notch), Ki67 etc.;

Possible chromosomal aberrations, including deletions and amplifications of part or whole of a chromosome;

The molecular similarity to patients who respond poor or well to a particular type of radiotherapy;

Other methods that may be developed by a party developers and implemented in the system via an Application Programming Interface (API).

The predictive algorithms used in at least some embodiments of the present invention function by comparing the data from the test sample, to the series of reference samples for which the variable of interest is confidently known, usually having been determined by other more traditional means. The series of known, reference samples can be used as individual entities, or grouped in some way to reduce noise and simplify the classification process.

Figure 5:
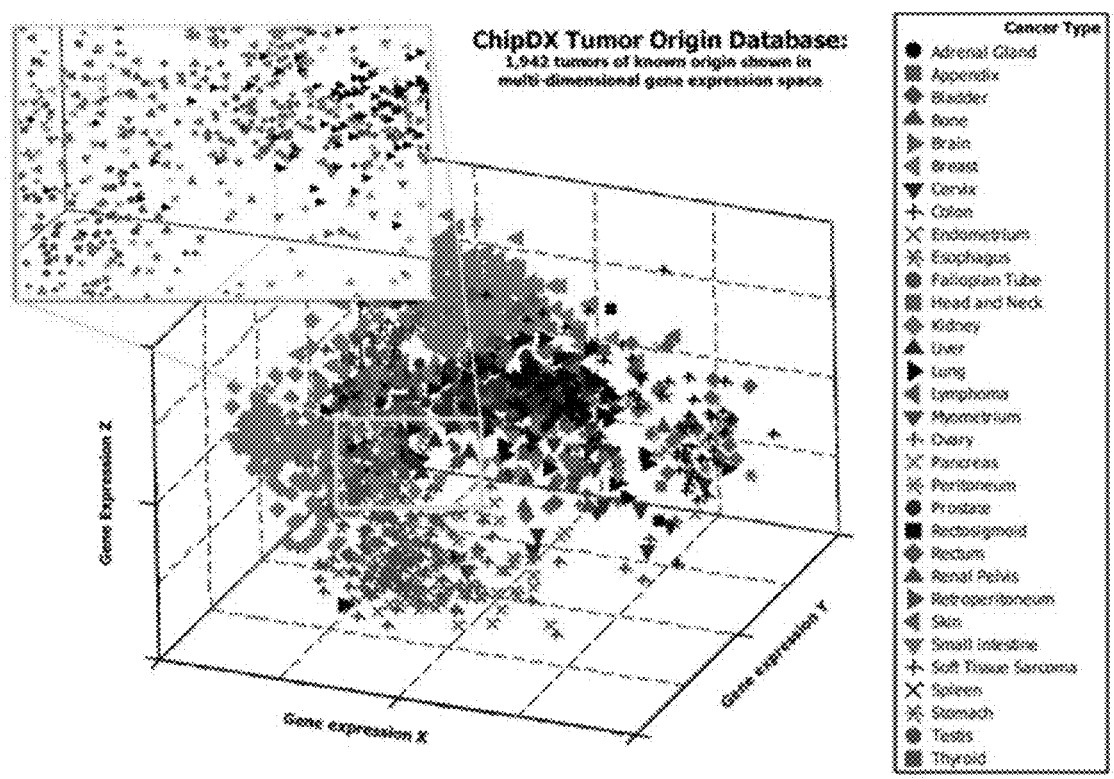
FIG. 5 shows the position of samples belonging to a reference data set in multi-dimensional expression data space.

Algorithms such as the K-nearest neighbor (KNN) algorithm use each reference sample of known type as separate entities. The selected genes/molecules (probe sets) are used to project the known samples into multi-dimensional gene/molecule space as shown in FIG. 5, in which the first three principal components for each sample are plotted. The number of dimensions is equal to the number of genes. The test sample is then inserted into this space and the nearest K reference samples are determined, using one of a range of distance metrics, for example the Euclidean or Mahalanobis distance between the points in the multi-dimensional space. Evaluating the classes of the nearest K reference samples to the test sample and determining the weighted or non-weighted majority class present can then be used to infer the class of the test sample.

The variation of classes present in the K nearest neighbors can also be used as a confidence score. For example, if 4 out of 5 of the nearest neighbor samples to a given test sample were of the same class (eg Ovarian cancer) the predicted class of the test sample would be Ovarian cancer, with a confidence score of 4/5=80%.

Other methods of prediction rely on creating a template or summarized version of the data generated from the reference samples of known class. One way this can be done is by taking the average of each selected gene across clinically distinct groups of samples (for example, those individuals treated with a particular drug who experience a positive response compared to those with the same disease/treatment who experience a negative or no response). Once this template has been determined, the class of a test sample can be inferred by calculating a similarity score to one or both templates. The similarity score can be a correlation coefficient.

Classifiers such as the nearest centroid classifier (NCC), linear discriminant analysis (LDA) or support vector machines operate on this basis (SVM). LDA and SVM carry out weighting of the genes/molecules when creating the classification template, which can reduce the impact of outlier measurements and spread the classification workload evenly over all genes/molecules selected, rather than relying on a subset to contribute to a majority of the total index score calculated. This can be the case when using a simple correlation coefficient as a predictive index.

Preparation of Reference Data Set

To make clinically useful predictions about a specimen of biological material that has been collected from an individual patient, a large database of reference data from patients with the same condition is desirable. The reference samples are preferably processed using similar, more preferably identical, laboratory processes and the reference data are ideally generated using the same type of measurement platform, for example, an oligonucleotide microarray, to avoid the need to match gene identifiers across different platforms.

The reference data can be generated from tissue specifically collected or obtained for the diagnostic test being created, or from publically available sources, such as the NCBI Gene Expression Omnibus (GEO: http://www.ncbi.nlm.nih.gov/geo/). Clinical details about each patient can be used to determine whether the finished database accurately reflects the targeted patient population, for example with regard to age/sex/ethnicity and other relevant parameters specific to the disease of interest.

Clinical annotations can be used for analysis of the same input data at different levels. For example, cancer can be classified using a hierarchy of annotations. These begin at the system level, and then progress to unique tissues and subtypes, which are defined on the basis of pathological or molecular characteristics. The NCI Thesaurus is a source of, hierarchical cancer classification information (http://nciterms.nci.nih.gov/NCIBrowser/Dictionary.do).

All data generated or obtained can be stored in organized flat files or in relational database format, such as Microsoft Access or Microsoft SQL Server. In this format it can be readily accessed and processed by analytical algorithms trained to use all or part of the data to predict the status of a clinically relevant parameter for a given test sample.

Presentation of Results to User

Following execution of classification program 135, the clinical predictions are stored in relational database 112. An interface 111 from the server 110 to database 112 can be used to deliver online and offline results to the end user. Online results can be delivered in HTML or other dynamic file format, whereas portable document format (PDF) can be used for creating permanent files that can be downloaded from the interface 111 and stored indefinitely. Result information in the form of text, HTML or PDF can also be delivered to the user by electronic mail.

AJAX Web 2.0 technologies can be used to streamline the presentation of online results and general functionality of the Web site.

Parallel Processing of Data

A single processor may be used to execute each ot the programs 130a, 130b, 135 and any other analysis desired, However, it is advantageous to configure the system 100 such that each analysis module is managed by a separate processor. This allows parallel execution of different user requests to be performed simultaneously, with the results stored in a single centralized relational database 112 and structured file system.

Figure 3:
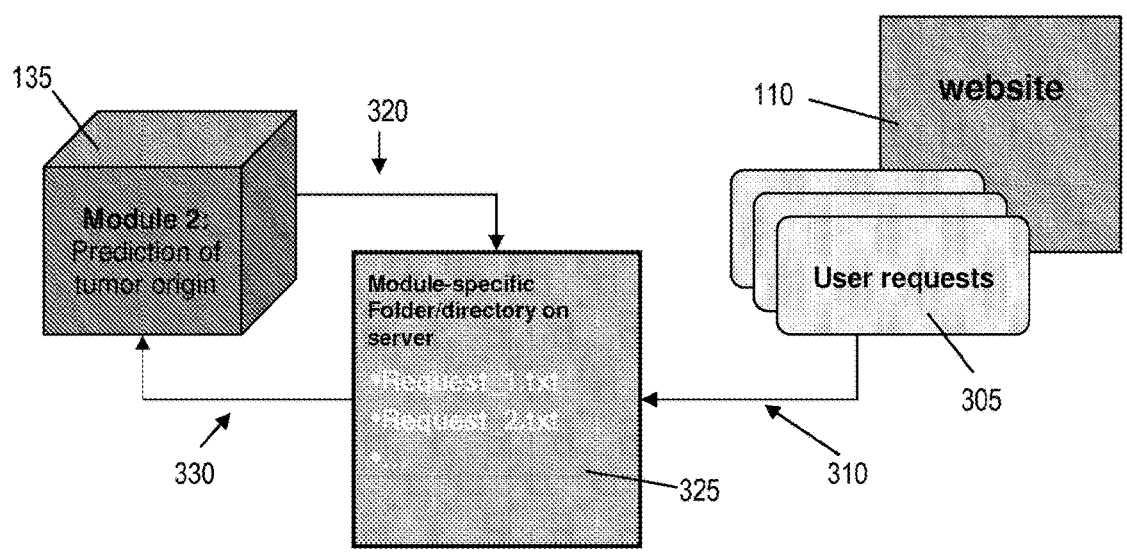
FIG. 3 shows a schematic of another embodiment in which user requests are processed in parallel.

In this embodiment, illustrated schematically in FIG. 3, each module is programmed to monitor 320 a specific network directory ("trigger directory"). When the system operator requests 305 an analysis, either by uploading a new data file or requesting an additional analysis on a previously uploaded data file, the Web server 110 creates a "trigger file" in the directory 325 being monitored by the processing application. This trigger file contains the operator's unique identifier and the unique name of the data file on which to carry out the analysis.

When the classification module 135 detects (step 330) one or more trigger files, the contents of the file are read and stored temporarily in memory. The processing application then performs its preconfigured analysis routine, using the data file corresponding to the information contained in the trigger file. The data file is retrieved from the user's data directory (residing on a storage medium in communication with the server or other network-accessible computer) and read into memory in order to perform the requested calculations and other functions. Once the analysis routine is complete, the trigger file is deleted and the module 135 returns to monitoring its trigger directory for the next trigger file.

Multiple versions of the same classification module 135 can run simultaneously on different processors, all configured to monitor the same trigger directory and write or save their output to the same relational database 112 and file storage system. Alternatively, different modules in addition to classification module 135 could be run on different processors at the same time using the same input data. For processes that take several minutes (eg initial chip processing and Quality Module 130a) this enables analysis requests 305 that are submitted, while an existing request is underway, to be commenced before the completion of the first.

Addition of Further Analysis Modules

It will be appreciated that many other types of analysis (diagnostic, predictive, prognostic or other) may be conducted within the framework of the system provided by the present invention. When a new analysis program is created, it can be added to the list of analysis modules selectable by a user for execution on one or more input data files.

Additional modules can be added to the system by creating additional 'trigger' directories, monitored by analysis scripts. These can, of course, be used in conjunction with existing modules, such as the quality module described above.

A molecular profile can be adapted for use with the system by providing

Details of the technology used to measure the status of the molecules necessary to perform the test (e.g. genes, proteins, antibodies);

A list of molecular identifiers (probe or probe set identifiers, or gene or protein databank accession numbers, for example) specific to the platform used to develop, and to be used for future application of, the test;

A reference set of data from patients with the target disease (or other clinical identification) derived from the same class of patients; and A statistical equation which describes how data corresponding to the molecular identifiers and reference dataset are used to predict the status of a test sample.

A custom results interface can then be created and incorporated into the system, linked to the underlying databases and results delivery mechanisms described previously. Technology-specific quality control measurements can also be incorporated, if they are not adequately represented by those contained in the quality, module described previously.

Example 1

Preparation of Reference Data

The expO data, NCBI GEO accession number GSE2109, generated by the International Genomics Consortium, was used as a reference data set to train a tumor origin classifier.

Figure 6:
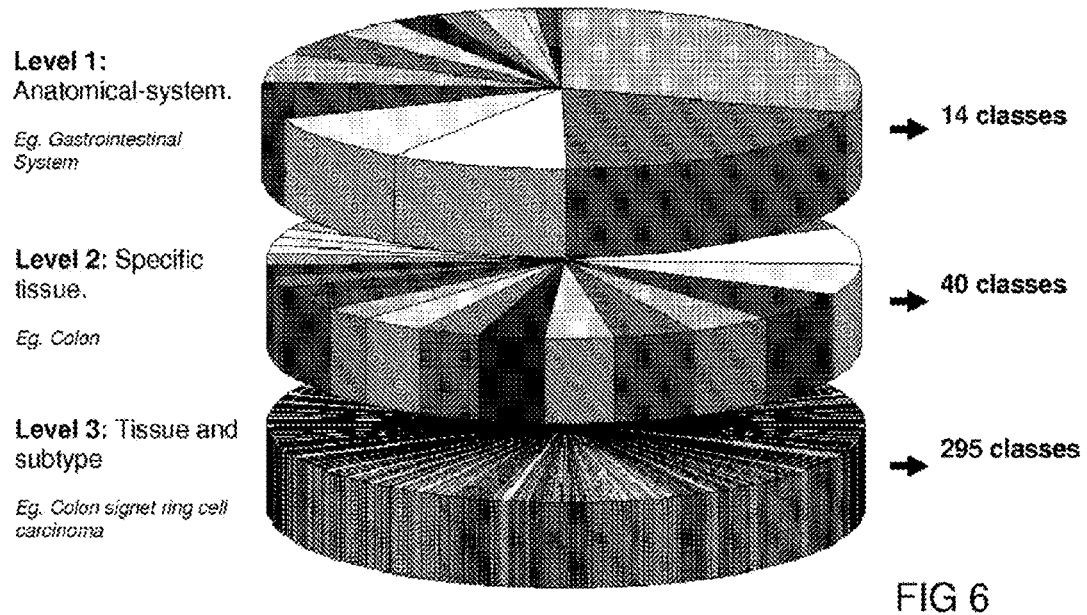
FIG. 6 summarises clinical annotations of reference samples in a reference data set used in one of the Examples.

Downloaded CEL files corresponding to the reference samples were pre-processed with the algorithms from Affymetrix MAS 5.0 software and compiled into BRB ArrayTools format, with housekeeping gene normalization applied. Using the associated clinical information from GSE2109, samples were classified at 3 levels of clinical annotation; (1) anatomical system (n=13), (2) tissue (n=29) and (3) subtype (n=295), as shown in FIG. 6. For Level 1 and 2 annotations, a minimum class size of three was set. The mean class sizes for the three levels of sample annotation were: (1) 149; (2) 66 and (3) 6, correlating with number of neighbors used in the kNN algorithm ($r^2$=0.99).

Data Analysis and Web Service Construction

Predictive gene expression models were developed using BRB ArrayTools and translated to automated scripts in the R statistical language, incorporating functions from the Bioconductor project (Gentleman et al, Genome Biology 5, R80 (2004)). The Web service was constructed in the Microsoft ASP.net language (Redmond, USA; version 3.5) with supporting relational databases developed in Microsoft SQL Server 2008. Statistical analysis of internal cross validation and independent validation series results was performed using Minitab (Minitab Inc. State College Pa., version 15.1.3) and MedCalc (MedCalc Software, Mariakerke, Belgium).

Selecting a Reference Array for Housekeeping Gene Based Normalization

Most cells in the human body express under most circumstances, at comparatively constant levels, a set of genes referred to as "housekeeping genes" for their role in maintaining structural integrity and core cellular processes such as energy metabolism. The Affymetrix U133 Plus 2.0 GeneChip (NCBI GEO accession number GPL 570) contains 100 probe sets that correspond to known housekeeping genes, which can be used for data normalization and quality control purposes. For normalization purposes, the 100 housekeeping genes present on a given array within the reference data set were compared to those of a specific normalization array. To select a normalization array for this test, BRB-ArrayTools was used to identify the "median" array from the entire reference data set. The algorithm used was as follows:

Let N be the number of arrays, and let i be an index of arrays running from 1 to N.
For each array i, compute the median log-intensity of the array (denoted $M_i$).
Select a median M from the $[M_1, \ldots, M_N]$ values. If N is even, then the median M is the lower of the two middle values.
Choose as the median array the one for which the median log-intensity $M_i$ equals the overall median M.

Housekeeping gene normalization was applied to each array in the reference data set. The differences between the $log_2$ expression levels for housekeeping genes in the array and $log_2$ expression levels for housekeeping genes in the normalization array were computed. The median of these differences was then subtracted from the $log_2$ expression levels of all 54,000 probe sets, resulting in a normalized whole genome gene expression profile.

Selection of Marker Probe Sets for Tumor-Type Discrimination

To select probe sets for the prediction of tumor origin, 'one-v-all' comparisons (t-tests) were performed for each tissue type in the training set (n=29) to identify probe sets which were differentially expressed in each tissue type compared to the rest of the data set. The probe sets identified by this procedure provide a characteristic gene expression signature for tumours originating in each tissue type.

In each comparison, genes that had a p-value less than 0.01 for differential expression, and a minimum fold change of 1.5 in either direction (upregulated or downregulated) were identified as marker probe sets. The analysis was performed using BRB ArrayTools (National Institute of Health, US). The 29 sets of marker probe sets were combined into a single list of 2221 unique probe sets, which are listed in Table 4.

The normalized expression data corresponding to these marker probe sets was retrieved from the complete 1942 reference sample×54000 probe set reference data, and this subset was passed to a kNN algorithm at both Level 1 (Anatomical-system, 5NN (nearest neighbours) used) and Level 2 (Tissue, 3NN used) clinical annotation.

Figure 7:
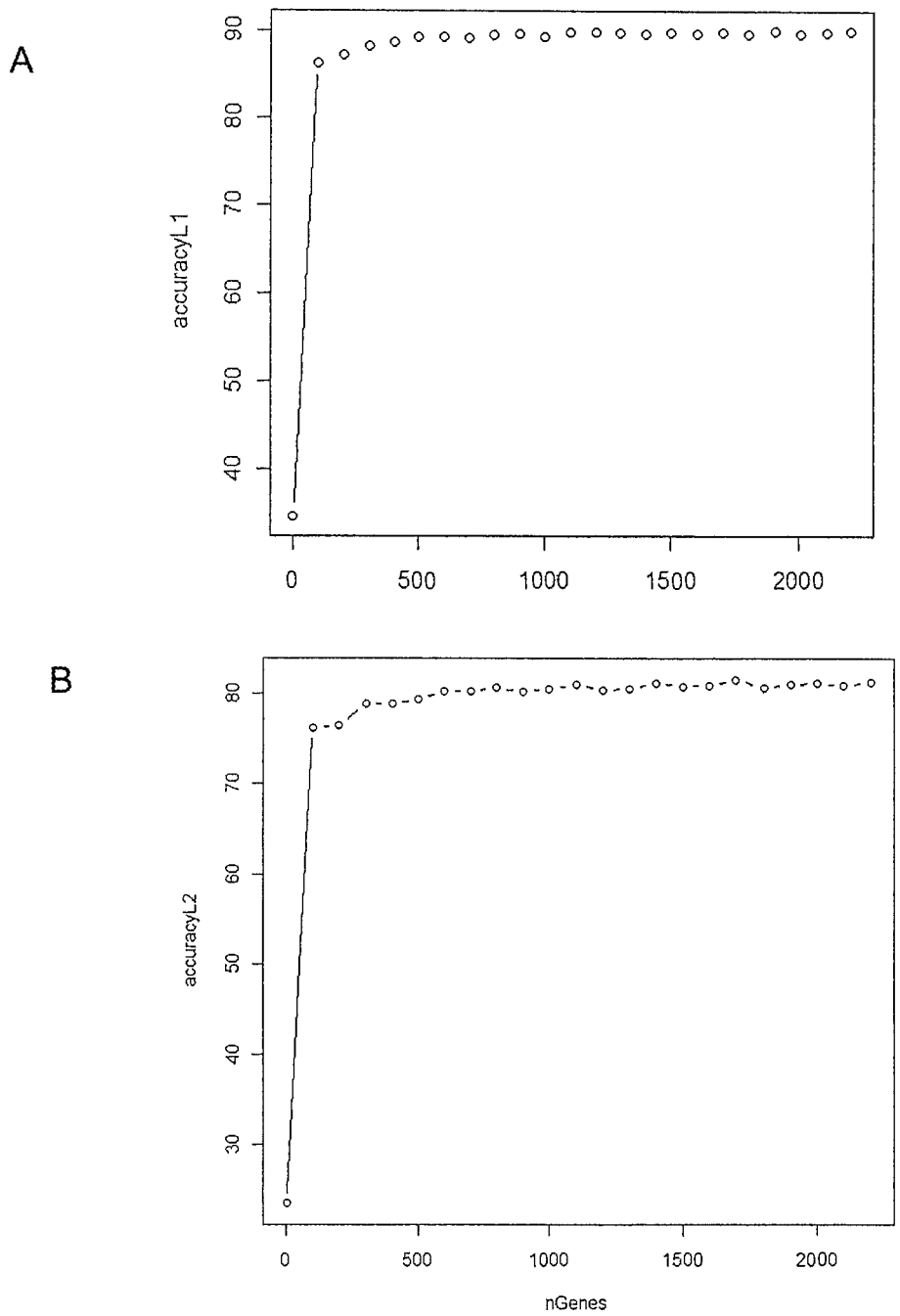
FIGS. 7(a) and 7(b) show the classification accuracy for a multi-level classifier as used in one of the Examples.

To evaluate whether a smaller set of probe sets would achieve lower misclassification rates, leave-one-out cross validation (LOOCV) of the level 1 and 2 classifiers was performed using multiples of 100 probe sets from 10 to 2220, after ranking in descending order of variance. For each cross-validation test, the percentage agreement between the true and predicted classes was recorded and this is shown in FIGS. 7(a) and 7(b). The maximum classification accuracy obtained was 90% for Level 1 and 82% for Level 2. Reducing the number of marker probe sets used did not significantly improve computation speed.

Validation Datasets for Prediction of Tumor Origin

CEL files from 22 independent Affymetrix datasets (all Affymetrix U133 Plus 2.0) containing a total of 1,710 reference samples were downloaded from NOBI GEO and processed as previously described. These datasets represent a broad range of primary and metastatic cancer types, contributing institutes and geographic locations, as detailed in Table 2.

Of 1,461 primary tumor validation samples that passed all QC checks, the Level 1 and Level 2 classifiers predicted 92% and 82% correctly. Tumor subtype data were not available for most validation datasets; therefore percentage accuracy of this level (3) of the classifier was not calculated. The difference observed between Level 1 and Level 2 classifier accuracy is largely influenced by ovary/endometriod and colon/gastric misclassifications. As with all comparisons of novel diagnostic methods with clinically derived results, the percentage agreement is dependent on multiple factors, including the accuracy of the clinical annotation, integrity of the sample annotations and data files as well as the performance characteristics of the method itself.

General linear model analysis was performed on the proportion of correct level 1 and level 2 predictions, including tissue type (n=10) and geographic location (n=3) in a regression equation to determine if these variables were factors in overall result accuracy. For Level 1 predictions (anatomical system), no significant difference in result accuracy was observed for tissue type (P=0.13) or geographic location (P=0.86). For Level 2 predictions (tissue type), a marginally significant difference was observed with tissue type (P=0.049) but no significant difference associated with location (P=0.38). The significant difference associated with tissue type at Level 2 is most likely associated with the small sample size of some tumor types.

TABLE 2

Independent primary tumor datasets used for validation of the tumor origin classifier. Percent agreement with the original (clinically-determined) diagnosis shown. Agreement of the Level 2 classifier increases to 90% if colon/rectum misclassifications are considered as correct.

| Cancer Type | Origin | NCBI GEO Dataset ID | samples | % samples passing all QC checks | Level 1 classifier % agreement with clinical diagnosis | Level 2 classifier % agreement with clinical diagnosis |
| --- | --- | --- | --- | --- | --- | --- |
| Breast | Boston, MA, USA | GSE5460 | 125 | 95% | 100% | 99% |
| Breast | San Diego, CA, USA | GSE7307 | 5 | 100% | 100% | 100% |
| Colon | Singapore | GSE4107 | 22 | 91% | 100% | 90% |

TABLE 2-continued

Independent primary tumor datasets used for validation of the tumor origin classifier. Percent agreement with the original (clinically-determined) diagnosis shown. Agreement of the Level 2 classifier increases to 90% if colon/rectum misclassifications are considered as correct.

| Cancer Type | Origin | NCBI GEO Dataset ID | samples | % samples passing all QC checks | Level 1 classifier % agreement with clinical diagnosis | Level 2 classifier % agreement with clinical diagnosis |
|---|---|---|---|---|---|---|
| Colon | Zurich, Switzerland | GSE8671 | 64 | 100% | 100% | 69% |
| Gastric | Singapore | GSE15460 | 236 | 96% | 89% | 44% |
| Gastric | Singapore | GSE15459 | 200 | 95% | 96% | 54% |
| Liver | Taipei, Taiwan | GSE6222 | 13 | 85% | 91% | 91% |
| Liver | Cambridge, MA, USA | GSE9829 | 91 | 82% | 99% | 99% |
| Lung | St Louis, MO, USA | GSE12667 | 75 | 99% | 89% | 88% |
| Lung | Villejuif, France | GSE10445 | 72 | 57% | 93% | 95% |
| Melanoma | Tampa, FL, USA | GSE7553 | 40 | 100% | 68% | 65% |
| Melanoma | Durham, NC, USA | GSE10282 | 43 | 100% | 65% | 84% |
| Ovarian | Melbourne, Australia | GSE9891 | 285 | 100% | 99% | 96% |
| Ovarian | Ontario, Canada | GSE10971 | 37 | 97% | 100% | 72% |
| Prostate | Ann Arbor, MI, USA | GSE3325 | 19 | 95% | 89% | 89% |
| Prostate | San Diego, CA, USA | GSE7307 | 10 | 100% | 90% | 90% |
| Soft tissue | Paris, France | M-EXP-964* | 16 | 100% | 75% | 75% |
| Soft tissue | New York, NY, USA | GSE12195 | 83 | 99% | 98% | 98% |
| Thyroid | Columbus, OH, USA | GSE6004 | 18 | 67% | 100% | 100% |
| Thyroid | Valhalla, NY, USA | GSE3678 | 14 | 93% | 92% | 100% |
| | | | Total: 1468 | Mean: 92% | Mean: 92% | Mean: 85% |

*Dataset obtained from EBI ArrayExpress (http://www.ebi.ac.uk/microarray-as/ae/)

Creating an Automated Microarray Quality Control System

The total set of 2,775 U133 Plus 2.0 arrays used in the training and validation stages of this analysis was used to derive acceptable ranges, as discussed above, for 8 different QC parameters. The ranges are shown in Table 3.

TABLE 3

Quality module components and acceptable ranges, determined by analysis of all training and validation samples. Lower range = Q1 − 3*IQR, Upper range = Q3 + 3*IQR

| Number | Quality assessment | Acceptable range |
|---|---|---|
| 1 | Percentage of total gene set detected | 28% to 62% |
| 2 | Background intensity (Average across chip; Log 10) | 1.2 to 2.2 |
| 3 | Normalization factor (MAS5, log10) | −0.99 to 1.3 |
| 4 | Ratio of GAPDH 3':5' probes | 0.9 to 1.5 |
| 5 | Ratio of B-actin 3';5' probes | 0.7 to 1.6 |
| 6 | RNA degradation analysis (slope of regression line) | −0.4 to 8.3 |
| 7 | Housekeeping genes normalization factor | −1.1 to 0.9 |
| 8 | Signal to noise ratio (log10) - mean probe intensity/mean background intensity | 1.0 to 2.1 |

The Bioconductor package 'SimpleAffy' (Wilson and Miller, Bioinformatics 21, p 3683 (2006)) was used to generate measurements of background intensity, percentage of probe sets detected and 3'/5' ratios. RNA degradation slopes were computed using the 'AffyRNAdeg' function in the 'affy' package (Gautier et al, Bioinformatics 20, p 307 (2004)).

The quality module also includes two assessments of data normalization. These are the MAS5 scaling factor and the log (base 2) of the housekeeping gene set normalization factor (i.e. the median difference between the log expression levels of housekeeping genes in a given sample and those of the housekeeping genes in the reference data as a whole).

The final assessment that is made is the signal-to-noise ratio (SNR) which is the log 10 ratio of mean probe set intensity divided by the mean background intensity. This metric is designed to ensure there is a sufficiently large difference between probe and background hybridization, which will not occur if the RNA is heavily degraded or problems with procedures such as RNA labelling or chip washing have occurred.

Patient Gender Prediction

As an additional data quality control measure, a predictive Diagonal Linear Discriminant Analysis (DLDA) algorithm can be used for gender classification. Genes that were differentially expressed with a p-value less than 0.001 and minimum fold change of 2 between the 1,453 female and 695 male patients (regardless of cancer type) were selected as those which could distinguish males from females. A test sample, which is submitted for the purpose of other classification analyses, can be passed to the DLDA algorithm, which predicts the gender of the test sample based on the expression levels of the gender-discriminating genes thus identified.

The trained DLDA classifier for patient gender consists of 183 probe sets. During 3×3 fold cross validation, the gender of 97% of the 2,148 samples was correctly predicted, with a sensitivity of 97% and specificity of 95% from this internal validation exercise.

A Three-Stage Classifier for Prediction of Tumor Origin

Reflecting the nature of existing diagnostic workflows for metastatic tumors, a novel 3-tiered approach to predicting the origin of a metastatic tumor biopsy was developed. For each test sample analysed, 3 rounds of kNN classification were performed, using the 3 levels of annotation previously described, i.e. (1) anatomical system, (2) tissue and (3) histological subtype, with k=5, 3 and 1 respectively. The decreasing value of k with increasing specificity of tissue annotation was chosen based on the decreasing mean class size at each tier of the classifier, with which it is highly correlated ($r^2$=0.99).

A measurement of classifier confidence was generated for Level 1 (k=5) and Level 2 (k=3) results by determining the relative proportion of a test sample's 5 or 3 neighbors (respectively) that contribute to the winning class. The Level 3 prediction (k=1) identifies the specific individual tumor from the reference database that is closest to the test sample, in multi-dimensional gene expression space. As such, it is not possible to calculate a weighted confidence score for this level of classifier.

To determine the internal cross validation performance of the reference data and 3-tier algorithm, leave-one-out cross validation (LOOCV) was performed on the reference data set, using annotation levels 1 and 2. Results were tallied and overall percentage agreement and class-specific sensitivities and specificities were determined. The R/Bioconductor package "class" was used for kNN classification and predictive analyses.

Example 2

Two training data sets from untreated breast cancer patients (GEO accession numbers GSE4922 and GSE6352), including a total of 425 samples hybridized to Affymetrix HG-U133A arrays (GEO accession number GPL96) were downloaded in CEL file format. Clinical data were available for age, grade, ER status, tumour size, lymph node involvement, and follow-up data for up to 15 years after diagnosis were also available. An independent validation data set, consisting of samples from 128 Tamoxifen-treated patients hybridized to Affymetrix HG-U133Plus2 arrays with age, grade, ER status, nodal involvement and tumour size data, was also obtained.

A semi-supervised method substantially in line with the method described by Bair and Tibshirani (PLoS Biology 2, p 511 (2004), incorporated herein in its entirety by reference) was used, with algorithm settings of k=2 (number of principal components for the "supergenes"), p-value threshold of 0.001 for significance of a probe set being univariately correlated with survival, 10-fold cross-validation, and age, grade, nodes, tumour size and ER status used as clinical covariates. The method identified 200 prognostic marker probe sets, shown in Table 5, and gave the following model for risk of recurrence (Formula 1):

$$PI = \sum_{i=1}^{200} w_i x_i - 0.139601(\text{grade}) + 0.64644(ER) +$$
$$0.938702(\text{nodes}) + 0.010679(\text{size(mm)}) + 0.023595(\text{age}) + 0.243639$$

In Formula 1, $w_i$ is the weight of the $i^{th}$ probe set, $x_i$ is its log expression level, and PI is prognostic index.

Figure 8:
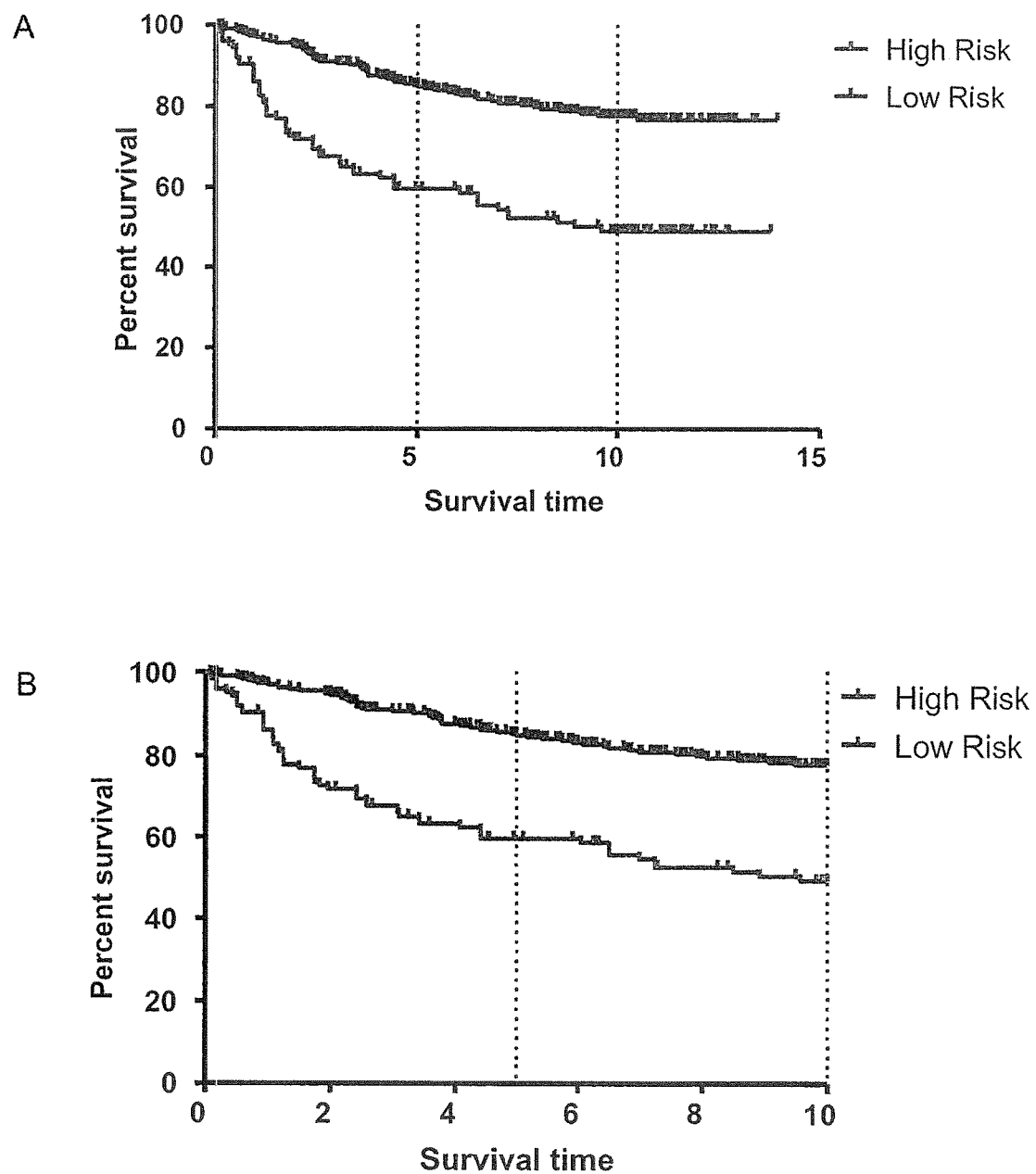
FIGS. 8(a) and 8(b) show cross-validation results for a classification program used in another Example.

FIGS. 8(a) and 8(b) show Kaplan Meier analysis of 10-fold cross validation predictions made for the 425-sample training set. Log rank tests were used to compare the survival characteristics of the two risk groups identified.

Evaluation of the cross-validation predictions made for the training set revealed a highly statistically significant difference in the survival characteristics of the high and low risk groups. Of the 425 patients, 297 (70%) were classified as high-risk and 128 (30%) as high risk. The p-value of the Kaplan Meier analysis log-rank test was P<0.0001 and the hazard ratio of the classifier was 3.75 (95% confidence interval 2.47 to 5.71).

In the training set, 85% of patients classified as low risk were disease-recurrence free at 5 years after treatment. In the high-risk group, 41% of patients experienced disease recurrence within this same time period.

Figure 9:
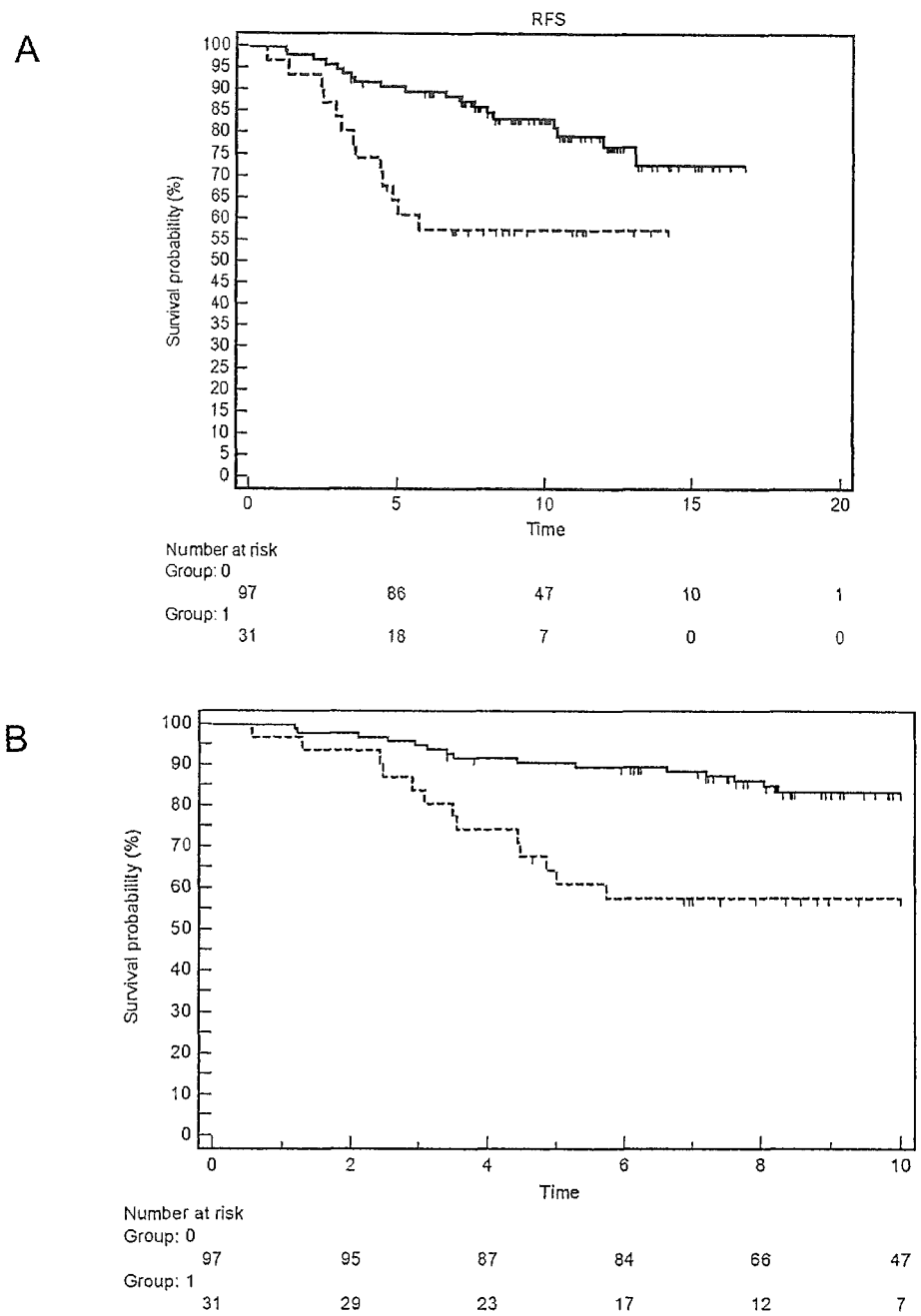
FIGS. 9(a) and 9(b) show independent validation results for the classification program used in the Example of FIGS. 8(a) and 8(b).

FIGS. 9(a) and 9(b) show survival characteristics of the high and low risk groups for the independent validation data set. The groups identified in this cohort are more similar to each other up to 3 years after diagnosis. This is likely attributable to the use of Tamoxifen in these patients. After this time point survival characteristics are significantly different.

Kaplan Meier analysis and log-rank testing was performed on the independent validation set. The P-value associated with the log rank test was P=0.0007, A hazard ratio of 4.90 (95% confidence interval 1.96 to 12.28) was observed. These figures indicate that the classifier was able to stratify the patients into two groups with markedly different survival characteristics.

Overall those individuals in the high-risk group are 4.9 times more likely to experience disease recurrence than those in the low risk group in the 10 years after diagnosis. Three quarters of the independent validation patients are classified as low risk (n=97) and of these, 90% are recurrence-free after 5 years.

Additionally, multivariate Cox Proportional Hazards analysis was performed on the 128 sample independent validation set. Two models were built and tested, one including the clinical variables only, and the other including the clinical variables and classifier prediction variable (high/low risk). The significance level of the clinical-only model was P=0.0291, whilst for the clinical+classifier model it was P=0.0126. The classifier remained independently prognostic in the second model (P=0.048).

These results indicate that the classifier (comprised of 200 genes+5 clinical variables) is able to stratify patients into high and low risk groups for disease recurrence. Furthermore, the stratification of patients is more statistically significant than the use of clinical variables alone. The prognostic significance of the classifier has been evaluated in patients who do and do not receive Tamoxifen treatment following their initial diagnosis and surgical procedure.

TABLE 4

List of probes used for tumor origin prediction

| Affymetrix Probe ID | Genbank Accession number | Unigene ID | Gene symbol |
|---|---|---|---|
| 204769_s_at | M74447 | Hs.502 | TAP2 |
| 206422_at | NM_002054 | Hs.516494 | GCG |
| 209937_at | BC001386 | Hs.133527 | TM4SF4 |
| 204673_at | NM_002457 | Hs.315 | MUC2 |
| 1554436_a_at | AY126671 | Hs.660883 | REG4 |
| 214303_x_at | AW192795 | Hs.534332 | MUCSAC |
| 204697_s_at | NM_001275 | Hs.150793 | CHGA |
| 223447_at | AY007243 | Hs.660883 | REG4 |
| 242601_at | AA600175 | Hs.443169 | HEPACAM2 |
| 215688_at | AL359931 | Hs.591111 | RASGRF1 |
| 208131_s_at | NM_000961 | Hs.302085 | PTGIS |
| 205249_at | NM_000399 | Hs.1395 | EGR2 |
| 206750_at | NM_002360 | Hs.520612 | MAFK |
| 210170_at | BC001017 | Hs.85862 | PDLIM3 |
| 203240_at | NM_003890 | Hs.111732 | FCGBP |
| 207214_at | NM_014471 | Hs.555934 | SPINK4 |
| 214385_s_at | AI521646 | Hs.534332 | MUCSAC |
| 216206_x_at | BC005365 | Hs.531754 | MAP2K7 |
| 228335_at | AW264204 | Hs.31595 | CLDN11 |
| 227971_at | AI653107 | Hs.209527 | NRK |
| 207591_s_at | NM_006015 | Hs.468972 | ARID1A |
| 239144_at | AA835648 | Hs.713609 | B3GAT2 |
| 203806_s_at | NM_000135 | Hs.567267 | FANCA |
| 232546_at | AL136528 | Hs.697294 | TP73 |

TABLE 4-continued

List of probes used for tumor origin prediction

| Affymetrix Probe ID | Genbank Accession number | Unigene ID | Gene symbol |
|---|---|---|---|
| 201262_s_at | NM_001711 | Hs.821 | BGN |
| 206690_at | NM_001094 | Hs.368417 | ACCN1 |
| 201431_s_at | NM_001387 | Hs.519659 | DPY5L3 |
| 233985_x_at | AV706485 | Hs.21816 | PPP1R9A |
| 210240_s_at | U20498 | Hs.435051 | CDKN2D |
| 229529_at | AI827830 | Hs.78061 | TCF21 |
| 231542_at | AL157421 | | |
| 226755_at | AI375939 | Hs.510543 | LOC642587 |
| 223597_at | AB036706 | Hs.50813 | ITLN1 |
| 204337_at | AL514445 | Hs.386726 | RGS4 |
| 236017_at | AI199453 | Hs.105818 | CDKL3 |
| 205822_s_at | NM_002130 | Hs.397729 | HMGCS1 |
| 216339_s_at | AF086641 | | TNXA |
| 228658_at | R54042 | Hs.653712 | MIAT |
| 228399_at | AI569974 | Hs.123933 | OSR1 |
| 208323_s_at | NM_004306 | Hs.181107 | ANXA13 |
| 1560770_at | BQ719658 | Hs.387804 | PABPC1 |
| 202928_s_at | NM_024165 | Hs.166204 | PHF1 |
| 204359_at | NM_013231 | Hs.533710 | FLRT2 |
| 220037_s_at | NM_016164 | Hs.655332 | LYVE1 |
| 201666_at | NM_003254 | Hs.522632 | TIMP1 |
| 205161_s_at | NM_003847 | Hs.31034 | PEX11A |
| 211062_s_at | BC006393 | Hs.78068 | CPZ |
| 203929_s_at | AI056359 | Hs.101174 | MAPT |
| 238878_at | AA496211 | Hs.300304 | ARX |
| 229335_at | BE645821 | Hs.370984 | CADM4 |
| 229212_at | BE220341 | Hs.644056 | CSNK2A1 |
| 219059_s_at | AL574194 | Hs.655332 | LYVE1 |
| 1559064_at | BC035502 | Hs.601591 | NUP153 |
| 228004_at | AL121722 | | C20orf56 |
| 230242_at | AA634220 | Hs.13349 | NFASC |
| 206115_at | NM_004430 | Hs.534313 | EGR3 |
| 238231_at | AV700263 | Hs.233458 | NFYC |
| 236131_at | AW452631 | | |
| 207935_s_at | NM_002274 | Hs.654550 | KRT13 |
| 214079_at | AK000345 | Hs.272499 | DHRS2 |
| 241987_x_at | BF029081 | Hs.567758 | SNX31 |
| 206463_s_at | NM_005794 | Hs.272499 | DHRS2 |
| 2207779_at | NM_016233 | Hs.149195 | PADI3 |
| 214624_at | AA548647 | Hs.159309 | UPK1A |
| 203074_at | NM_001630 | Hs.705389 | ANXA8L2 |
| 205319_at | NM_005672 | Hs.652235 | PSCA |
| 202226_s_at | NM_016823 | Hs.638121 | CRK |
| 210655_s_at | AF041336 | Hs.220950 | FOXO3 |
| 1552627_a_at | NM_001173 | Hs.592313 | ARHGAPS |
| 1556168_s_at | BC042133 | Hs.361778 | LOC339766 |
| 210143_at | AF196478 | Hs.188401 | ANXA10 |
| 208750_s_at | AA580004 | Hs.286221 | ARF1 |
| 204268_at | NM_005978 | Hs.516484 | S100A2 |
| 207782_s_at | NM_007319 | Hs.3260 | PSEN1 |
| 209863_s_at | AF091627 | Hs.137569 | TP63 |
| 220773_s_at | NM_020806 | Hs.208765 | GPHN |
| 202825_at | NM_001151 | Hs.246506 | SLC25A4 |
| 242733_at | AI457588 | | |
| 39248_at | N74607 | Hs.234542 | AQP3 |
| 214908_s_at | AC004893 | Hs.203952 | TRRAP |
| 210337_s_at | U18197 | Hs.387567 | ACLY |
| 200693_at | NM_006826 | Hs.74405 | YWHAQ |
| 203953_s_at | BE791251 | Hs.647023 | CLDN3 |
| 232481_at | AL137517 | Hs.525105 | SLITRK6 |
| 206658_at | NM_030570 | Hs.488861 | UPK3B |
| 214487_at | NM_002886 | Hs.98643 | RAP2B |
| 242509_at | R71072 | | |
| 230188_at | AW138350 | Hs.4285 | ICHTHYIN |
| 213992_at | AI889941 | Hs.145586 | COL4A6 |
| 232176_at | R70320 | Hs.525105 | SLITRK6 |
| 202927_at | NM_006221 | Hs.465849 | PIN1 |
| 229151_at | BE673587 | Hs.101307 | SLC14A1 |
| 1555814_a_at | AF498970 | Hs.247077 | RHOA |
| 206209_at | NM_000717 | Hs.89485 | CA4 |
| 231904_at | AU122448 | Hs.365116 | U2AF1 |
| 211797_s_at | U62296 | Hs.233458 | NFYC |
| 208852_at | AI761759 | Hs.699155 | CANX |
| 219936_s_at | NM_023915 | Hs.591292 | GPR87 |
| 235976_at | AI680986 | Hs.525105 | SLITRK6 |
| 213506_at | AA594937 | Hs.99141 | COBL |
| 206504_at | NM_000782 | Hs.89663 | CYP24A1 |
| 217294_s_at | U88968 | Hs.517145 | ENO1 |
| 1564494_s_at | AK075503 | Hs.464336 | P4HB |
| 209772_s_at | X69397 | Hs.644105 | CD24 |
| 236926_at | AW074836 | Hs.173984 | TBX1 |
| 208621_s_at | BF663141 | Hs.487027 | EZR |
| 206771_at | NM_006953 | Hs.632787 | UPK3A |
| 202820_at | NM_001621 | Hs.171189 | AHR |
| 200059_s_at | BC001360 | Hs.247077 | RHOA |
| 1558214_s_at | BG330076 | Hs.534797 | CTNNA1 |
| 218284_at | NM_015400 | Hs.618504 | SMAD3 |
| 207685_s_at | NM_001228 | Hs.599762 | CASP8 |
| 201461_s_at | NM_004759 | Hs.643566 | MAPKAPK2 |
| 200624_s_at | AA577695 | Hs.268939 | MATR3 |
| 219909_at | NM_024302 | Hs.380710 | MMP28 |
| 207612_at | NM_003393 | Hs.421281 | WNT8B |
| 205856_at | NM_015865 | Hs.101307 | SLC14A1 |
| 211934_x_at | W87689 | Hs.595071 | GANAB |
| 204379_s_at | NM_000142 | Hs.1420 | FGFR3 |
| 202527_s_at | NM_005359 | Hs.75862 | SMAD4 |
| 208853_s_at | L18887 | Hs.699155 | CANX |
| 232116_at | AL137763 | Hs.657920 | GRHL3 |
| 212236_x_at | Z19574 | Hs.2785 | KRT17 |
| 201017_at | BG149698 | Hs.522590 | EIF1AX |
| 206393_at | NM_003282 | Hs.523403 | TNNI2 |
| 210065_s_at | AB002155 | Hs.271580 | UPK1B |
| 209192_x_at | BC000166 | Hs.528299 | KATS |
| 202354_s_at | AW190445 | Hs.68257 | GTF2F1 |
| 235417_at | BF689253 | Hs.62604 | SPOCD1 |
| 211151_x_at | AF185611 | Hs.655229 | GH1 |
| AFFX-HSAC07/X00351_5_at | AFFX-HSAC07/X00351_5 | Hs.520640 | ACTB |
| 204602_at | NM_012243 | Hs.40499 | DKK1 |
| 220026_at | NM_012128 | Hs.567422 | CLCA4 |
| 210756_s_at | AF308601 | Hs.487360 | NOTCH2 |
| 205132_at | NM_005159 | Hs.709351 | ACTC1 |
| 213022_s_at | NM_007124 | Hs.133135 | UTRN |
| 206207_at | NM_001828 | Hs.889 | CLC |
| 210064_s_at | NM_006952 | Hs.271580 | UPK18 |
| 1558099_s_at | BI832451 | Hs.268939 | MATR3 |
| 213002_at | AA770596 | Hs.519909 | MARCKS |
| 217234_s_at | AF199015 | Hs.487027 | EZR |
| 225211_at | AW139723 | Hs.334846 | PVRL1 |
| 223687_s_at | AA723810 | Hs.69517 | LY6K |
| 1556793_a_at | AK091138 | Hs.592149 | FAM83C |
| 1552496_a_at | NM_015198 | Hs.99141 | COBL |
| 205157_s_at | NM_000422 | Hs.2785 | KRT17 |
| 204247_s_at | NM_004935 | Hs.647078 | CDK5 |
| 201401_s_at | M80776 | Hs.83636 | ADRBK1 |
| 200664_s_at | BG537255 | Hs.515210 | DNAJB1 |
| 209364_at | U66879 | Hs.370254 | BAD |
| 202449_s_at | NM_002957 | Hs.590886 | RXRA |
| 214639_s_at | S79910 | Hs.67397 | HOXA1 |
| AFFX-HUMISGF3A/M97935_s_at | AFFX-HUMISGF3A/M97935-5 | Hs.642990 | STAT1 |
| 227143_s_at | AA706658 | Hs.591054 | BID |
| 215050_x_at | BF325734 | Hs.643566 | MAPKAPK2 |
| 215037_s_at | U72398 | Hs.516966 | BCL2L1 |
| 209051_s_at | AF295773 | Hs.106185 | RALGD5 |
| 206466_at | AB014531 | Hs.655760 | ACSBG1 |
| 203582_s_at | NM_004578 | Hs.296169 | RAB4A |
| 205523_at | U43328 | Hs.2799 | HAPLN1 |
| 201131_s_at | NM_004360 | Hs.461086 | CDH1 |
| 222008_at | NM_001851 | Hs.590892 | COL9A1 |
| 205524_s_at | NM_001884 | Hs.2799 | HAPLN1 |
| 217744_s_at | NM_022121 | Hs.520421 | PERP |
| 226213_at | AV681807 | Hs.118681 | ERBB3 |
| 209902_at | U49844 | Hs.271791 | ATR |
| 201727_s_at | NM_001419 | Hs.184492 | ELAVL1 |
| 213909_at | AU147799 | Hs.288467 | LRRC15 |

TABLE 4-continued

List of probes used for tumor origin prediction

| Affymetrix Probe ID | Genbank Accession number | Unigene ID | Gene symbol |
|---|---|---|---|
| 213487_at | AI762811 | Hs.465627 | MAP2K2 |
| 231175_at | N48613 | Hs.582993 | C6orf65 |
| 206869_at | NM_001267 | Hs.97220 | CHAD |
| 209771_x_at | AA761181 | | |
| 1557053_s_at | BC035653 | Hs.529420 | UBE2G2 |
| 208857_s_at | AF119911 | Hs.529862 | CSNK1A1 |
| 221215_s_at | NM_020639 | Hs.517310 | RIPK4 |
| 203889_at | NM_003020 | Hs.156540 | SCG5 |
| 227803_at | AA609053 | Hs.35198 | ENPP5 |
| 216379_x_at | AK000168 | | |
| 202454_s_at | NM_001982 | Hs.118681 | ERBB3 |
| 206075_s_at | NM_001895 | Hs.644056 | CSNK2A1 |
| 205066_s_at | NM_006208 | Hs.527295 | ENPP1 |
| 232523_at | AU144892 | Hs.438709 | MEGF10 |
| 231736_at | NM_020300 | Hs.389700 | MGST1 |
| 208651_x_at | M58664 | Hs.644105 | CD24 |
| 229271_x_at | BG028597 | Hs.523446 | COL11A1 |
| 201596_x_at | NM_000224 | Hs.406013 | KRT18 |
| 225275_at | AA053711 | Hs.482730 | EDIL3 |
| 201235_s_at | BG339064 | Hs.519162 | BTG2 |
| 231867_at | AB032953 | Hs.654631 | OD22 |
| 222392_x_at | AI251830 | Hs.520421 | PERP |
| 217888_s_at | NM_018209 | Hs.25584 | ARFGAP1 |
| 204037_at | BF055366 | Hs.126667 | LPAR1 |
| 206298_at | NM_021226 | Hs.655672 | ARHGAP22 |
| 160020_at | 248481 | Hs.2399 | MMP14 |
| 213870_at | AL031228 | Hs.390171 | COL11A2 |
| 212089_at | M13452 | Hs.594444 | LMNA |
| 221900_at | AI806793 | Hs.353001 | COL8A2 |
| 224918_x_at | AI220117 | Hs.389700 | MGST1 |
| 204320_at | NM_001854 | Hs.523446 | COL11A1 |
| 218186_at | NM_020387 | Hs.632469 | RAB3 |
| 204736_s_at | NM_001897 | Hs.513044 | CSPG4 |
| 213276_at | T15766 | Hs.351887 | CAMK2B |
| 202677_at | NM_002890 | Hs.664080 | RASA1 |
| 204724_s_at | NM_001853 | Hs.126246 | COL9A3 |
| 205959_at | NM_002427 | Hs.2936 | MMP13 |
| 208992_s_at | BC000627 | Hs.463059 | STAT3 |
| 266_s_at | L33930 | Hs.644105 | CD24 |
| 208650_s_at | BG327863 | Hs.644105 | CD24 |
| 229088_at | BF591996 | Hs.527295 | ENPP1 |
| 213943_at | X99268 | Hs.66744 | TWIST1 |
| 209008_x_at | U76549 | Hs.533782 | KRT8 |
| 214247_s_at | AU148057 | Hs.292156 | DKK3 |
| 210827_s_at | U73844 | Hs.67928 | ELF3 |
| 225147_at | AL521959 | Hs.487479 | CYTH3 |
| 214726_x_at | AL556041 | Hs.183706 | ADD1 |
| 205475_at | NM_007281 | Hs.7122 | SCRG1 |
| 1565269_s_at | AF047022 | Hs.648565 | ATF1 |
| 1565162_s_at | D16947 | Hs.389700 | MGST1 |
| 217901_at | BF031829 | Hs.412597 | DSG2 |
| 37892_at | J04177 | Hs.523446 | COL11A1 |
| 204854_at | NM_014262 | Hs.631655 | LEPREL2 |
| 211300_s_at | K08199 | Hs.654481 | TP53 |
| 201839_s_at | NM_002354 | Hs.542060 | TACSTD1 |
| 213791_at | NM_006211 | Hs.339831 | PENK |
| 224650_at | AL117621 | Hs.201083 | MAL2 |
| 211597_s_at | AB059408 | Hs.654864 | HOPX |
| 228834_at | BF240286 | Hs.709952 | TOB1 |
| 206655_s_at | NM_000407 | Hs.283743 | GP1BB |
| 206237_s_at | NM_013957 | Hs.453951 | NRG1 |
| 203352_at | NM_002552 | Hs.558364 | ORC4L |
| 223319_at | AF272663 | Hs.208765 | GPHN |
| 238516_at | BF247383 | Hs.471119 | BMPR2 |
| 205980_s_at | NM_015366 | Hs.102336 | PRR5 |
| 219183_s_at | NM_013385 | Hs.170944 | CYTH4 |
| 202790_at | NM_001307 | Hs.513915 | CLDN7 |
| 229296_at | AI659477 | Hs.711775 | LOC100128501 |
| 207384_at | NM_005091 | Hs.137583 | PGLYRP1 |
| 201792_at | NM_001129 | Hs.439463 | AEBP1 |
| 224506_at | BC006362 | Hs.134292 | PPAPDC3 |
| 203954_x_at | NM_001306 | Hs.647023 | CLDN3 |
| 220273_at | NM_014443 | Hs.156979 | IL17B |
| 231941_s_at | AB037780 | Hs.599259 | MUC20 |
| 226210_s_at | AI291123 | Hs.525589 | MEG3 |
| 216326_s_at | AF059650 | Hs.519632 | HDAC3 |
| 229218_at | AA628535 | Hs.489142 | COL1A2 |
| 236028_at | BE466675 | Hs.518726 | IBSP |
| 227510_x_at | AL037917 | Hs.642877 | MALAT1 |
| 203351_s_at | AF047598 | Hs.558364 | ORC4L |
| 208643_s_at | J04977 | Hs.388739 | XRCC5 |
| 206201_s_at | NM_005924 | Hs.170355 | MEOX2 |
| 203325_s_at | AI130969 | Hs.210283 | COL5A1 |
| 209466_x_at | M57399 | Hs.371249 | PTN |
| 202987_at | BE251211 | Hs.626637 | LOXL2 |
| 223199_at | AA404592 | Hs.515032 | MKNK2 |
| 214917_at | AK024252 | Hs.43322 | PRKAA1 |
| 205257_s_at | NM_001635 | Hs.592182 | AMPH |
| 223749_at | AF329836 | Hs.110062 | C1QTNF2 |
| 209604_s_at | BC003070 | Hs.524134 | GATA3 |
| 209603_at | AI796169 | Hs.524134 | GATA3 |
| 209602_s_at | AI796169 | Hs.524134 | GATA3 |
| 244820_at | AI086336 | | |
| 210239_at | U90304 | Hs.435730 | IRX5 |
| 223864_at | AF269087 | Hs.373787 | ANKRD30A |
| 206509_at | NM_002652 | Hs.99949 | PIP |
| 206378_at | NM_002411 | Hs.45452 | SCGB2A2 |
| 237339_at | AI668620 | Hs.144151 | hCG_25653 |
| 227629_at | AA843963 | Hs.368587 | PRLR |
| 209343_at | BC002449 | Hs.516769 | EFHD1 |
| 1553602_at | NM_058173 | Hs.348419 | MUCL1 |
| 217014_s_at | AC004522 | Hs.546239 | AZGP1 |
| 209309_at | D90427 | Hs.546239 | AZGP1 |
| 214451_at | NM_003221 | Hs.33102 | TFAP2B |
| 1559949_at | TS6980 | | |
| 237395_at | AV700083 | Hs.176588 | CYP4Z1 |
| 205913_at | NM_002666 | Hs.103253 | PLIN |
| 202575_at | NM_001878 | Hs.405652 | CRABP2 |
| 1553434_at | NM_173534 | Hs.591431 | CYP4Z2P |
| 204227_s_at | BF343007 | Hs.519880 | TFAP2A |
| 206227_at | NM_003613 | Hs.442180 | CILP |
| 1553394_a_at | NM_003221 | Hs.33102 | TFAP2B |
| 228462_at | AI928035 | Hs.282089 | IRX2 |
| 1560850_at | BC016831 | | |
| 230472_at | AI870306 | Hs.424156 | IRX1 |
| 238021_s_at | AA954994 | Hs.237396 | hCG_1815491 |
| 229476_s_at | AW272342 | Hs.591969 | THRSP |
| 204942_s_at | NM_000695 | Hs.87539 | ALDH3B2 |
| 219197_s_at | AI424243 | Hs.523468 | SCUBE2 |
| 201525_at | NM_001647 | Hs.522555 | APOD |
| 219288_at | NM_020685 | Hs.47166 | C3orf14 |
| 207175_at | NM_004797 | Hs.80485 | ADIPOQ |
| 224146_at | AF352582 | Hs.652267 | ABCC11 |
| 227475_at | AI676059 | Hs.591352 | FOXQ1 |
| 202376_at | NM_001085 | Hs.534293 | SERPINA3 |
| 237350_at | AW027968 | Hs.653449 | TTC36 |
| 226560_at | AA576959 | | |
| 230147_at | AI378647 | Hs.42502 | F2RL2 |
| 204654_s_at | NM_003220 | Hs.519880 | TFAP2A |
| 236534_at | W69365 | Hs.591473 | BNIPL |
| 223551_at | AF225513 | Hs.486354 | PKIB |
| 205792_at | NM_003881 | Hs.592145 | WISP2 |
| 237086_at | AI693336 | Hs.163484 | FOXA1 |
| 224209_s_at | AF019638 | Hs.494163 | GDA |
| 202291_s_at | NM_000900 | Hs.365706 | MGP |
| 227614_at | W81116 | Hs.522988 | HKDC1 |
| 229638_at | AI681917 | Hs.499205 | IRX3 |
| 205286_at | U85658 | Hs.473152 | TFAP2C |
| 228481_at | BG541187 | | |
| 230560_at | N21096 | Hs.508958 | STXBP6 |
| 204931_at | NM_003206 | Hs.78061 | TCF21 |
| 209815_at | BG054916 | Hs.494538 | PTCH1 |
| 203680_at | NM_002736 | Hs.433068 | PRKAR2B |
| 240192_at | AI631850 | Hs.669736 | FLJ45983 |
| 222773_s_at | AA554045 | Hs.47099 | GALNT12 |
| 203980_at | NM_001442 | Hs.391561 | FABP4 |
| 1553622_a_at | NM_152597 | Hs.129598 | FSIP1 |
| 213093_at | AI471375 | Hs.531704 | PRKCA |

TABLE 4-continued

List of probes used for tumor origin prediction

| Affymetrix Probe ID | Genbank Accession number | Unigene ID | Gene symbol |
|---|---|---|---|
| 226978_at | AA910945 | Hs.103110 | PPARA |
| 214243_s_at | AL450314 | Hs.360940 | SERHL2 |
| 227376_at | AW021102 | Hs.21509 | GLI3 |
| 213506_at | BE965369 | Hs.154299 | F2RL1 |
| 204073_s_at | NM_013279 | Hs.473109 | C11orf9 |
| 238481_at | AW512787 | Hs.365706 | MGP |
| 205313_at | NM_000458 | Hs.191144 | HNF1B |
| 230163_at | AW263087 | Hs.388347 | LOC143381 |
| 203510_at | BG170541 | Hs.132966 | MET |
| 243241_at | AW341473 | | |
| 227550_at | AW242720 | Hs.388347 | LOC143381 |
| 224458_at | BC006115 | Hs.655738 | C9orf125 |
| 1555778_a_at | AY140646 | Hs.136348 | POSTN |
| 204179_at | NM_005368 | Hs.517586 | MB |
| 223122_s_at | AF311912 | Hs.481022 | SFRP2 |
| 217276_x_at | AL590118 | Hs.360940 | SERHL2 |
| 217284_x_at | AL589866 | Hs.360940 | SERHL2 |
| 1556474_a_at | AK095698 | Hs.653239 | FLI38379 |
| 227198_at | AW085505 | Hs.444444 | AFF3 |
| 209341_s_at | AU153366 | Hs.656458 | IKBKB |
| 220994_s_at | NM_014178 | Hs.508958 | STXBP6 |
| 204667_at | NM_004496 | Hs.163484 | FOXA1 |
| 210809_at | D13665 | Hs.136348 | POSTN |
| 205476_at | NM_004591 | Hs.75498 | CCL20 |
| 227174_at | Z98443 | Hs.122125 | WDR72 |
| 229477_at | AW272342 | Hs.591969 | THRSP |
| 223121_s_at | AW003584 | Hs.481022 | SFRP2 |
| 203843_at | AA906056 | Hs.445387 | RPS6KA3 |
| 206401_s_at | J03778 | Hs.101174 | MAPT |
| 205253_at | NM_002585 | Hs.654412 | PBX1 |
| 232286_at | AA572675 | | |
| 204014_at | NM_001394 | Hs.417962 | DUSP4 |
| 226777_at | AA147933 | | |
| 213068_at | AI146848 | Hs.80552 | DPT |
| 214235_at | X90579 | Hs.695915 | CYP3ASP2 |
| 229580_at | R71596 | | |
| 229150_at | AI810764 | | |
| 223437_at | N48315 | Hs.103110 | PPARA |
| 203540_at | NM_002055 | Hs.514227 | GFAP |
| 205103_at | NM_006365 | Hs.380027 | C1orf61 |
| 229259_at | AL133013 | Hs.514227 | GFAP |
| 206826_at | NM_002677 | Hs.571512 | PMP2 |
| 235127_at | AI699994 | Hs.571512 | PMP2 |
| 228170_at | AL355743 | Hs.56663 | OLIG1 |
| 231898_x_at | AW026426 | Hs.654932 | SOX2OT |
| 219107_at | NM_021948 | Hs.516904 | BCAN |
| 203724_s_at | NM_014961 | Hs.595749 | RUFY3 |
| 223673_at | AF332192 | Hs.388347 | RFX4 |
| 209469_at | BF939489 | Hs.75819 | GPM6A |
| 206397_x_at | NM_001492 | Hs.412355 | GDF1 |
| 209168_at | AW148844 | Hs.495710 | GPM6B |
| 235118_at | AV724768 | | |
| 204471_at | NM_002045 | Hs.134974 | GAP43 |
| 210198_s_at | BC002665 | Hs.1787 | PLP1 |
| 209197_at | AA626780 | Hs.32984 | SYT11 |
| 206190_at | NM_005291 | Hs.46453 | GPR17 |
| 213825_at | AA757419 | Hs.176977 | OLIG2 |
| 230496_at | BE046923 | Hs.528335 | FAM123A |
| 209072_at | M13577 | Hs.551713 | MBP |
| 209470_s_at | D49958 | Hs.75819 | GPM6A |
| 225491_at | AL157452 | Hs.502338 | SLC1A2 |
| 236761_at | AI939602 | Hs.659164 | LHFPL3 |
| 209170_s_at | AF016004 | Hs.495710 | GPM6B |
| 209169_at | N63576 | Hs.495710 | GPM6B |
| 204469_at | NM_002851 | Hs.489824 | PTPRZ1 |
| 203562_at | NM_005103 | Hs.224008 | FEZ1 |
| 229921_at | BF196255 | Hs.151219 | KIF5A |
| 205143_at | NM_004386 | Hs.169047 | NCAN |
| 219416_at | NM_020659 | Hs.268728 | TTYH1 |
| 209617_s_at | AF035302 | Hs.314543 | CTNND2 |
| 238850_at | AW015083 | Hs.12827 | LOC645323 |
| 203526_s_at | M74088 | Hs.158932 | APC |
| 222780_s_at | AI870583 | Hs.533446 | BAALC |
| 226690_at | AW451961 | Hs.377783 | ADCYAP1R1 |
| 203151_at | AW296788 | Hs.194301 | MAP1A |
| 212636_at | AL031781 | Hs.510324 | QKI |
| 235465_at | N66614 | Hs.528335 | FAM123A |
| 207323_s_at | NM_002385 | Hs.551713 | MBP |
| 227394_at | W94001 | Hs.503878 | NCAM1 |
| 1552754_a_at | AA640422 | Hs.164578 | CADM2 |
| 228581_at | AW071744 | Hs.408960 | KCNJ10 |
| 229875_at | AI363193 | Hs.525485 | ZDHHC22 |
| 39966_at | AF059274 | Hs.45127 | CSPG5 |
| 209167_at | AI419030 | Hs.495710 | GPM6B |
| 200433_x_at | H39185 | | |
| 1558388_a_at | R41806 | | |
| 226281_at | BF059512 | Hs.234074 | DNER |
| 1569872_a_at | BC036550 | Hs.371980 | LOC650392 |
| 206408_at | NM_015564 | Hs.656653 | LRRTM2 |
| 1561658_at | AF086066 | | |
| 213395_at | AL022327 | Hs.517729 | MLC1 |
| 244403_at | R49501 | Hs.126135 | CRB1 |
| 230272_at | AA464844 | Hs.12827 | LOC645323 |
| 221236_s_at | NM_030795 | Hs.201058 | STMN4 |
| 1558189_a_at | BG819064 | Hs.554030 | LOC284570 |
| 216963_s_at | AF279774 | Hs.134974 | GAP43 |
| 218899_at | NM_024812 | Hs.533446 | BAALC |
| 210432_s_at | AF225986 | Hs.435274 | SCN3A |
| 209839_at | AL136712 | Hs.654775 | DNM3 |
| 223603_at | AB026054 | Hs.189482 | RNF112 |
| 213841_at | BE223030 | | |
| 227401_at | BE856748 | Hs.655142 | IL17D |
| 213721_at | L07335 | Hs.518438 | SOX2 |
| 238003_at | AI885128 | Hs.652245 | HEPN1 |
| 213486_at | BF435376 | Hs.6421 | COPG2 |
| 212843_at | AA126505 | Hs.503878 | NCAM1 |
| 205344_at | NM_006574 | Hs.45127 | CSPG5 |
| 210383_at | AF225985 | Hs.22654 | SCN1A |
| 227084_at | AW339310 | Hs.643454 | DTNA |
| 203525_s_at | AI375486 | Hs.158932 | APC |
| 227984_at | BE464483 | Hs.371980 | LOC650392 |
| 239230_at | AW079166 | Hs.57971 | HES5 |
| 227612_at | R20763 | Hs.1701 | ELAVL3 |
| 210106_at | D63412 | Hs.315369 | AQP4 |
| 221523_at | AF229053 | Hs.516904 | BCAN |
| 229734_at | BF507379 | Hs.504370 | LOC283174 |
| 244739_at | AI051769 | Hs.263671 | RDX |
| 230144_at | AW294729 | Hs.377070 | GRIA3 |
| 1558795_at | AL833240 | Hs.709829 | LOC728052 |
| 230942_at | AI47740 | Hs.99272 | CMTM5 |
| 213849_s_at | AA974416 | Hs.655213 | PPP2R2B |
| 211071_s_at | BC006471 | Hs.75823 | MLLT11 |
| 226228_at | T15657 | Hs.315369 | AQP4 |
| 231430_at | AW205640 | Hs.448218 | FAM181B |
| 209618_at | U96136 | Hs.314543 | CTNND2 |
| 222547_at | AL561281 | Hs.431550 | MAP4K4 |
| 228038_at | AI669815 | Hs.518438 | SOX2 |
| 226623_at | AI829726 | Hs.499704 | PHYHIPL |
| 223536_at | AL136559 | Hs.21963 | PSD2 |
| 205320_at | NM_005883 | Hs.446376 | APC2 |
| 207093_s_at | NM_002544 | Hs.113874 | OMG |
| 228501_at | BF055343 | Hs.411308 | GALNTL2 |
| 229799_s_at | AI569787 | Hs.503878 | NCAM1 |
| 205638_at | NM_001704 | Hs.13261 | BAI3 |
| 218380_at | NM_021730 | Hs.104305 | NLRP1 |
| 205737_at | NM_004518 | Hs.161851 | KCNQ2 |
| 211906_s_at | AB046400 | Hs.123035 | SERPINB4 |
| 210413_x_at | U19557 | Hs.123035 | SERPINB4 |
| 209719_x_at | U19556 | Hs.227948 | SERPINB3 |
| 209720_s_at | BC005224 | Hs.227948 | SERPINB3 |
| 217272_s_at | AJ001698 | Hs.241407 | SERPINB13 |
| 214580_x_at | AL569511 | Hs.700779 | KRT6A |
| 209125_at | J00269 | Hs.700779 | KRT6A |
| 206276_at | NM_003695 | Hs.415762 | LY6D |
| 206400_at | NM_002307 | Hs.707031 | LGALS7 |
| 209126_x_at | L42612 | Hs.709235 | KRT6B |
| 211361_s_at | AJ001696 | Hs.241407 | SERPINB13 |
| 205064_at | NM_003125 | Hs.1075 | SPRR1B |

TABLE 4-continued

List of probes used for tumor origin prediction

| Affymetrix Probe ID | Genbank Accession number | Unigene ID | Gene symbol |
|---|---|---|---|
| 216258_s_at | BE148534 | Hs.241407 | SERPINB13 |
| 216237_s_at | AA807529 | Hs.517582 | MCM5 |
| 201820_at | NM_000424 | Hs.433845 | KRT5 |
| 209644_x_at | U38945 | Hs.512599 | CDKN2A |
| 203535_at | NM_002965 | Hs.112405 | S100A9 |
| 209587_at | U70370 | Hs.84136 | PITX1 |
| 202917_s_at | NM_002964 | Hs.416073 | S100A8 |
| 204971_at | NM_005213 | Hs.518198 | CSTA |
| 206032_at | AI797281 | Hs.41690 | DSC3 |
| 235075_at | AI813438 | Hs.1925 | DSG3 |
| 206165_at | NM_006536 | Hs.241551 | CLCA2 |
| 218990_s_at | NM_005416 | Hs.139322 | SPRR3 |
| 1552487_a_at | NM_001717 | Hs.459153 | BNC1 |
| 220013_at | NM_024794 | Hs.156457 | ABHD9 |
| 209800_at | AF061812 | Hs.655160 | KRT16 |
| 214549_x_at | NM_005987 | Hs.46320 | SPRR1A |
| 205349_at | NM_002068 | Hs.73797 | GNA15 |
| 219554_at | NM_016321 | Hs.459284 | RHCG |
| 213680_at | AI831452 | Hs.709235 | KRT6B |
| 207039_at | NM_000077 | Hs.512599 | CDKN2A |
| 206156_at | NM_005268 | Hs.198249 | GJB5 |
| 206421_s_at | NM_003784 | Hs.138202 | SERPINB7 |
| 228575_at | AL578102 | Hs.61232 | IL20RB |
| 210020_x_at | M58026 | Hs.239600 | CALML3 |
| 213240_s_at | X07695 | Hs.654610 | KRT4 |
| 232082_x_at | BF575466 | Hs.139322 | SPRR3 |
| 244107_at | AW189097 | | |
| 221854_at | AI378979 | Hs.497350 | PKP1 |
| 204952_at | NM_014400 | Hs.631594 | LYPD3 |
| 206033_s_at | NM_001941 | Hs.41690 | DSC3 |
| 205595_at | NM_001944 | Hs.1925 | DSG3 |
| 205916_at | NM_002963 | Hs.112408 | S100A7 |
| 1559607_s_at | AL703282 | Hs.254338 | GBP6 |
| 206164_at | NM_006536 | Hs.241551 | CLCA2 |
| 238603_at | AI611973 | Hs.710375 | LOC254559 |
| 206122_at | NM_006942 | Hs.95582 | SOX15 |
| 233064_at | AL365406 | Hs.65750 | LOC388494 |
| 208502_s_at | NM_002653 | Hs.84136 | PITX1 |
| 212657_s_at | U65590 | Hs.81134 | IL1RN |
| 206166_s_at | AF043977 | Hs.241551 | CLCA2 |
| 229566_at | AA149250 | Hs.463652 | LOC645638 |
| 33322_i_at | X57348 | Hs.523718 | SFN |
| 39249_at | AB001325 | Hs.234642 | AQP3 |
| 208153_s_at | NM_001447 | Hs.591255 | FAT2 |
| 207121_s_at | NM_002748 | Hs.411847 | MAPK6 |
| 33323_r_at | X57348 | Hs.523718 | SFN |
| 201755_at | NM_006739 | Hs.517582 | MCM5 |
| 236444_x_at | BE785577 | Hs.436898 | LOC389328 |
| 217528_at | BF003134 | Hs.241551 | CLCA2 |
| 208539_x_at | NM_006945 | Hs.505327 | SPRR2D |
| 211002_s_at | AF230389 | Hs.504115 | TRIM29 |
| 214370_at | AW238654 | Hs.416073 | S100A8 |
| 238460_at | AI590662 | Hs.379821 | FAM83A |
| 202504_at | NM_012101 | Hs.504115 | TRIM29 |
| 224204_x_at | AF231339 | Hs.434269 | ARNTL2 |
| 201202_at | NM_002592 | Hs.147433 | PCNA |
| 209260_at | BC000329 | Hs.523718 | SFN |
| 204614_at | NM_002575 | Hs.594481 | SERPINB2 |
| 203747_at | NM_004925 | Hs.234642 | AQP3 |
| 239430_at | AA195677 | Hs.546554 | IGFL1 |
| 216243_s_at | BE563442 | Hs.81134 | IL1RN |
| 230454_at | AI814092 | Hs.501561 | S1PR5 |
| 206008_at | NM_000359 | Hs.508950 | TGM1 |
| 220658_s_at | NM_020183 | Hs.434269 | ARNTL2 |
| 1559606_at | AL703282 | Hs.254338 | GBP6 |
| 204252_at | M68520 | Hs.19192 | CDK2 |
| 211063_s_at | BC006403 | Hs.477693 | NCK1 |
| 217110_s_at | AI242147 | Hs.369646 | MUC4 |
| 220620_at | NM_019060 | Hs.110196 | CRCT1 |
| 205490_x_at | BF060667 | Hs.522561 | GJB3 |
| 222892_at | AI087937 | Hs.475502 | TMEM40 |
| 201528_at | BG398414 | Hs.461925 | RPA1 |
| 208712_at | M73554 | Hs.523852 | CCND1 |
| 204725_s_at | NM_006153 | Hs.477693 | NCK1 |
| 217109_at | AJ242547 | Hs.369646 | MUC4 |
| 227897_at | N20927 | Hs.98643 | RAP2B |
| 209932_s_at | U90223 | Hs.527980 | DUT |
| 206430_at | NM_001804 | Hs.1545 | CDX1 |
| 209847_at | U07969 | Hs.591853 | CDH17 |
| 204272_at | NM_006149 | Hs.5302 | LGALS4 |
| 206387_at | U51096 | Hs.174249 | CDX2 |
| 206418_at | NM_007052 | Hs.592227 | NOX1 |
| 218687_s_at | NM_017648 | Hs.5940 | MUC13 |
| 214070_s_at | AW006935 | Hs.109358 | ATP10B |
| 201884_at | NM_004363 | Hs.709196 | CEACAM5 |
| 213953_at | AI732381 | Hs.84905 | KRT20 |
| 222712_s_at | AW451240 | Hs.5940 | MUC13 |
| 205929_at | NM_005814 | Hs.651244 | GPA33 |
| 207217_s_at | NM_013955 | Hs.592227 | NOX1 |
| 228912_at | AI436136 | Hs.654595 | VIL1 |
| 203903_s_at | NM_014799 | Hs.31720 | HEPH |
| 219404_at | NM_024526 | Hs.485352 | EPS8L3 |
| 207463_x_at | NM_002771 | Hs.654513 | PRSS3 |
| 213421_x_at | AW007273 | Hs.654513 | PRSS3 |
| 202831_at | NM_002083 | Hs.2704 | GPX2 |
| 206312_at | NM_004963 | Hs.524278 | GUCY2C |
| 205506_at | NM_007127 | Hs.654595 | VIL1 |
| 207202_s_at | NM_003889 | Hs.7303 | NR1I2 |
| 206000_at | NM_005588 | Hs.179704 | MEP1A |
| 227867_at | AA005361 | Hs.469134 | LOC129293 |
| 227676_at | AW001287 | Hs.61265 | FAM3D |
| 238143_at | AW001557 | Hs.146268 | LOC646627 |
| 206199_at | NM_006890 | Hs.74466 | CEACAM7 |
| 203824_at | NM_004616 | Hs.170563 | TSPAN8 |
| 210808_s_at | AF166327 | Hs.592227 | NOX1 |
| 226654_at | AF147790 | Hs.489355 | MUC12 |
| 214898_x_at | AB038783 | Hs.489354 | MUC3B |
| 225835_at | AK025062 | Hs.162585 | SLC12A2 |
| 60474_at | AA469071 | Hs.472054 | FERMT1 |
| 238956_at | AA502384 | | |
| 230772_at | AA639753 | | |
| 207380_x_at | NM_013954 | Hs.592227 | NOX1 |
| 218796_at | NM_017671 | Hs.472054 | FERMT1 |
| 219756_at | NM_024921 | Hs.267038 | POF1B |
| 210302_s_at | AF262032 | Hs.584852 | MAB21L2 |
| 240045_at | AI694242 | | |
| 206143_at | NM_000111 | Hs.1650 | SLC26A3 |
| 235334_at | AA552060 | Hs.154578 | MYO7B |
| 239332_at | AW079559 | | |
| 228463_at | R99562 | Hs.36137 | FOXA3 |
| 205632_s_at | NM_003558 | Hs.534371 | PIP5K1B |
| 210107_at | AF127076 | Hs.194659 | CLCA1 |
| 239595_at | AA569032 | Hs.2704 | GPX2 |
| 211883_x_at | M76742 | Hs.512682 | CEACAM1 |
| 207850_at | NM_002090 | Hs.89690 | CXCL3 |
| 215444_s_at | X81006 | Hs.493275 | TRIM31 |
| 211165_x_at | D31661 | Hs.523329 | EPHB2 |
| 206698_at | NM_021083 | Hs.78919 | XK |
| 212925_at | AA143765 | Hs.439180 | C19orf21 |
| 218704_at | NM_017763 | Hs.656319 | RNF43 |
| 201893_at | NM_004052 | Hs.144873 | BNIP3 |
| 211848_s_at | AF006623 | Hs.74466 | CEACAM7 |
| 1561421_a_at | AK057259 | | |
| 229889_at | AW137009 | Hs.25425 | C17orf76 |
| 1555383_a_at | BC017500 | Hs.267038 | POF1B |
| 206286_s_at | NM_003212 | Hs.385870 | TDGF1 |
| 205043_at | NM_000492 | Hs.489786 | CFTR |
| 229215_at | AI393930 | Hs.152475 | ASCL2 |
| 211657_at | U27331 | Hs.631846 | FUT6 |
| 211657_at | M18728 | Hs.466814 | CEACAM6 |
| 227850_x_at | AW084544 | Hs.415791 | CDC42EP5 |
| 205983_at | NM_004413 | Hs.109 | DPEP1 |
| 201328_at | AL575509 | Hs.655628 | ETS2 |
| 206797_at | NM_000015 | Hs.2 | NAT2 |
| 222592_s_at | AW173691 | Hs.11638 | ACSL5 |
| 203757_s_at | BC005008 | Hs.466814 | CEACAM6 |
| 224428_s_at | AY029179 | Hs.470654 | CDCA7 |
| 220645_at | NM_017678 | Hs.179100 | FAM55D |

TABLE 4-continued

List of probes used for tumor origin prediction

| Affymetrix Probe ID | Genbank Accession number | Unigene ID | Gene symbol |
|---|---|---|---|
| 232707_at | AK025181 | Hs.567637 | ISX |
| 221241_s_at | NM_030766 | Hs.210343 | BCL2L14 |
| 207259_at | NM_017928 | Hs.389460 | C17orf73 |
| 207203_s_at | AF061056 | Hs.7303 | NR1I2 |
| 231693_at | AV655991 | Hs.380135 | FABP1 |
| 212768_s_at | AL390736 | Hs.508113 | OLFM4 |
| 211889_x_at | D12502 | Hs.512682 | CEACAM1 |
| 204454_at | NM_012317 | Hs.45231 | LDOC1 |
| 230788_at | BF059748 | Hs.519884 | GCNT2 |
| 223969_s_at | AF323084 | Hs.307047 | RETNLB |
| 205190_at | NM_002670 | Hs.203637 | PLS1 |
| 226226_at | AI282982 | Hs.504301 | TMEM45B |
| 209498_at | X16354 | Hs.512682 | CEACAM1 |
| 231250_at | AI394574 | | |
| 226461_at | AA204719 | Hs.463350 | HOXB9 |
| 204623_at | NM_003226 | Hs.82961 | TFF3 |
| 221879_at | AA886335 | Hs.709550 | CALML4 |
| 201329_s_at | NM_005239 | Hs.655628 | ETS2 |
| 218644_at | NM_016445 | Hs.170473 | PLEK2 |
| 230323_s_at | AW242836 | Hs.504301 | TMEM45B |
| 229777_at | AA863031 | Hs.242014 | CLRN3 |
| 206198_s_at | L31792 | Hs.74466 | CEACAM7 |
| 208170_s_at | NM_007028 | Hs.493275 | TRIM31 |
| 209211_at | AF132818 | Hs.508234 | KLF5 |
| 205932_s_at | NM_002448 | Hs.424414 | MSX1 |
| 230943_at | AI821669 | Hs.98367 | SOX17 |
| 219993_at | NM_022454 | Hs.98367 | SOX17 |
| 213707_s_at | NM_005221 | Hs.99348 | DLX5 |
| 242940_x_at | AA040332 | Hs.249196 | DLX6 |
| 231063_at | AW014518 | | |
| 204086_at | NM_006115 | Hs.30743 | PRAME |
| 241291_at | AI922102 | | |
| 205979_at | NM_002407 | Hs.97644 | SCGB2A1 |
| 228554_at | AL137566 | Hs.32405 | PGR |
| 218857_s_at | NM_025080 | Hs.535326 | ASRGL1 |
| 226424_at | AI683754 | Hs.584744 | CAPS |
| 230882_at | AA129217 | Hs.34969 | FLJ34048 |
| 231729_s_at | NM_004058 | Hs.584744 | CAPS |
| 231728_at | NM_004058 | Hs.584744 | CAPS |
| 222764_at | AI928342 | Hs.535326 | ASRGL1 |
| 205698_s_at | NM_002758 | Hs.463978 | MAP2K6 |
| 203892_at | NM_006103 | Hs.2719 | WFDC2 |
| 203221_at | AI758763 | Hs.197320 | TLE1 |
| 205899_at | NM_003914 | Hs.417050 | CCNA1 |
| 205225_at | NM_000125 | Hs.208124 | ESR1 |
| 229095_s_at | AI797263 | Hs.535619 | LIMS3 |
| 223786_at | AF280086 | Hs.655622 | CHST6 |
| 228815_at | BE645119 | Hs.389311 | MGC13057 |
| 1569361_a_at | BC028018 | Hs.277215 | LOC100129098 |
| 228377_at | AB037805 | Hs.446164 | KLHL14 |
| 231181_at | AI683621 | | |
| 204069_at | NM_002398 | Hs.526754 | MEIS1 |
| 205358_at | NM_000826 | Hs.32763 | GRIA2 |
| 203222_at | NM_005077 | Hs.197320 | TLE1 |
| 208305_at | NM_000926 | Hs.32405 | PGR |
| 209692_at | U71207 | Hs.472877 | EYA2 |
| 221950_at | AI478455 | Hs.202095 | EMX2 |
| 219263_at | NM_024539 | Hs.496542 | RNF128 |
| 205413_at | NM_001584 | Hs.289795 | MPPED2 |
| 229281_at | N51682 | Hs.657892 | NPAS3 |
| 229542_at | AW590326 | Hs.43977 | C20orf85 |
| 230673_at | AV706971 | Hs.170128 | PKHD1L1 |
| 226452_at | AW134979 | Hs.508958 | STXBP6 |
| 222281_s_at | AW517716 | | |
| 227282_at | AB037734 | Hs.4993 | PCDH19 |
| 1553089_a_at | NM_080736 | Hs.2719 | WFDC2 |
| 213917_at | BE465829 | Hs.469728 | PAX8 |
| 242406_at | AI870547 | | |
| 203423_at | NM_002899 | Hs.529571 | RBP1 |
| 231077_at | AI798832 | Hs.534593 | C1orf192 |
| 230412_at | BF196935 | Hs.657892 | NPAS3 |
| 1559477_s_at | AL832770 | Hs.526754 | MEIS1 |
| 203961_at | AL157398 | Hs.5025 | NEBL |
| 236085_at | AI925136 | Hs.55150 | CAPSL |
| 222912_at | BE207758 | Hs.503284 | ARRB1 |
| 228284_at | BE302305 | Hs.197320 | TLE1 |
| 204039_at | NM_004364 | Hs.699463 | CEBPA |
| 203962_s_at | NM_006393 | Hs.5025 | NEBL |
| 240161_s_at | AI470220 | Hs.669184 | CDC20B |
| 204058_at | AL049699 | Hs.21160 | ME1 |
| 203571_s_at | NM_006829 | Hs.642660 | C10orf116 |
| 211671_s_at | U01351 | Hs.122926 | NR3C1 |
| 201865_x_at | AI432196 | Hs.122926 | NR3C1 |
| 201787_at | NM_001996 | Hs.24601 | FBLN1 |
| 230776_at | N59856 | Hs.500643 | RNF157 |
| 206893_at | NM_002968 | Hs.135787 | SALL1 |
| 1553179_at | NM_133638 | Hs.23751 | ADAMTS19 |
| 204059_s_at | NM_002395 | Hs.21160 | ME1 |
| 206022_at | NM_000266 | Hs.522615 | NDP |
| 1561956_at | AF085947 | | |
| 240275_at | AI936559 | Hs.659807 | ARMC3 |
| 229569_at | AW572379 | | |
| 222334_at | AW979289 | | |
| 206191_at | NM_001248 | Hs.441145 | ENTPD3 |
| 229273_at | AU152837 | Hs.135787 | SALL1 |
| 211235_s_at | AF258450 | Hs.208124 | ESR1 |
| 209552_at | BC001060 | Hs.469728 | PAX8 |
| 202628_s_at | NM_000602 | Hs.414795 | SERPINE1 |
| 229096_at | AI797263 | Hs.535619 | LIMS3 |
| 221861_at | AL157484 | | |
| 219764_at | NM_007197 | Hs.31664 | FZD10 |
| 232531_at | AL137578 | Hs.312592 | EMX2OS |
| 216321_s_at | X03348 | Hs.122926 | NR3C1 |
| 201866_s_at | NM_000176 | Hs.122926 | NR3C1 |
| 236538_at | BE219628 | Hs.32763 | GRIA2 |
| 213880_at | AL524520 | Hs.658889 | LGR5 |
| 201092_at | NM_002893 | Hs.495755 | RBBP7 |
| 220316_at | NM_022123 | Hs.657892 | NPAS3 |
| 205906_at | NM_001454 | Hs.651204 | FOXJ1 |
| 205982_x_at | NM_001928 | Hs.155597 | CFD |
| 228035_at | AA453640 | Hs.501833 | STK33 |
| 238206_at | AI089319 | Hs.591686 | RXFP1 |
| 206018_at | NM_005249 | Hs.695962 | FOXG1 |
| 205373_at | NM_004389 | Hs.167368 | CTNNA2 |
| 203021_at | NM_003064 | Hs.517070 | SLPI |
| 226766_at | AB046788 | Hs.13305 | ROBO2 |
| 202965_s_at | NM_014289 | Hs.496593 | CAPN6 |
| 219114_at | NM_004826 | Hs.26880 | ECEL1 |
| 209871_s_at | AB014719 | Hs.618112 | APBA2 |
| 205348_s_at | NM_004411 | Hs.440364 | DYNC1I1 |
| 204009_s_at | W80678 | Hs.505033 | KRAS |
| 214135_at | BE551219 | Hs.655324 | CLDN18 |
| 214476_at | NM_005423 | Hs.2979 | TFF2 |
| 206560_s_at | NM_006533 | Hs.646364 | MIA |
| 206334_at | NM_004190 | Hs.523130 | LIPF |
| 205927_s_at | NM_001910 | Hs.644082 | CTSE |
| 232578_at | BG547464 | Hs.655324 | CLDN18 |
| 214352_s_at | BF673699 | Hs.505033 | KRAS |
| 221133_s_at | NM_016369 | Hs.655324 | CLDN18 |
| 220191_at | NM_019617 | Hs.69319 | GKN1 |
| 221132_at | NM_016369 | Hs.655324 | CLDN18 |
| 219508_at | NM_004751 | Hs.194710 | GCNT3 |
| 206239_s_at | NM_003122 | Hs.407856 | SPINK1 |
| 208126_s_at | NM_000772 | Hs.511872 | CYP2C18 |
| 37433_at | AF077954 | Hs.658013 | PIA52 |
| 215103_at | AW192911 | Hs.511872 | CYP2C18 |
| 204378_at | NM_003657 | Hs.400556 | BCAS1 |
| 233446_at | AU145336 | Hs.194725 | ONECUT2 |
| 1559203_s_at | BC029545 | Hs.505033 | KRAS |
| 238689_at | BG426455 | Hs.256897 | GPR110 |
| 230271_at | BG150301 | Hs.194725 | ONECUT2 |
| 202267_at | NM_005562 | Hs.591484 | LAMC2 |
| 239911_at | H49805 | Hs.194725 | ONECUT2 |
| 224367_at | AF251053 | Hs.398989 | BEX2 |
| 208300_at | NM_002842 | Hs.179770 | PTPRH |
| 224476_s_at | BC006219 | Hs.447531 | MESP1 |
| 230158_at | AA758751 | Hs.533644 | DPY19L2 |
| 240303_at | BG484769 | Hs.115838 | TMC5 |

TABLE 4-continued

List of probes used for tumor origin prediction

| Affymetrix Probe ID | Genbank Accession number | Unigene ID | Gene symbol |
|---|---|---|---|
| 220468_at | NM_025047 | Hs.287702 | ARL14 |
| 204713_s_at | AA910306 | Hs.30054 | F5 |
| 203819_s_at | AU160004 | Hs.700696 | IGF2BP3 |
| 1566764_at | AL359055 | Hs.598388 | 7A5 |
| 230100_x_at | AU147145 | Hs.435714 | PAK1 |
| 219795_at | NM_007231 | Hs.522109 | SLC6A14 |
| 202864_s_at | NM_003113 | Hs.369056 | 5P100 |
| 218468_s_at | AF154054 | Hs.40098 | GREM1 |
| 219014_at | NM_016619 | Hs.546392 | PLAC8 |
| 204855_at | NM_002639 | Hs.55279 | SERPINB5 |
| 202652_at | NM_001164 | Hs.372840 | APBB1 |
| 202068_s_at | NM_000527 | Hs.213289 | LDLR |
| 219429_at | NM_024306 | Hs.461329 | FA2H |
| 243409_at | AI005407 | Hs.533830 | FOXL1 |
| 206515_at | NM_000896 | Hs.106242 | CYP4F3 |
| 204537_s_at | NM_004961 | Hs.22785 | GABRE |
| 229030_at | AW242997 | Hs.291487 | CAPN8 |
| 204714_s_at | NM_000130 | Hs.30054 | F5 |
| 218469_at | NM_013372 | Hs.40098 | GREM1 |
| 210159_s_at | AF230386 | Hs.493275 | TRIM31 |
| 231029_at | AI740541 | Hs.30054 | F5 |
| 209939_x_at | AF005775 | Hs.390736 | CFLAR |
| 223694_at | AF220032 | Hs.487412 | TRIM7 |
| 1556116_s_at | AI825808 | Hs.482497 | TNPO1 |
| 205402_x_at | NM_002770 | Hs.622865 | PRSS2 |
| 212444_at | AA156240 | | |
| 212287_at | BF382924 | Hs.462732 | SUZ12 |
| 204678_s_at | U90065 | Hs.208544 | KCNK1 |
| 203964_at | NM_004688 | Hs.54483 | NMI |
| 214993_at | AF070642 | Hs.655761 | ASPHD1 |
| 216470_x_at | AF009664 | | LOC100134294 |
| 219580_s_at | NM_024780 | Hs.115838 | TMC5 |
| 210002_at | D87811 | Hs.514746 | GATA6 |
| 222904_s_at | AW469181 | Hs.115838 | TMC5 |
| 201468_s_at | NM_000903 | Hs.406515 | NQO1 |
| 209270_at | L25541 | Hs.497636 | LAMB3 |
| 203108_at | NM_003979 | Hs.631733 | GPRC5A |
| 218806_s_at | AF118887 | Hs.267659 | VAV3 |
| 206884_s_at | NM_003843 | Hs.534699 | SCEL |
| 205261_at | NM_002630 | Hs.1867 | PGC |
| 224590_at | BE644917 | Hs.529901 | XIST |
| 209310_s_at | U25804 | Hs.138378 | CASP4 |
| 227733_at | AA928939 | Hs.593722 | TMEM63C |
| 209368_at | AF233336 | Hs.212088 | EPHX2 |
| 210563_x_at | U97075 | Hs.390736 | CFLAR |
| 232151_at | AL359055 | Hs.598388 | 7A5 |
| 208505_s_at | NM_000511 | Hs.579928 | FUT2 |
| 205185_at | NM_006846 | Hs.331555 | SPINK5 |
| 236163_at | AW136983 | Hs.656702 | LIX1 |
| 230865_at | N29837 | Hs.656702 | LIX1 |
| 227426_at | AV702692 | Hs.709893 | SOS1 |
| 237810_at | AW003929 | Hs.533779 | CLDN6 |
| 208235_x_at | NM_021123 | Hs.460641 | GAGE7 |
| 205122_at | BF439316 | Hs.598100 | TMEFF1 |
| 206067_s_at | NM_024426 | Hs.591980 | WT1 |
| 231192_at | AW274018 | | |
| 207739_s_at | NM_001472 | Hs.658117 | GAGE2C |
| 207663_x_at | NM_001473 | | GAGE3 |
| 212780_at | AA700167 | Hs.709893 | SOS1 |
| 1554460_at | BC027866 | Hs.308628 | ST8SIA4 |
| 216953_at | S75264 | Hs.591980 | WT1 |
| 206179_s_at | NM_007030 | Hs.481466 | TPPP |
| 205177_at | NM_003281 | Hs.320890 | TNNI1 |
| 208775_at | D89729 | Hs.370770 | XPO1 |
| 209486_at | AB018305 | Hs.705394 | SPON1 |
| 206249_at | NM_004721 | Hs.656069 | MAP3K13 |
| 229221_at | BE467023 | Hs.502328 | CD44 |
| 213294_at | AV755522 | Hs.131431 | EIF2AK2 |
| 205901_at | NM_088218 | Hs.88218 | PNOC |
| 206439_at | NM_004950 | Hs.435680 | EPYC |
| 220816_at | NM_012152 | Hs.674915 | LPAR3 |
| 210248_at | D83175 | Hs.72290 | WNT7A |
| 213993_at | AI885290 | Hs.705394 | SPON1 |
| 206935_at | NM_002590 | Hs.19492 | PCDH8 |
| 202097_at | NM_005124 | Hs.601591 | NUP153 |
| 215987_at | AV654984 | Hs.113912 | RAPGEF2 |
| 212909_at | AL567376 | Hs.714802 | LYPD1 |
| 210263_at | AF029780 | Hs.23735 | KCNF1 |
| 1562981_at | AY034472 | Hs.523443 | HBB |
| 204437_s_at | NM_016725 | Hs.73769 | FOLR1 |
| 214219_x_at | BE646618 | Hs.95424 | MAP4K1 |
| 235205_at | BF109660 | Hs.127286 | LOC100128259 |
| 215447_at | AL080215 | Hs.516578 | TFPI |
| 213994_s_at | AI885290 | Hs.705394 | SPON1 |
| 1559239_s_at | AW750026 | Hs.232375 | ACAT1 |
| 207086_x_at | NM_001474 | Hs.460641 | GAGE4 |
| 213201_s_at | AJ011712 | Hs.631558 | TNNT1 |
| 217558_at | BE971373 | Hs.282624 | CYP2C9 |
| 208477_at | NM_004976 | Hs.552896 | KCNC1 |
| 233944_at | AU147118 | | |
| 1552742_at | NM_144633 | Hs.475656 | KCNH8 |
| 211585_at | U58852 | Hs.171061 | NPAT |
| 204930_at | NM_000170 | Hs.584238 | GLDC |
| 218309_at | NM_018584 | Hs.197922 | CAMK2N1 |
| 239381_at | AU155415 | Hs.151254 | KLK7 |
| 234719_at | AK024889 | Hs.436367 | LAMA3 |
| 222242_s_at | AF243527 | Hs.50915 | KLK5 |
| 205473_at | NM_001692 | Hs.64173 | ATP6V181 |
| 207010_at | NM_000812 | Hs.27283 | GABRB1 |
| 210446_at | M30601 | Hs.765 | GATA1 |
| 204777_s_at | NM_002371 | Hs.80395 | MAL |
| 214598_at | AL049977 | Hs.162209 | CLDN8 |
| 203844_at | NM_000551 | Hs.517792 | VHL |
| 222103_at | AI434345 | Hs.648565 | ATF1 |
| 222023_at | AK022014 | Hs.459211 | AKAP13 |
| 242266_x_at | AW973803 | | |
| 235700_at | AI581344 | Hs.535080 | RP13-36C9.3 |
| 229163_at | N75559 | Hs.197922 | CAMK2N1 |
| 225482_at | AL533416 | Hs.516802 | KIF1A |
| 243489_at | BF514098 | | |
| 204456_s_at | AW611727 | Hs.65029 | GAS1 |
| 224488_s_at | BC006262 | Hs.705394 | SPON1 |
| 216056_at | AW851559 | Hs.502328 | CD44 |
| 203876_s_at | AI761713 | Hs.143751 | MMP11 |
| 206586_at | NM_001841 | Hs.73037 | CNR2 |
| 205778_at | NM_005046 | Hs.151254 | KLK7 |
| 214053_at | AW772192 | Hs.390729 | ERBB4 |
| 222861_s_at | NM_012168 | Hs.132753 | FBXO2 |
| 238698_at | AI659225 | Hs.495984 | CASK |
| 213609_s_at | AB023144 | Hs.194766 | SEZ6L |
| 206023_at | NM_006681 | Hs.418367 | NMU |
| 223467_at | AF069506 | Hs.25829 | RASD1 |
| 217133_x_at | X06399 | Hs.1360 | CYP2B6 |
| 227318_at | AL359605 | | |
| 227952_at | AI580142 | | |
| 208198_x_at | NM_014512 | Hs.661101 | KIR2DS1 |
| 206803_at | NM_024411 | Hs.22584 | PDYN |
| 238584_at | W52934 | Hs.591594 | IQCA1 |
| 224482_s_at | BC006240 | Hs.406788 | RA811FIP4 |
| 211029_x_at | BC006245 | Hs.87191 | FGF18 |
| 1553169_at | BC019612 | Hs.149133 | LRRN4 |
| 1552575_a_at | NM_153344 | Hs.485528 | C6orf141 |
| 209757_s_at | BC002712 | Hs.25960 | MYCN |
| 207004_at | NM_000657 | Hs.150749 | BCL2 |
| 231489_x_at | H12214 | | |
| 216261_at | AI151479 | Hs.218040 | ITGB3 |
| 213150_at | BF792917 | Hs.592166 | HOXA10 |
| 230835_at | W69083 | Hs.112457 | KRTDAP |
| 204630_s_at | NM_000494 | Hs.117938 | COL17A1 |
| 216918_s_at | AL096710 | Hs.631992 | DST |
| 204455_at | NM_001723 | Hs.631992 | DST |
| 209888_s_at | M20643 | Hs.187338 | MYL1 |
| 214599_at | NM_005547 | Hs.516439 | IVL |
| 203872_at | NM_001100 | Hs.1288 | ACTA1 |
| 224329_s_at | AB049591 | Hs.148590 | CNFN |
| 208195_at | NM_003319 | Hs.134602 | TTN |
| 209742_s_at | AF020768 | Hs.75535 | MYL2 |
| 205951_at | NM_005963 | Hs.689619 | MYH1 |

TABLE 4-continued

List of probes used for tumor origin prediction

| Affymetrix Probe ID | Genbank Accession number | Unigene ID | Gene symbol |
|---|---|---|---|
| 204810_s_at | NM_001824 | Hs.334347 | CKM |
| 209351_at | BC002690 | Hs.654380 | KRT14 |
| 235272_at | AI814274 | Hs.433484 | SBSN |
| 204734_at | NM_002275 | Hs.654570 | KRT15 |
| 213385_at | AK026415 | Hs.654611 | CHN2 |
| 204631_at | NM_017534 | Hs.699445 | MYH2 |
| 220414_at | NM_017422 | Hs.180142 | CALML5 |
| 1556773_at | M31157 | | |
| 1564307_a_at | AL832750 | Hs.620532 | A2ML1 |
| 219106_s_at | NM_006063 | Hs.50550 | KBTBD10 |
| 218689_at | NM_022725 | Hs.713574 | FANCF |
| 219995_s_at | NM_024702 | Hs.653124 | ZNF750 |
| 228794_at | AA211780 | Hs.73680 | XIRP2 |
| 236119_s_at | AA456642 | Hs.490253 | SPRR2G |
| 205485_at | NM_000540 | Hs.466664 | RYR1 |
| 231331_at | AI085377 | | |
| 231771_at | AI694073 | Hs.511757 | GJB6 |
| 221577_x_at | AP003934 | Hs.616962 | GDF15 |
| 206912_at | NM_004473 | Hs.159234 | FOXE1 |
| 203861_s_at | AU146889 | Hs.498178 | ACTN2 |
| 238657_at | T86344 | Hs.432503 | UBXN10 |
| 232202_at | AK024927 | | |
| 205444_at | NM_004320 | Hs.657344 | ATP2A1 |
| 205820_s_at | NM_000040 | Hs.73849 | APOC3 |
| 219465_at | NM_001643 | Hs.237658 | APOA2 |
| 1565228_s_at | D16931 | Hs.418167 | ALB |
| 205477_s_at | NM_001633 | Hs.436911 | AMBP |
| 37020_at | X56692 | Hs.76452 | CRP |
| 219466_s_at | NM_001643 | Hs.237658 | APOA2 |
| 206287_s_at | NM_002218 | Hs.709406 | ITIH4 |
| 206226_at | NM_000412 | Hs.1498 | HRG |
| 205755_at | NM_002217 | Hs.76716 | ITIH3 |
| 206177_s_at | NM_000045 | Hs.440934 | ARG1 |
| 204987_at | NM_002216 | Hs.75285 | ITIH2 |
| 204534_at | NM_000638 | Hs.2257 | VTN |
| 1554491_a_at | BC022309 | Hs.75599 | SERPINC1 |
| 205813_s_at | NM_000429 | Hs.282670 | MAT1A |
| 1431_at | J02843 | Hs.12907 | CYP2E1 |
| 205754_at | NM_000506 | Hs.655207 | F2 |
| 204551_s_at | NM_001622 | Hs.324746 | AHSG |
| 205649_s_at | NM_000508 | Hs.351593 | FGA |
| 205500_at | NM_001735 | Hs.494997 | C5 |
| 206651_s_at | NM_016413 | Hs.512937 | CPB2 |
| 205216_s_at | NM_000042 | Hs.445358 | APOH |
| 206054_at | NM_000893 | Hs.77741 | KNG1 |
| 210013_at | BC005395 | Hs.426485 | HPX |
| 205108_s_at | NM_000384 | Hs.120759 | APOB |
| 204965_at | NM_000583 | Hs.418497 | GC |
| 206292_s_at | NM_003167 | Hs.515835 | SULT2A1 |
| 211298_s_at | AF116645 | Hs.418167 | AL8 |
| 210929_s_at | AF130057 | Hs.621361 | LOC100131613 |
| 210888_s_at | AF116713 | Hs.420257 | ITIH1 |
| 207218_at | NM_000133 | Hs.522798 | F9 |
| 210327_s_at | D13368 | Hs.144567 | AGXT |
| 209975_at | AF182276 | Hs.12907 | CYP2E1 |
| 206727_at | K02766 | Hs.654443 | C9 |
| 214465_at | NM_000608 | Hs.714720 | ORM2 |
| 206293_at | U08024 | Hs.515835 | SULT2A1 |
| 205040_at | NM_000607 | Hs.522356 | ORM1 |
| 205576_at | NM_000185 | Hs.474270 | SERPIND1 |
| 209978_at | M74220 | Hs.143436 | PLG |
| 210798_x_at | AB008047 | Hs.655645 | MASP2 |
| 217512_at | BG398937 | Hs.77741 | KNG1 |
| 209976_s_at | AF182276 | Hs.12907 | CYP2E1 |
| 210215_at | AF067864 | Hs.544932 | TFR2 |
| 206130_s_at | NM_001181 | Hs.654440 | ASGR2 |
| 205650_s_at | NM_021871 | Hs.351593 | FGA |
| 231678_s_at | AV651117 | Hs.1219 | ADH4 |
| 205753_at | NM_000567 | Hs.76452 | CRP |
| 206979_at | NM_000066 | Hs.391835 | C8B |
| 208147_s_at | NM_030878 | Hs.709188 | CYP2C8 |
| 209977_at | M74220 | Hs.143436 | PLG |
| 216238_s_at | BG545288 | Hs.300774 | FGB |
| 219803_at | NM_014495 | Hs.209153 | ANGPTL3 |
| 209660_at | AF162690 | Hs.427202 | TTR |
| 214421_x_at | AV652420 | Hs.282624 | CYP2C9 |
| 223579_s_at | AF119905 | Hs.120759 | APOB |
| 216025_x_at | M21940 | Hs.282624 | CYP2C9 |
| 205041_s_at | NM_000607 | Hs.522356 | ORM1 |
| 237530_at | T77543 | | |
| 240033_at | BF447999 | Hs.143436 | PLG |
| 207200_at | NM_000531 | Hs.117050 | OTC |
| 205302_at | NM_000596 | Hs.642938 | IGFBP1 |
| 216661_x_at | M15331 | Hs.282624 | CYP2C9 |
| 217073_x_at | X02162 | Hs.633003 | APOA1 |
| 206913_at | NM_001701 | Hs.284712 | BAAT |
| 228621_at | AA948096 | Hs.632436 | HFE2 |
| 204450_x_at | NM_000039 | Hs.633003 | APOA1 |
| 204561_x_at | NM_000483 | Hs.75615 | APOC2 |
| 210326_at | D13368 | Hs.144567 | AGXT |
| 208471_at | NM_020995 | Hs.655361 | HPR |
| 204988_at | NM_005141 | Hs.300774 | FGB |
| 219612_s_at | NM_000509 | Hs.546255 | FGG |
| 208367_x_at | NM_000776 | Hs.654391 | CYP3A4 |
| 206743_s_at | NM_001671 | Hs.12056 | ASGR1 |
| 214063_s_at | AI073407 | Hs.518267 | TF |
| 231398_at | AA777852 | Hs.485438 | SLC22A7 |
| 220224_at | NM_017545 | Hs.193640 | HAO1 |
| 203400_s_at | NM_001063 | Hs.518267 | TF |
| 214842_s_at | M12523 | Hs.418167 | ALB |
| 207640_at | NM_000780 | Hs.1644 | CYP7A1 |
| 205152_at | AI003579 | Hs.443874 | SLC6A1 |
| 207392_x_at | NM_001076 | Hs.150207 | UGT2B15 |
| 207256_at | NM_000242 | Hs.499674 | MBL2 |
| 205719_s_at | NM_000277 | Hs.643451 | PAH |
| 1554459_s_at | BC020687 | Hs.709217 | CFHR3 |
| 203179_at | NM_000155 | Hs.522090 | GALT |
| 217564_s_at | W80357 | Hs.149252 | CPS1 |
| 210587_at | BC005161 | Hs.632713 | INH8E |
| 216687_x_at | U06641 | Hs.150207 | UGT2B15 |
| 208209_s_at | NM_000716 | Hs.99886 | C4BPB |
| 207858_s_at | NM_000298 | Hs.95990 | PKLR |
| 242817_at | BE672390 | Hs.282244 | PGLYRP2 |
| 205727_at | NM_006841 | Hs.76460 | SLC38A3 |
| 206259_at | NM_000312 | Hs.224698 | PROC |
| 205675_at | AI623321 | Hs.195799 | MTTP |
| 230318_at | T62088 | Hs.525557 | SERPINA1 |
| 213800_at | X04697 | Hs.363396 | CFH |
| 215388_s_at | X56210 | Hs.575869 | CFHR1 |
| 220017_x_at | NM_000771 | Hs.282624 | CYP2C9 |
| 207819_s_at | NM_000443 | Hs.654403 | ABCB4 |
| 211735_x_at | NM_003018 | Hs.1074 | SFTPC |
| 211735_x_at | BC005913 | Hs.1074 | SFTPC |
| 214387_x_at | AA633841 | Hs.1074 | SFTPC |
| 37004_at | J02761 | Hs.512690 | SFTPB |
| 38691_s_at | J03553 | Hs.1074 | SFTPC |
| 209810_at | J02761 | Hs.512690 | SFTPB |
| 218835_at | NM_006926 | Hs.523084 | SFTPA28 |
| 223678_s_at | M13685 | Hs.523084 | SFTPA18 |
| 214199_at | NM_003019 | Hs.253495 | SFTPD |
| 223680_s_at | AF090586 | Hs.714418 | NAPSA |
| 228979_at | BE218152 | Hs.509165 | SFTA3 |
| 211024_s_at | BC006221 | Hs.705388 | NKX2-1 |
| 210068_s_at | U63622 | Hs.315369 | AQP4 |
| 244056_at | AW293443 | Hs.211267 | SFTA2 |
| 231315_at | AI807728 | | |
| 205725_at | NM_003357 | Hs.523732 | SCGB1A1 |
| 215454_x_at | AI831055 | Hs.1074 | SFTPC |
| 230378_at | AA742697 | Hs.62492 | SCGB3A1 |
| 210906_x_at | U34846 | Hs.315369 | AQP4 |
| 205654_at | NM_000715 | Hs.1012 | C4BPA |
| 243818_at | T96555 | Hs.31562 | SFTA1P |
| 226742_at | AW471176 | Hs.445586 | CXCL17 |
| 220542_s_at | NM_016583 | Hs.211092 | PLUNC |
| 230319_at | AI222435 | | |
| 226067_at | AL355392 | Hs.65551 | C20orf114 |
| 1566140_at | AK096707 | Hs.654864 | HOPX |
| 215059_at | AA053967 | | |

TABLE 4-continued

List of probes used for tumor origin prediction

| Affymetrix Probe ID | Genbank Accession number | Unigene ID | Gene symbol |
|---|---|---|---|
| 220057_at | NM_020411 | Hs.112208 | XAGE1D |
| 229177_at | AI823572 | Hs.11782 | C16orf89 |
| 204124_at | AF146796 | Hs.479372 | SLC34A2 |
| 227848_at | AI218954 | Hs.491242 | PEBP4 |
| 209616_s_at | 573751 | Hs.558865 | CES1 |
| 240242_at | BE222843 | | |
| 213695_at | L48516 | Hs.440967 | PON3 |
| 232765_x_at | AI985918 | Hs.447544 | LOC146429 |
| 217625_at | BF508244 | Hs.460260 | AKR1C2 |
| 205819_at | NM_006770 | Hs.67726 | MARCO |
| 213674_x_at | AI858004 | Hs.510635 | IGHG1 |
| 202637_s_at | AI608725 | Hs.707983 | ICAM1 |
| 234366_x_at | AF103591 | Hs.449585 | IGL@ |
| 1555236_a_at | BC042578 | Hs.1867 | PGC |
| 204424_s_at | AL050192 | Hs.504908 | LMO3 |
| 230867_at | AI742521 | Hs.591282 | COL6A6 |
| 202638_at | NM_000201 | Hs.707983 | ICAM1 |
| 210673_x_at | D50740 | Hs.705388 | NKX2-1 |
| 215621_s_at | BG340670 | Hs.510635 | IGHG1 |
| 215946_x_at | AL022324 | Hs.567636 | IGLL3 |
| 219434_at | NM_018643 | Hs.283022 | TREM1 |
| 210216_x_at | AF084513 | Hs.531879 | RAD1 |
| 1555854_at | AA594609 | | |
| 238017_at | AI440266 | Hs.170673 | RDHE2 |
| 235568_at | BF433657 | Hs.709539 | C19orf59 |
| 204811_s_at | NM_006030 | Hs.476273 | CACNA2D2 |
| 217227_x_at | X93006 | Hs.449585 | IGL@ |
| 204460_s_at | AF074717 | Hs.531879 | RAD1 |
| 216594_x_at | S68290 | Hs.460260 | AKR1C1 |
| 204151_x_at | NM_001353 | Hs.460260 | AKR1C1 |
| 228504_at | AI828648 | | |
| 211653_x_at | M33376 | Hs.460260 | AKR1C2 |
| 209924_at | AB000221 | Hs.143961 | CCL18 |
| 234350_at | AF127125 | Hs.449585 | IGLV3-21 |
| 1553605_a_at | NM_152701 | Hs.226568 | ABCA13 |
| 224342_x_at | L14452 | Hs.449585 | IGL@ |
| 209441_at | AY009093 | Hs.372688 | RHOBTB2 |
| 217258_x_at | AF043583 | Hs.449599 | IVD |
| 214651_s_at | U41813 | Hs.659350 | HOXA9 |
| 209699_x_at | U05598 | Hs.460260 | AKR1C2 |
| 216430_x_at | AF043586 | Hs.449585 | IGL@ |
| 217480_x_at | M20812 | Hs.449972 | LOC339562 |
| 217179_x_at | X79782 | | |
| 209905_at | AI246769 | Hs.659350 | HOXA9 |
| 204081_at | NM_006176 | Hs.524116 | NRGN |
| 205866_at | NM_003665 | Hs.333383 | FCN3 |
| 211881_x_at | AB014341 | Hs.449585 | IGLl3 |
| 205623_at | NM_000691 | Hs.531682 | ALDH3A1 |
| 32128_at | Y13710 | Hs.143961 | CCL18 |
| 216412_x_at | AP043584 | Hs.449599 | IVD |
| 205430_at | AL133386 | Hs.296648 | BMP5 |
| 220393_at | NM_016571 | Hs.149585 | GLULD1 |
| 217157_x_at | AF103530 | Hs.449621 | IGKC |
| 210096_at | J02871 | Hs.436317 | CYP4B1 |
| 1553413_at | NM_025011 | | FLJ13744 |
| 215214_at | HS3689 | Hs.449585 | IGL@ |
| 203279_at | NM_014674 | Hs.224616 | EDEM1 |
| 208168_s_at | NM_003465 | Hs.201688 | CHIT1 |
| 232056_at | AW470178 | Hs.534699 | SCEL |
| 227168_at | BF475488 | Hs.653712 | MIAT |
| 203159_at | NM_014905 | Hs.116448 | GLS |
| 204844_at | L12468 | Hs.435765 | ENPEP |
| 204845_s_at | NM_001977 | Hs.435765 | ENPEP |
| 205670_at | NM_004861 | Hs.17958 | GAL3ST1 |
| 205674_x_at | NM_001680 | Hs.413137 | FXYD2 |
| 205799_s_at | M95548 | Hs.112916 | SLC3A1 |
| 206119_at | NM_001713 | Hs.80756 | BHMT |
| 206963_s_at | NM_016347 | Hs.458287 | NAT83 |
| 207298_at | NM_006632 | Hs.327179 | SLC17A3 |
| 207429_at | NM_003058 | Hs.436385 | SLC22A2 |
| 207434_s_at | NM_021603 | Hs.413137 | FXYD2 |
| 210289_at | AB013094 | Hs.14637 | NAT8 |
| 214069_at | AA865601 | Hs.298252 | ACSM2B |
| 222071_s_at | BE552428 | Hs.127648 | SLCO4C1 |
| 223784_at | AF229179 | Hs.129614 | TMEM27 |
| 228780_at | AW149422 | | |
| 230184_at | AL035834 | | |
| 230554_at | AV695234 | Hs.298252 | ACSM2B |
| 237058_x_at | AI802118 | Hs.504398 | SLC6A13 |
| 237328_at | AI927063 | | |
| 230920_at | BF060736 | Hs.61504 | LOC284542 |
| 220084_at | NM_018168 | Hs.659706 | C14orf105 |
| 241914_s_at | AA804293 | Hs.298252 | ACSM2B |
| 219902_at | NM_017614 | Hs.114172 | BHMT2 |
| 231790_at | AA676742 | Hs.655653 | DMGDH |
| 223820_at | AY007436 | Hs.714875 | RBP5 |
| 219564_at | NM_018658 | Hs.463985 | KCNJ16 |
| 230602_at | AW025340 | Hs.655728 | ACMSD |
| 206517_at | NM_004062 | Hs.513660 | CDH16 |
| 230309_at | BE876610 | | |
| 203157_s_at | AB020645 | Hs.116448 | GLS |
| 222943_at | AW235567 | Hs.653107 | GBA3 |
| 235774_at | AV699047 | Hs.597380 | LOC553137 |
| 205978_at | NM_004795 | Hs.524953 | KL |
| 231187_at | AI206039 | Hs.459187 | SLC28A1 |
| 205380_at | NM_002614 | Hs.444751 | PDZK1 |
| 206340_at | NM_005123 | Hs.282735 | NR1H4 |
| 228367_at | BE551416 | Hs.656805 | ALPK2 |
| 219954_s_at | NM_020973 | Hs.653107 | GBA3 |
| 224179_s_at | AF230095 | Hs.129227 | MIOX |
| 222083_at | AW024233 | Hs.145384 | GLYAT |
| 1554375_a_at | AF478446 | Hs.282735 | NR1H4 |
| 230432_at | AI733124 | Hs.597380 | LOC553137 |
| 220148_at | NM_022568 | Hs.486520 | ALDH8A1 |
| 244567_at | BG165613 | | |
| 1557921_s_at | BC013914 | | |
| 205234_at | NM_004696 | Hs.351306 | SLC16A4 |
| 239707_at | BF510408 | Hs.462418 | SLC5A10 |
| 206228_at | AW769732 | Hs.155644 | PAX2 |
| 237017_s_at | T73002 | | |
| 244044_at | AV691872 | | |
| 223610_at | BC002776 | Hs.210870 | SEMA5B |
| 229168_at | AI690433 | Hs.660026 | COL23A1 |
| 230022_at | BF057185 | Hs.592064 | LOC348174 |
| 229229_at | AJ292204 | Hs.34494 | AGXT2 |
| 206775_at | NM_001081 | Hs.166206 | CUBN |
| 206065_s_at | NM_001385 | Hs.443161 | DPYS |
| 205532_s_at | AU151483 | Hs.171054 | CDH6 |
| 219271_at | NM_024572 | Hs.468058 | GALNT14 |
| 222938_x_at | AI685421 | Hs.486489 | ENPP3 |
| 239667_at | AW000967 | Hs.112916 | SLC3A1 |
| 207052_at | NM_012206 | Hs.129711 | HAVCR1 |
| 202950_at | NM_001889 | Hs.83114 | CRYZ |
| 214803_at | BF344237 | | |
| 209283_at | AF007162 | Hs.408767 | CRYAB |
| 205893_at | NM_014932 | Hs.478289 | NLGN1 |
| 206836_at | NM_001044 | Hs.406 | SLC6A3 |
| 203868_s_at | NM_001078 | Hs.109225 | VCAM1 |
| 218484_at | NM_020142 | Hs.75069 | NDUFA4L2 |
| 225558_at | R38084 | Hs.434996 | GIT2 |
| 218353_at | NM_025226 | Hs.24950 | RGS5 |
| 206030_at | NM_000049 | Hs.171142 | ASPA |
| 239860_at | AI311917 | Hs.656046 | LOC100130232 |
| 240253_at | BF508634 | | |
| 203167_at | AI139413 | Hs.644739 | CYS1 |
| 205363_at | NM_003986 | Hs.591996 | BBOX1 |
| 221009_s_at | NM_016109 | Hs.9613 | ANGPTL4 |
| 232737_s_at | AL157377 | Hs.486489 | ENPP3 |
| 220233_at | NM_024907 | Hs.531770 | FBXO17 |
| 236860_at | BF968482 | Hs.643466 | NPY6R |
| 205710_at | NM_004525 | Hs.657729 | LRP2 |
| 219948_x_at | NM_024743 | Hs.122583 | UGT2A3 |
| 244122_at | AW291482 | Hs.576171 | LOC388630 |
| 203158_s_at | AF097493 | Hs.116448 | GLS |
| 209122_at | BC005127 | Hs.3416 | ADFP |
| 205222_at | NM_001966 | Hs.429879 | EHHADH |
| 243168_at | AI916532 | | |
| 214091_s_at | AW149846 | Hs.386793 | GPX3 |

TABLE 4-continued

List of probes used for tumor origin prediction

| Affymetrix Probe ID | Genbank Accession number | Unigene ID | Gene symbol |
|---|---|---|---|
| 216733_s_at | X86401 | Hs.75335 | GATM |
| 219121_s_at | NM_017697 | Hs.487471 | RBM35A |
| 237351_at | AI732190 | | |
| 230863_at | R73030 | Hs.657729 | LRP2 |
| 220502_s_at | NM_022444 | Hs.489849 | SLC13A1 |
| 225846_at | BF001941 | Hs.487471 | RBM35A |
| 244723_at | BF510430 | Hs.656497 | LOC100129488 |
| 242169_at | AA703201 | Hs.114172 | BHMT2 |
| 226498_at | AA149648 | | |
| 215244_at | AI479306 | Hs.646438 | DGCR5 |
| 220100_at | NM_018484 | Hs.220844 | SLC22A11 |
| 207738_s_at | NM_013436 | Hs.603732 | NCKAP1 |
| 200765_x_at | NM_001903 | Hs.534797 | CTNNA1 |
| 201059_at | NM_005231 | Hs.596164 | CTTN |
| 210844_x_at | D14705 | Hs.534797 | CTNNA1 |
| 224813_at | AL523820 | Hs.143728 | WASL |
| 205417_s_at | NM_004393 | Hs.76111 | DAG1 |
| 200602_at | NM_000484 | Hs.434980 | APP |
| 205297_s_at | NM_000626 | Hs.89575 | CD79B |
| 200764_s_at | AI826881 | Hs.534797 | CTNNA1 |
| 228592_at | AW474852 | Hs.712553 | MS4A1 |
| 218311_at | NM_003618 | Hs.655750 | MAP4K3 |
| 1555779_a_at | M74721 | Hs.631567 | CD79A |
| 205861_at | NM_003121 | Hs.437905 | SPIB |
| 206255_at | NM_001715 | Hs.146591 | BLK |
| 224861_at | AA628423 | Hs.269782 | GNAQ |
| 202329_at | NM_004383 | Hs.77793 | CSK |
| 235400_at | AL560266 | Hs.266331 | FCRLA |
| 230805_at | AA749202 | | |
| 226216_at | W84556 | Hs.465744 | INSR |
| 200606_at | NM_004415 | Hs.519873 | DSP |
| 207069_s_at | NM_005585 | Hs.153863 | SMAD5 |
| 223751_x_at | AF296673 | Hs.120551 | TLR10 |
| 201286_at | Z48199 | Hs.224607 | SDC1 |
| 208820_at | AL037339 | Hs.395482 | PTK2 |
| 214953_at | X06989 | Hs.434980 | APP |
| 220059_at | NM012108 | Hs.435579 | STAP1 |
| 204192_at | NM_001774 | Hs.166556 | CD37 |
| 224891_at | AV725666 | Hs.220950 | FOXO3 |
| 209685_s_at | M13975 | Hs.460355 | PRKCB |
| 206398_s_at | NM_001770 | Hs.652262 | CD19 |
| 209995_s_at | BC003574 | Hs.2484 | TCL1A |
| 564_at | M69013 | Hs.650575 | GNA11 |
| 206687_s_at | NM_002831 | Hs.63489 | PTPN6 |
| 214339_s_at | AA744529 | Hs.95424 | MAP4K1 |
| 213766_x_at | N36926 | Hs.650575 | GNA11 |
| 202615_at | BF222895 | Hs.269782 | GNAQ |
| 204960_at | NM_005608 | Hs.155795 | PTPRCAP |
| 218261_at | NM_005498 | Hs.18894 | AP1M2 |
| 227522_at | AA209487 | Hs.192586 | CMBL |
| 209827_s_at | NM_004513 | Hs.459095 | IL16 |
| 208731_at | AU158062 | Hs.369017 | RAB2A |
| 208683_at | M23254 | Hs.350899 | CAPN2 |
| 227336_at | AW576405 | Hs.372152 | DTX1 |
| 210448_s_at | U49396 | Hs.408615 | P2RX5 |
| 224862_at | BF969428 | Hs.269782 | GNAQ |
| 204581_at | NM_001771 | Hs.709215 | CD22 |
| 205606_at | NM_002336 | Hs.584775 | LRP6 |
| 205213_at | NM_014716 | Hs.337242 | CENTB1 |
| 206385_s_at | NM_020987 | Hs.499725 | ANK3 |
| 212588_at | Y00062 | Hs.654514 | PTPRC |
| 201242_s_at | BC000006 | Hs.291196 | ATP1B1 |
| 205049_s_at | NM_001783 | Hs.631567 | CD79A |
| 224499_s_at | BC006296 | Hs.149342 | AICDA |
| 206296_x_at | NM_007181 | Hs.95424 | MAP4K1 |
| 212587_s_at | AI809341 | Hs.654514 | PTPRC |
| 223750_s_at | AW665250 | Hs.120551 | TLR10 |
| 205267_at | NM_006235 | Hs.654525 | POU2AF1 |
| 205809_s_at | BE504979 | Hs.143728 | WASL |
| 230980_x_at | AI307713 | | |
| 227030_at | BF231773 | | |
| 225745_at | AV725248 | Hs.584775 | LRP6 |
| 217422_s_at | X52785 | Hs.709215 | CD22 |
| 228494_at | AI888150 | Hs.21816 | PPP1R9A |
| 214679_at | AL110227 | Hs.650575 | GNA11 |
| 204661_at | NM_001803 | Hs.276770 | CD52 |
| 207957_s_at | NM_002738 | Hs.460355 | PRKCB |
| 201428_at | NM_001305 | Hs.647036 | CLDN4 |
| 201650_at | NM_002276 | Hs.654568 | KRT19 |
| 205544_s_at | NM_001877 | Hs.445757 | CR2 |
| 40562_at | AF011499 | Hs.650575 | GNA11 |
| 228051_at | AI979261 | Hs.194408 | LOC202451 |
| 34210_at | N90866 | Hs.276770 | CD52 |
| 211945_s_at | BG500301 | Hs.713531 | ITGB1 |
| 228188_at | AI860150 | Hs.220971 | FOSL2 |
| 213944_x_at | BG236220 | Hs.650575 | GNA11 |
| 209135_at | AF289489 | Hs.622998 | ASPH |
| 204248_at | NM_002067 | Hs.650575 | GNA11 |
| 212285_s_at | AW008051 | Hs.273330 | AGRN |
| 204961_s_at | NM_000265 | Hs.647047 | NCF1 |
| 201453_x_at | NM_005614 | Hs.283521 | RHEB |
| 205504_at | NM_000061 | Hs.159494 | BTK |
| 228426_at | AI763426 | Hs.636624 | NAPSB |
| 204951_at | NM_004310 | Hs.654594 | RHOH |
| 227677_at | BF512748 | Hs.515247 | JAK3 |
| 226863_at | AI674565 | Hs.8379 | FAM110C |
| 235503_at | BF589787 | Hs.591712 | ASBS |
| 209990_s_at | AF056085 | Hs.198612 | GABBR2 |
| 227397_at | AA531086 | Hs.300772 | TPM2 |
| 213573_at | AA861608 | Hs.532793 | KPNB1 |
| 239767_at | W72323 | | |
| 203660_s_at | NM_006031 | Hs.474069 | PCNT |
| 217077_s_at | AF095723 | Hs.198612 | GABBR2 |
| 213574_s_at | AA861608 | Hs.532793 | KPNB1 |
| 213803_at | BG545463 | Hs.532793 | KPNB1 |
| 241350_at | AL533913 | Hs.656997 | FBXL22 |
| 204851_s_at | AF040254 | Hs.34780 | DCX |
| 201957_at | AF324888 | Hs.444403 | PPP1R12B |
| 40665_at | M83772 | Hs.445350 | FMO3 |
| 204850_at | NM_000555 | Hs.34780 | DCX |
| 210059_s_at | BC000433 | Hs.178695 | MAPK13 |
| 201958_s_at | NM_002481 | Hs.444403 | PPP1R12B |
| 202178_at | NM_002744 | Hs.496255 | PRKCZ |
| 216199_s_at | AL109942 | Hs.390428 | MAP3K4 |
| 211679_x_at | AF095784 | Hs.198612 | GABBR2 |
| 212654_at | AL566786 | Hs.300772 | TPM2 |
| 206496_at | NM_006894 | Hs.445350 | FMO3 |
| 204083_s_at | NM_003289 | Hs.300772 | TPM2 |
| 228737_at | AA211909 | Hs.26608 | TOX2 |
| 237206_at | AI452798 | Hs.567641 | MYOCD |
| 204089_x_at | NM_006724 | Hs.390428 | MAP3K4 |
| 233499_at | AI366175 | Hs.479658 | LRRC7 |
| 214577_at | BG164365 | Hs.637017 | MAP1B |
| 229578_at | AA716165 | Hs.441737 | JPH2 |
| 216331_at | AK022548 | Hs.524484 | ITGA7 |
| 217946_s_at | NM_016402 | Hs.515500 | SAE1 |
| 222548_s_at | AL561281 | Hs.431550 | MAP4K4 |
| 228724_at | N49237 | | |
| 200931_s_at | NM_014000 | Hs.643896 | VCL |
| 204053_x_at | U96180 | Hs.500466 | PTEN |
| 211711_s_at | BC005821 | Hs.500466 | PTEN |
| 224681_at | BG028884 | Hs.487341 | GNA12 |
| 202555_s_at | NM_005965 | Hs.477375 | MYLK |
| 204159_at | NM_001262 | Hs.525324 | CDKN2C |
| 212233_at | AL523678 | Hs.637017 | MAP1B |
| 218510_x_at | AI816291 | Hs.481704 | FAM134B |
| 227183_at | AI417267 | Hs.519666 | LOC728264 |
| 201234_at | NM_004517 | Hs.5158 | ILK |
| 219829_at | NM_012278 | Hs.109999 | ITGB1BP2 |
| 218181_s_at | NM_017792 | Hs.431550 | MAP4K4 |
| 226084_at | AA554833 | Hs.637017 | MAP1B |
| 221671_x_at | M63438 | Hs.449621 | IGKC |
| 224823_at | AA526844 | Hs.477375 | MYLK |
| 244780_at | AI800110 | Hs.591604 | SGPP2 |
| 235651_at | AV741130 | | |
| 205549_at | NM_006198 | Hs.80296 | PCP4 |
| 213596_at | AL050391 | Hs.138378 | CASP4 |
| 209663_s_at | AF072132 | Hs.524484 | ITGA7 |

TABLE 4-continued

List of probes used for tumor origin prediction

| Affymetrix Probe ID | Genbank Accession number | Unigene ID | Gene symbol |
|---|---|---|---|
| 212764_at | AI806174 | Hs.124503 | ZEB1 |
| 204165_at | NM_003931 | Hs.75850 | WASF1 |
| 205433_at | NM_000055 | Hs.420483 | BCHE |
| 223708_at | AF329838 | Hs.662633 | C1QTNF4 |
| 203951_at | NM_001299 | Hs.465929 | CNN1 |
| 209991_x_at | AF069755 | Hs.198612 | GABBR2 |
| 211792_s_at | U17074 | Hs.525324 | CDKN2C |
| 227662_at | A541622 | Hs.655519 | SYNPO2 |
| 236029_at | AI283093 | Hs.98523 | FAT3 |
| 238575_at | AI094626 | Hs.318775 | OSBPL6 |
| 214669_x_at | BG485135 | Hs.449621 | IGKC |
| 208694_at | U47077 | Hs.491682 | PRKDC |
| 203935_at | NM_001105 | Hs.470316 | ACVR1 |
| 1553530_a_at | NM_033669 | Hs.713531 | ITGB1 |
| 227180_at | AW138767 | Hs.274256 | ELOVL7 |
| 210058_at | BC000433 | Hs.178695 | MAPK13 |
| 214577_x_at | X57812 | Hs.449585 | IGLJ3 |
| 222797_at | BF508726 | Hs.299315 | DPYSL5 |
| 202274_at | NM_001615 | Hs.516105 | ACTG2 |
| 221651_x_at | BC005332 | Hs.449621 | IGKC |
| 1558828_s_at | AL703532 | Hs.519666 | LOC728264 |
| 201058_s_at | NM_006097 | Hs.504687 | MYL9 |
| 211430_s_at | M87789 | Hs.510635 | IGHG3 |
| 200771_at | NM_002293 | Hs.609663 | LAMC1 |
| 222871_at | BF791631 | Hs.10414 | KLHDC8A |
| 204548_at | NM_000349 | Hs.521535 | STAR |
| 220196_at | NM_024690 | Hs.432676 | MUC16 |
| 206125_s_at | NM_007196 | Hs.104570 | KLK8 |
| 204885_s_at | NM_005823 | Hs.408488 | MSLN |
| 209569_x_at | NM_014392 | Hs.518595 | D4S234E |
| 209570_s_at | BC001745 | Hs.518595 | S4S234E |
| 205624_at | NM_001870 | Hs.646 | CPA3 |
| 212063_at | BE903880 | Hs.502328 | CD44 |
| 216474_x_at | AF206667 | Hs.405479 | TPSAB1 |
| 207134_x_at | NM_024164 | Hs.405479 | TPSB2 |
| 205128_x_at | NM_000962 | Hs.201978 | PTGS1 |
| 215813_s_at | S36219 | Hs.201978 | PTGS1 |
| 207741_x_at | NM_003293 | Hs.405479 | TPSAB1 |
| 210084_x_at | AF206665 | Hs.405479 | TPSAB1 |
| 217023_x_at | AF099143 | Hs.405479 | TPSB2 |
| 204733_at | NM_002774 | Hs.79361 | KLK6 |
| 205683_x_at | NM_003294 | Hs.405479 | TPSAB1 |
| 219087_at | NM_017680 | Hs.435655 | ASPN |
| 209560_s_at | U15979 | Hs.533717 | DLK1 |
| 215382_x_at | AF206666 | Hs.405479 | TPSAB1 |
| 212935_at | AB002360 | Hs.170422 | MCF2L |
| 226534_at | AI446414 | Hs.1048 | KITLG |
| 204490_s_at | M24915 | Hs.502328 | CD44 |
| 219873_at | NM_024027 | Hs.32603 | COLEC11 |
| 229290_at | AI692575 | Hs.59761 | DAPL1 |
| 217523_at | AV700298 | Hs.502328 | CD44 |
| 209242_at | AL042588 | Hs.201776 | PEG3 |
| 229927_at | BE222220 | Hs.655520 | LEMD1 |
| 210916_s_at | AF098641 | Hs.502328 | CD44 |
| 203632_s_at | NM_016235 | Hs.148685 | GPRC5B |
| 204489_s_at | NM_000610 | Hs.502328 | CD44 |
| 227769_at | AI703476 | | |
| 203662_s_at | NM_003275 | Hs.494595 | TMOD1 |
| 226517_at | AL390172 | Hs.438993 | BCAT1 |
| 209291_at | AW157094 | Hs.519601 | ID4 |
| 214528_s_at | NM_013951 | Hs.469728 | PAX8 |
| 219331_s_at | NM_018203 | Hs.10414 | KLHDC8A |
| 225285_at | AK025615 | Hs.438993 | BCAT1 |
| 225809_at | AI659927 | Hs.105460 | DKFZP564O0823 |
| 205200_at | NM_003278 | Hs.476092 | CLEC3B |
| 209835_x_at | BC004372 | Hs.502328 | CD44 |
| 242468_at | AA767317 | | |
| 228360_at | BF060747 | Hs.357567 | LYPD6B |
| 202718_at | NM_000597 | Hs.438102 | IGFBP2 |
| 223496_at | AL136609 | Hs.97876 | CCDC8 |
| 212014_x_at | AI493245 | Hs.502328 | CD44 |
| 209794_at | AB007871 | Hs.654743 | SRGAP3 |
| 201288_at | NM_001175 | Hs.504877 | ARHGDIB |
| 209243_s_at | AF208967 | Hs.201776 | PEG3 |
| 205127_at | NM_000962 | Hs.201978 | PTGS1 |
| 207924_x_at | NM_013992 | Hs.469728 | PAX8 |
| 223754_at | BC005083 | Hs.389311 | MGC13057 |
| 223843_at | AB007830 | Hs.128856 | SCARA3 |
| 213523_at | AI671049 | Hs.244723 | CCNE1 |
| 205869_at | NM_002769 | Hs.713534 | PRSS1 |
| 205912_at | NM_000936 | Hs.501135 | PNLIP |
| 206446_s_at | NM_001971 | Hs.348395 | ELA1 |
| 205615_at | NM_001868 | Hs.2879 | CPA1 |
| 205971_s_at | NM_001906 | Hs.610926 | CTRB1 |
| 214411_x_at | AW584011 | Hs.632211 | CTRB2 |
| 206447_at | NM_001971 | Hs.348395 | ELA1 |
| 206151_x_at | NM_007352 | Hs.181289 | ELA3B |
| 210246_s_at | AF087138 | Hs.54470 | ABCC8 |
| 204035_at | NM_003469 | Hs.516726 | SCG2 |
| 231646_at | AW473496 | Hs.631993 | DPCR1 |
| 220106_at | NM_013389 | Hs.567486 | NPC1L1 |
| 204260_at | NM_001819 | Hs.516874 | CHGB |
| 223913_s_at | AB058892 | Hs.326728 | C19orf30 |
| 206915_at | NM_002509 | Hs.516922 | NKX2-2 |
| 205513_at | NM_001062 | Hs.2012 | TCN1 |
| 211766_s_at | BC005989 | Hs.423598 | PNLIPRP2 |
| 205815_at | NM_002580 | Hs.567312 | REG3A |
| 206694_at | NM_006229 | Hs.73923 | PNLIPRP1 |
| 204870_s_at | NM_002594 | Hs.315186 | PCSK2 |
| 203001_s_at | NM_007029 | Hs.521651 | STMN2 |
| 214324_at | BF222483 | Hs.53985 | GP2 |
| 205422_at | NM_004791 | Hs.696554 | ITGBL1 |
| 231993_at | AK026784 | Hs.696554 | ITGBL1 |
| 201860_s_at | NM_000930 | Hs.491582 | PLAT |
| 223753_s_at | AF312769 | Hs.567542 | CFC1 |
| 205509_at | NM_001871 | Hs.477891 | CPB1 |
| 222024_s_at | AK022014 | Hs.459211 | AKAP13 |
| 202627_s_at | AL574210 | Hs.414795 | SERPINE1 |
| 224396_s_at | AF316824 | Hs.435655 | ASPN |
| 203000_at | NM_004121 | Hs.437156 | GGT5 |
| 210162_s_at | U08015 | Hs.534074 | NFATC1 |
| 204363_at | NM_001993 | Hs.62192 | F3 |
| 203000_at | BF967657 | Hs.521651 | STMN2 |
| 228608_at | N49852 | Hs.525146 | NALCN |
| 206282_at | NM_002500 | Hs.574626 | NEUROD1 |
| 205886_at | NM_006507 | Hs.4158 | REG1B |
| 206681_x_at | NM_001502 | Hs.53985 | GP2 |
| 220275_at | NM_022034 | Hs.647182 | CUZD1 |
| 241137_at | AW338320 | Hs.631993 | DPCR1 |
| 205844_at | NM_004666 | Hs.12114 | VNN1 |
| 209752_at | AF172331 | Hs.49407 | REG1A |
| 205941_s_at | AI376003 | Hs.520339 | COL10A1 |
| 208473_s_at | NM_016295 | Hs.53985 | GP2 |
| 201109_s_at | AV726673 | Hs.164226 | THBS1 |
| 221718_s_at | M90360 | Hs.459211 | AKAP13 |
| 231148_at | AI806131 | Hs.99376 | IGFL2 |
| 222939_s_at | N30257 | Hs.591327 | SLC16A10 |
| 227099_s_at | AW276078 | Hs.714890 | LOC387763 |
| 208850_s_at | AL558479 | Hs.644697 | THY1 |
| 1558549_s_at | BG120535 | Hs.12114 | VNN1 |
| 227566_at | AW085558 | Hs.504352 | HNT |
| 229459_at | AV723914 | Hs.436854 | FAM19A5 |
| 219196_at | NM_013243 | Hs.232618 | SCG3 |
| 227140_at | AI343467 | | |
| 207412_x_at | NM_001808 | Hs.654361 | CELP |
| 222020_s_at | AW117456 | Hs.504352 | HNT |
| 210643_at | AF053712 | Hs.333791 | TNFSF11 |
| 204869_at | AL031664 | Hs.315186 | PCSK2 |
| 217628_at | X98568 | Hs.520339 | COL10A1 |
| 229655_at | N66656 | Hs.436854 | FAM19A5 |
| 205266_at | NM_002309 | Hs.2250 | LIF |
| 216840_s_at | AK026829 | Hs.200841 | LAMA2 |
| 207181_s_at | NM_001227 | Hs.9216 | CASP7 |
| 241450_at | AI224952 | Hs.135015 | RSPO1 |
| 201436_at | AI742789 | Hs.249718 | EIF4E |
| 201437_s_at | NM_001968 | Hs.249718 | EIF4E |
| 207058_s_at | NM_004562 | Hs.132954 | PARK2 |
| 204171_at | NM_003161 | Hs.463642 | RPS6KB1 |

TABLE 4-continued

List of probes used for tumor origin prediction

| Affymetrix Probe ID | Genbank Accession number | Unigene ID | Gene symbol |
|---|---|---|---|
| 32625_at | X15357 | Hs.490330 | NPR1 |
| 238815_s_at | BF529195 | Hs.591580 | LRRTM1 |
| 1555520_at | BC043542 | Hs.494538 | PTCH1 |
| 205189_s_at | NM_000136 | Hs.494529 | FANCC |
| 236773_at | AI635931 | | |
| 229147_at | AW070877 | | |
| 226675_s_at | W80468 | Hs.642877 | MALAT1 |
| 213143_at | BE856707 | Hs.526596 | C2orf72 |
| 214448_x_at | NM_002503 | Hs.9731 | NFKBIB |
| 232318_s_at | AI680459 | Hs.201441 | LOC121838 |
| 216623_x_at | AK025084 | Hs.460789 | TOX3 |
| 225859_at | N30645 | Hs.856076 | XIAP |
| 1557651_x_at | AK096127 | Hs.632380 | GALE |
| 237736_at | AI569844 | | |
| 206002_at | NM_005756 | Hs.146978 | GPR64 |
| 231259_s_at | BE467688 | Hs.376071 | CCND2 |
| 1565868_at | W96225 | Hs.502328 | CD44 |
| 219190_s_at | NM_017629 | Hs.471492 | EIF2C4 |
| 216942_at | D28586 | Hs.34341 | CD58 |
| 201016_at | BE542684 | Hs.522590 | EIF1AX |
| 217299_s_at | AK001017 | Hs.492208 | NBN |
| 221530_s_at | BE857425 | Hs.177841 | BHLHB3 |
| 215574_at | AU144294 | | |
| 223634_at | AF279143 | Hs.474711 | RASD2 |
| 210688_s_at | BC000185 | Hs.503043 | CPT1A |
| 207827_x_at | L36675 | Hs.271771 | SNCA |
| 202523_s_at | AI952009 | Hs.523009 | SPOCK2 |
| 201435_s_at | AW268640 | Hs.249718 | EIF4E |
| 201128_s_at | NM_001096 | Hs.387567 | ACLY |
| 209799_at | AF100763 | Hs.43322 | PRKAA1 |
| 211960_s_at | BG261416 | Hs.15734 | RAB7A |
| 227556_at | AI094580 | Hs.706952 | NME7 |
| 214590_s_at | AL545760 | Hs.129683 | EBE2D1 |
| 1552378_s_at | NM_172037 | Hs.244940 | RDH10 |
| 204579_at | NM_002011 | Hs.165950 | FGFR4 |
| 225609_at | AI888037 | Hs.271516 | GSR |
| 1558775_s_at | AU142380 | Hs.372000 | NSMAF |
| 1559459_at | BC043571 | Hs.309149 | LOC613266 |
| 218625_at | NM_016588 | Hs.103291 | NRN1 |
| 201019_at | NM_001412 | Hs.522590 | EIF1AX |
| 201585_s_at | BG035151 | Hs.355934 | SFPQ |
| 207414_s_at | NM_002570 | Hs.498494 | PCSK6 |
| 214147_at | AL046350 | Hs.709710 | C1orf175 |
| 224953_at | BG165815 | Hs.539684 | EIF2S3 |
| 238699_s_at | AI659225 | Hs.495984 | CASK |
| 229540_at | R45471 | Hs.479396 | RBPJ |
| 204859_s_at | NM_013229 | Hs.708112 | APAF1 |
| 205770_at | NM_000637 | Hs.271504 | GSR |
| 219591_at | NM_016564 | Hs.22140 | CEND1 |
| 206106_at | AL022328 | Hs.432642 | MAPK12 |
| 202618_s_at | L37298 | Hs.200716 | MECP2 |
| 241314_at | AI732874 | | |
| 202850_at | NM_002858 | Hs.700576 | ABCD3 |
| 202528_at | NM_000403 | Hs.632380 | GALE |
| 202409_at | X07868 | Hs.523414 | IGF2 |
| 228969_at | AI922323 | Hs.530009 | AGR2 |
| 209074_s_at | AL050264 | Hs.506357 | FAM107A |
| 207300_s_at | NM_000131 | Hs.36989 | F7 |
| 206536_at | U32974 | Hs.356076 | XIAP |
| 215530_at | BG484069 | Hs.567267 | FANCA |
| 204393_s_at | NM_001099 | Hs.433060 | ACPP |
| 204582_s_at | NM_001648 | Hs.171995 | KLK3 |
| 204583_at | U17040 | Hs.171995 | KLK3 |
| 209706_at | AF247704 | Hs.55999 | NKX3-1 |
| 209854_s_at | AA595465 | Hs.515560 | KLK2 |
| 209855_s_at | AF188747 | Hs.515560 | KLK2 |
| 210339_s_at | BC005196 | Hs.515560 | KLK2 |
| 239990_at | AI821426 | | |
| 237077_at | AI821895 | | |
| 243483_at | AI272941 | Hs.366053 | TRPM8 |
| 216920_s_at | M27331 | Hs.534032 | TARP |
| 215806_x_at | M13231 | Hs.534032 | TRGC2 |
| 211144_x_at | M30894 | Hs.534032 | TARP |
| 207430_s_at | NM_002443 | Hs.255462 | MSMB |
| 210297_s_at | U22178 | Hs.255462 | MSMB |
| 209813_x_at | M16768 | Hs.534032 | TRGV9 |
| 206001_at | NM_000905 | Hs.1832 | NPY |
| 223557_s_at | AB017269 | Hs.144513 | TMEFF2 |
| 235445_at | BF965166 | | |
| 236121_at | AI805082 | Hs.501758 | OR51E2 |
| 202429_s_at | AL353950 | Hs.435512 | PPP3CA |
| 230105_at | BF052550 | Hs.66731 | HOXB13 |
| 221424_s_at | NM_030774 | Hs.501758 | ORS1E2 |
| 231711_at | BF592752 | Hs.433060 | ACPP |
| 216942_x_at | AA911231 | Hs.435512 | PPP3CA |
| 209844_at | U57052 | Hs.66731 | HOXB13 |
| 33767_at | X15306 | Hs.198760 | NEFH |
| 242649_x_at | AI928428 | Hs.574240 | C15orf21 |
| 1561817_at | BF681305 | | |
| 232482_at | AF311306 | Hs.501758 | OR51E2 |
| 211303_x_at | AF261715 | Hs.645352 | PSMAL |
| 215363_x_at | AW168915 | Hs.654487 | FOLH1 |
| 237030_at | AI659898 | Hs.433050 | ACPP |
| 205564_at | NM_007003 | Hs.441038 | PAGE4 |
| 236255_at | AW993690 | | |
| 220116_at | NM_021614 | Hs.98280 | KCNN2 |
| 204412_s_at | NM_021076 | Hs.198760 | NEFH |
| 230784_at | BG498699 | Hs.116467 | C17orf92 |
| 230896_at | AA833830 | Hs.120591 | CCDC4 |
| 205860_x_at | NM_004476 | Hs.654487 | FOLH1 |
| 228796_at | BE645967 | Hs.199877 | CPNE4 |
| 206260_at | NM_003241 | Hs.438265 | TGM4 |
| 235342_at | AI808090 | Hs.481133 | SPOCK3 |
| 207362_at | NM_013309 | Hs.162989 | SLC30A4 |
| 203946_s_at | U75667 | Hs.708024 | ARG2 |
| 231783_at | AI500293 | Hs.632119 | CHRM1 |
| 213920_at | AB006631 | Hs.124953 | CUX2 |
| 203180_at | NM_000693 | Hs.459538 | ALDH1A3 |
| 205924_at | BC005035 | Hs.123072 | RAB3B |
| 228309_at | AI625747 | Hs.99913 | ADRB1 |
| 214087_s_at | BF593509 | Hs.654589 | MYBPC1 |
| 206167_s_at | NM_001174 | Hs.435291 | ARHGAP6 |
| 231336_at | AI703256 | Hs.199877 | CPNE4 |
| 227821_at | AW138143 | | |
| 227826_s_at | AW138143 | | |
| 221003_s_at | NM_030925 | Hs.87159 | CAB39L |
| 203129_s_at | BF059313 | Hs.435557 | KIF5C |
| 235892_at | AI620881 | | |
| 224393_s_at | AF307451 | Hs.209577 | CECR6 |
| 227123_at | AU156710 | Hs.123072 | RAB3B |
| 202425_x_at | NM_000944 | Hs.435512 | PPP3CA |
| 230595_at | BF677651 | Hs.9015 | LOCS72558 |
| 206827_s_at | NM_014274 | Hs.302740 | TRPV6 |
| 239202_at | BE552383 | | |
| 220723_s_at | NM_025087 | Hs.479703 | FLJ21511 |
| 205102_at | NM_005656 | Hs.439309 | TMPRSS2 |
| 226553_at | AI660243 | Hs.439309 | TMPRSS2 |
| 219775_s_at | NM_024695 | Hs.187694 | CPLX3 |
| 206434_at | NM_016950 | Hs.481133 | SPOCK3 |
| 210328_at | AF101477 | Hs.144914 | GNMT |
| 211689_s_at | AF270487 | Hs.439309 | TMPRSS2 |
| 220724_at | NM_025087 | Hs.479703 | FLI21511 |
| 230577_at | AW014022 | | |
| 203130_s_at | NM_004522 | Hs.435557 | KIF5C |
| 205925_at | NM_002867 | Hs.123072 | RAB3B |
| 230781_at | AI143988 | | |
| 201495_x_at | AI889739 | Hs.460109 | MYH11 |
| 231040_at | AW512988 | | |
| 1569886_a_at | BC040605 | Hs.715125 | GLB1L3 |
| 205833_s_at | AI770098 | Hs.661347 | PART1 |
| 201496_x_at | S67238 | Hs.460109 | MYH11 |
| 220187_at | NM_024636 | Hs.521008 | STEAP4 |
| 37512_at | U89281 | Hs.524513 | HSD1786 |
| 205827_at | NM_000729 | Hs.458426 | CCK |
| 239858_at | AI973051 | | |
| 212252_at | AA181179 | Hs.297343 | CAMKK2 |
| 202222_s_at | NM_001927 | Hs.594952 | DES |
| 225987_at | AA650281 | Hs.521008 | STEAP4 |

TABLE 4-continued

List of probes used for tumor origin prediction

| Affymetrix Probe ID | Genbank Accession number | Unigene ID | Gene symbol |
|---|---|---|---|
| 202363_at | AF231124 | Hs.643338 | SPOCK1 |
| 232306_at | BG289314 | Hs.54973 | CDH26 |
| 240331_at | AI820961 | | |
| 1554547_at | BC036453 | Hs.607594 | FAM13C1 |
| 228133_s_at | BF32767 | Hs.655378 | NDE1 |
| 238165_at | AW665629 | Hs.711998 | LOC100129282 |
| 215432_at | AC003034 | Hs.306812 | ACSM1 |
| 210213_s_at | AF022229 | Hs.654846 | EIF6 |
| 207457_s_at | NM_021246 | Hs.591792 | LY6G6D |
| 206858_s_at | NM_004503 | Hs.549040 | HOXC6 |
| 205767_at | NM_001432 | Hs.115263 | EREG |
| 214142_at | AI732905 | Hs.632195 | ZG16 |
| 231341_at | BE670584 | Hs.369703 | SLC35D3 |
| 231814_at | AK025404 | Hs.489355 | MUC12 |
| 220834_at | NM_017716 | Hs.272789 | MS4A12 |
| 211630_s_at | L42531 | Hs.82327 | GSS |
| 211729_x_at | BC005902 | Hs.488143 | BLVRA |
| 203773_x_at | NM_000712 | Hs.488143 | BLVRA |
| 201415_at | NM_000178 | Hs.82327 | GSS |
| 203771_s_at | AA740186 | Hs.488143 | BLVRA |
| 208726_s_at | BC000461 | Hs.429180 | EIF2S2 |
| 220056_at | NM_021258 | Hs.110915 | IL22RA1 |
| 206149_at | NM_022097 | Hs.178589 | CHP2 |
| 225667_s_at | AI601101 | Hs.260855 | FAM84A |
| 215702_s_at | W60595 | Hs.489786 | CFTR |
| 227736_at | AA553959 | Hs.298713 | C10orf99 |
| 205239_at | NM_001657 | Hs.270833 | AREG |
| 203116_s_at | NM_000140 | Hs.365365 | FECH |
| 227735_s_at | AA553959 | Hs.298713 | C10orf99 |
| 229358_at | AA628967 | Hs.654504 | IHH |
| 203895_at | AL35113 | Hs.472101 | PLCB4 |
| 205828_at | NM_002422 | Hs.375129 | MMP3 |
| 243669_s_at | AA502331 | Hs.15951 | PRAP1 |
| 203649_s_at | NM_000300 | Hs.466804 | PLA2G2A |
| 231439_at | AA922936 | | |
| 206268_at | NM_020997 | Hs.654718 | LEFTY1 |
| 202762_at | AL049383 | Hs.591600 | ROCK2 |
| 1553808_a_at | NM_145285 | Hs.243272 | NKX2-3 |
| 204254_s_at | NM_000376 | Hs.524368 | VDR |
| 229481_at | AI990367 | Hs.592059 | NKD1 |
| 210133_at | D49372 | Hs.54460 | CCL11 |
| 210390_s_at | AF031587 | Hs.272493 | CCL15 |
| 235147_at | RS6118 | | |
| 221204_s_at | NM_018058 | Hs.500736 | CRTAC1 |
| 209877_at | AF010126 | Hs.349470 | SNCG |
| 204612_at | NM_006823 | Hs.433700 | PKIA |
| 215729_s_at | BE542323 | Hs.496843 | VGLL1 |
| 203031_s_at | NM_000375 | Hs.501376 | URO5 |
| 40560_at | U28049 | Hs.705451 | TBX2 |
| 209156_s_at | AY029208 | Hs.420269 | COL6A2 |
| 208451_s_at | NM_000592 | Hs.534847 | C4B |
| 218692_at | NM_017786 | Hs.390738 | GOLSYN |
| 219736_at | NM_018700 | Hs.519514 | TRIM36 |
| 218532_s_at | NM_019000 | Hs.481704 | FAM134B |
| 205630_at | NM_000756 | Hs.75294 | CRH |
| 219355_at | NM_018015 | Hs.274267 | CXorf57 |
| 205487_s_at | NM_016267 | Hs.496843 | VGLL1 |
| 1554592_a_at | BC028721 | Hs.515217 | SLC1A6 |
| 212624_s_at | BF339445 | Hs.654534 | CHN1 |
| 213417_at | AW173045 | Hs.705451 | TBX2 |
| 202357_s_at | NM_001710 | Hs.69771 | CFB |
| 204103_at | NM_002984 | Hs.75703 | CCL4 |
| 202604_x_at | NM_001110 | Hs.578508 | ADAM10 |
| 231579_s_at | BE968786 | Hs.633514 | TIMP2 |
| 202411_at | NM_005532 | Hs.532634 | IFI27 |
| 224560_at | BF107565 | Hs.633514 | TIMP2 |
| 238452_at | AI393356 | Hs.517422 | FCRLB |
| 226980_at | AI345957 | Hs.520525 | FNDC1 |
| 203913_s_at | AL574184 | Hs.655491 | HPGD |
| 203167_at | NM_003255 | Hs.633514 | TIMP2 |
| 202844_s_at | AW025261 | Hs.528993 | RALBP1 |
| 241382_at | W22165 | Hs.433150 | PCP4L1 |
| 204465_s_at | NM_004692 | Hs.500916 | INA |
| 214896_s_at | AU135154 | Hs.578508 | ADAM10 |
| 202410_x_at | NM_000612 | Hs.523414 | IGF2 |
| 217165_x_at | M10943 | Hs.513626 | MT1F |
| 226864_at | BF245954 | Hs.433700 | PKIA |
| 204818_at | NM_002153 | Hs.162795 | HSD17B2 |
| 243792_x_at | AI281371 | Hs.436142 | PTPN13 |
| 1557382_x_at | AI659151 | Hs.511787 | KIAA1975 |
| 225093_at | N66570 | Hs.133135 | UTRN |
| 1555497_a_at | AY151049 | Hs.436317 | CYP4B1 |
| 244692_at | AW025687 | Hs.156452 | CYP4F22 |
| 202765_s_at | AI264196 | Hs.591133 | FBN1 |
| 201599_at | NM_000274 | Hs.523332 | OAT |
| 203914_x_at | NM_000860 | Hs.655491 | HPGD |
| 228806_at | AI218580 | Hs.256022 | RORC |
| 211105_s_at | U80918 | Hs.534074 | NFATC1 |
| 228232_s_at | NM_014312 | Hs.112377 | VSIG2 |
| 223582_at | AF055084 | Hs.591777 | GPR98 |
| 211549_s_at | U63296 | Hs.655491 | HPGD |
| 205114_s_at | NM_002983 | Hs.514107 | CCL3 |
| 205081_at | NM_001311 | Hs.70327 | CRIP1 |
| 217767_at | NM_000064 | Hs.529053 | C3 |
| 204201_s_at | NM_006264 | Hs.436142 | PTPN13 |
| 210118_s_at | M15329 | Hs.1722 | IL1A |
| 1555349_a_at | L78790 | Hs.375957 | ITGB2 |
| 204532_x_at | NM_021027 | Hs.554822 | UGT1A9 |
| 206882_at | NM_005071 | Hs.515217 | SLC1A6 |
| 211548_s_at | J05594 | Hs.655491 | HPGD |
| 206572_x_at | U06654 | Hs.154069 | MLANA |
| 205337_at | AL139318 | Hs.301865 | DCT |
| 209848_s_at | U01874 | Hs.95972 | SILV |
| 210944_s_at | BC003169 | Hs.143261 | CAPN3 |
| 210138_at | AF074979 | Hs.368733 | RGS20 |
| 231666_at | AA194193 | Hs.42146 | PAX3 |
| 209686_at | BC001766 | Hs.422181 | S100B |
| 204995_at | AL567411 | Hs.500015 | CDK5R1 |
| 204466_s_at | BG260394 | Hs.271771 | SNCA |
| 214299_at | AI367319 | Hs.376984 | SOX10 |
| 219412_at | NM_022337 | Hs.591975 | RAB38 |
| 211546_x_at | L36674 | Hs.271771 | SNCA |
| 214475_x_at | AF127764 | Hs.143261 | CAPN3 |
| 236972_at | AI351421 | Hs.279709 | TRIM63 |
| 211890_x_at | AF127765 | Hs.143261 | CAPN3 |
| 206898_at | NM_021153 | Hs.42771 | CDH19 |
| 235639_at | AL137939 | Hs.89603 | MUC1 |
| 213693_s_at | AI610869 | Hs.166017 | MITF |
| 207233_s_at | NM_000248 | Hs.271771 | SNCA |
| 204467_s_at | NM_000345 | Hs.44424 | SLC6A15 |
| 206376_at | NM_018057 | Hs.436996 | PHACTR1 |
| 213638_at | AW054711 | Hs.376984 | SOX10 |
| 209843_s_at | BC002824 | Hs.654970 | IL17RB |
| 219255_x_at | NM_018725 | Hs.42146 | PAX3 |
| 216059_at | U02309 | Hs.148716 | ST3GAL6 |
| 213355_at | AI989567 | Hs.82002 | EDNRB |
| 206701_x_at | NM_003991 | | |
| 230741_at | AI655467 | Hs.27935 | TTYH2 |
| 223741_s_at | BC004233 | Hs.43697 | ETV5 |
| 203348_s_at | BF060791 | Hs.166017 | MITF |
| 226826_at | AL117653 | Hs.89603 | MUC1 |
| 207847_s_at | NM_002456 | Hs.497816 | MOSC1 |
| 218865_at | NM_022746 | Hs.253146 | PLEKHA6 |
| 229245_at | AA535361 | Hs.654978 | RAB27A |
| 202355_s_at | BE502030 | Hs.16529 | TSPAN12 |
| 219274_at | NM_012338 | Hs.390599 | LOC440335 |
| 229599_at | AA675917 | Hs.288229 | STXBP1 |
| 202250_s_at | NM_003165 | Hs.75799 | PRSS8 |
| 202525_at | NM_002773 | Hs.82002 | EDNRB |
| 204273_at | NM_000115 | Hs.74124 | GPR143 |
| 206696_at | NM_000273 | Hs.437039 | PRKAA2 |
| 227892_at | AA855042 | Hs.21213 | MYO5A |
| 241689_at | N67810 | Hs.335355 | SLC44A4 |
| 205597_at | NM_025257 | Hs.15154 | SRPX |
| 204955_at | NM_006307 | Hs.654978 | RAB27A |
| 210951_x_at | AF125393 | Hs.495728 | PIR |
| 207469_s_at | NM_003662 | Hs.499725 | ANK3 |
| 209442_x_at | AL136710 | | |

TABLE 4-continued

List of probes used for tumor origin prediction

| Affymetrix Probe ID | Genbank Accession number | Unigene ID | Gene symbol |
|---|---|---|---|
| 224361_s_at | AF250309 | Hs.654970 | IL17RB |
| 225728_at | AI659533 | Hs.619806 | SORBS2 |
| 1557905_s_at | AL552534 | Hs.502328 | CD44 |
| 212339_at | AL121895 | Hs.437422 | EPB41L1 |
| 206552_s_at | NM_003182 | Hs.2563 | TAC1 |
| 231626_at | BE220053 | | |
| 1568603_at | AI912173 | Hs.654933 | CADPS |
| 207074_s_at | NM_003053 | Hs.158322 | SLC18A1 |
| 214601_at | AI350339 | Hs.591999 | TPH1 |
| 229300_at | AW590679 | | |
| 214811_at | AB002316 | Hs.657441 | RIMBP2 |
| 240236_at | N50117 | Hs.477315 | STXBPSL |
| 205999_x_at | AF182273 | Hs.654391 | CYP3A4 |
| 223810_at | AF252283 | Hs.508201 | KLHL1 |
| 228598_at | AL538780 | Hs.591555 | DPP10 |
| 207529_at | NM_021010 | Hs.655233 | DEFA5 |
| 206135_at | NM_014682 | Hs.655499 | ST18 |
| 220074_at | NM_017717 | Hs.165619 | MUPCDH |
| 216086_at | AB028977 | Hs.663229 | SV2C |
| 1568604_a_at | AI912173 | Hs.654933 | CADPS |
| 211843_x_at | AF315325 | Hs.111944 | CYP3A7 |
| 219643_at | NM_018557 | Hs.656461 | LRP1B |
| 229944_at | AU153412 | Hs.106795 | OPRK1 |
| 207814_at | NM_001926 | Hs.711 | DEFA6 |
| 206664_at | NM_001041 | Hs.429596 | SI |
| 215045_at | BC004145 | Hs.26047 | TNRC4 |
| 219896_at | NM_015722 | Hs.148634 | CALY |
| 206773_at | NM_002347 | Hs.159590 | LY6H |
| 209462_at | U48437 | Hs.74565 | APLP1 |
| 239884_at | BE467579 | Hs.654933 | CAPDS |
| 233950_at | AK000873 | Hs.654933 | CAPDS |
| 242660_at | AA846789 | Hs.662505 | LOC100128641 |
| 200697_at | NM_000188 | Hs.657990 | HK1 |
| 207544_s_at | NM_000672 | Hs.586161 | ADH6 |
| 243339_at | AI796076 | | |
| 232321_at | AK026404 | Hs.271819 | MUC17 |
| 244170_at | H05254 | | |
| 205825_at | NM_000439 | Hs.78977 | PCSK1 |
| 1556641_at | AK094547 | Hs.596660 | SLC7A14 |
| 213438_at | AA995925 | Hs.13349 | NFASC |
| 243231_at | N62096 | Hs.658702 | SLC38A11 |
| 220639_at | NM_024795 | Hs.156652 | TM4SF20 |
| 230075_at | AV724323 | Hs.632832 | RAB39B |
| 206484_s_at | NM_003399 | Hs.170499 | XPNPEP2 |
| 211357_s_at | BC005314 | Hs.530274 | ALDOB |
| 228329_at | AA700440 | Hs.477370 | DAB1 |
| 230112_at | AB037820 | Hs.170388 | 39876 |
| 230220_at | AI681025 | Hs.438914 | C2orf21 |
| 239270_at | AL133721 | Hs.145404 | PLCXD3 |
| 206502_s_at | NM_002196 | Hs.89584 | INSM1 |
| 207558_s_at | NM_000325 | Hs.643588 | PITX2 |
| 214157_at | AA401492 | Hs.125898 | GNAS |
| 225016_at | N48299 | Hs.293274 | APCDD1 |
| 219532_at | NM_022726 | Hs.101915 | ELOVL4 |
| 224355_at | AF237905 | Hs.150878 | MS4A8B |
| 204874_x_at | NM_003933 | Hs.458427 | BAIAP3 |
| 205969_at | NM_001086 | Hs.506908 | AADAC |
| 239805_at | AW136060 | Hs.102307 | SLC13A2 |
| 1557146_a_at | T03074 | Hs.711586 | FLJ32252 |
| 203779_s_at | NM_005797 | Hs.116651 | MPZL2 |
| 206975_at | NM_000595 | Hs.36 | LTA |
| 202508_s_at | NM_003081 | Hs.167317 | SNAP25 |
| 205626_s_at | NM_004929 | Hs.65425 | CALB1 |
| 219659_at | AU146927 | Hs.444957 | ATP8A2 |
| 211483_x_at | AF081924 | Hs.351887 | CAMK2B |
| 229818_at | AL359592 | Hs.4221 | SVOP |
| 203029_s_at | NM_002847 | Hs.490789 | PTPRN2 |
| 205390_s_at | NM_000037 | Hs.654438 | ANK1 |
| 232165_at | AL137725 | Hs.200412 | EPPK1 |
| 203397_s_at | BF063271 | Hs.170986 | GALNT3 |
| 206157_at | NM_002852 | Hs.591286 | PTX3 |
| 232164_s_at | AL137725 | Hs.200412 | EPPK1 |
| 202005_at | NM_021978 | Hs.504315 | ST14 |
| 203453_at | NM_001038 | Hs.591047 | SCNN1A |
| 213947_s_at | AI867102 | Hs.475525 | NUP210 |
| 225645_at | AI763378 | Hs.653859 | EHF |
| 204038_s_at | NM_001401 | Hs.126667 | LPAR1 |
| 223232_s_at | AI768894 | Hs.591464 | CGN |
| 235548_at | BG326592 | Hs.119286 | APCDD1L |
| 211974_x_at | AL513759 | Hs.479396 | RBPJ |
| 210105_s_at | M14333 | Hs.390567 | FYN |
| 35617_at | U29725 | Hs.150136 | MAPK7 |
| 226535_at | AK026736 | Hs.470399 | ITGB6 |
| 204036_at | AW269335 | Hs.126667 | LPAR1 |
| 220392_at | NM_022659 | Hs.710674 | EBF2 |
| 226342_at | AW593244 | Hs.503178 | SPTBN1 |
| 229800_at | AI129626 | Hs.507755 | DCLK1 |
| 220035_at | NM_024923 | Hs.475525 | NUP210 |
| 205780_at | NM_001197 | Hs.475055 | BIK |
| 226096_at | AI760132 | Hs.524234 | FNDC5 |
| 201209_at | NM_004964 | Hs.88556 | HDAC1 |
| 212486_s_at | N20923 | Hs.390567 | FYN |
| 219630_at | NM_005764 | Hs.431099 | PDZK1IP1 |
| 209114_at | AF133425 | Hs.38972 | TSPAN1 |
| 1553589_a_at | NM_005764 | Hs.431099 | PDZK1IP1 |
| 230438_at | AI039005 | Hs.146196 | TBX15 |
| 209017_at | AV718192 | Hs.130031 | TRIO |
| 224793_s_at | AA604375 | Hs.494622 | TGFBR1 |
| 204503_at | NM_001988 | Hs.500635 | EVPL |
| 203851_at | NM_002178 | Hs.274313 | IGFBP6 |
| 222675_s_at | AA628400 | Hs.656063 | BAIAP2L1 |
| 223423_at | BC000181 | Hs.231320 | GPR160 |
| 238567_at | AW779536 | Hs.591604 | SGPP2 |
| 223631_s_at | AF213678 | Hs.631544 | C18orf33 |
| 218221_at | AL042842 | Hs.632446 | ARNT |
| 202459_s_at | BC005238 | Hs.301350 | FXYD3 |
| 236361_at | BF432376 | Hs.411308 | GALNTL2 |
| 210135_s_at | AF022654 | Hs.55967 | SHOX2 |
| 207316_at | NM_001523 | Hs.57697 | HAS1 |
| 202286_s_at | J04152 | Hs.23582 | TACSTD2 |
| 219388_at | NM_024915 | Hs.661088 | GRHL2 |
| 206680_at | NM_005894 | Hs.134035 | CD5L |
| 206380_s_at | NM_002621 | Hs.53155 | CFP |
| 214074_s_at | BG475299 | Hs.596164 | CTTN |
| 221239_s_at | NM_030764 | Hs.437393 | FCRL2 |
| 205033_s_at | NM_004084 | Hs.380781 | DEFA1 |
| 228518_at | AW575313 | Hs.510635 | IGHG1 |
| 209017_at | AI761748 | Hs.592142 | NCOA3 |
| 206210_s_at | NM_000078 | Hs.89538 | CETP |
| 202880_s_at | NM_004762 | Hs.191215 | CYTH1 |
| 207655_s_at | NM_013314 | Hs.665244 | BLNK |
| 226068_at | BF593625 | Hs.371720 | SYK |
| 223049_at | AF246238 | Hs.444356 | GRB2 |
| 203394_s_at | BE973687 | Hs.250666 | HES1 |
| 201465_s_at | BC002646 | Hs.714791 | JUN |
| 202625_at | AI356412 | Hs.699154 | LYN |
| 231856_at | AB033070 | Hs.656215 | KIAA1244 |
| 201841_s_at | NM_001540 | Hs.520973 | HSPB1 |
| 209154_at | AF234997 | Hs.12956 | TAX1BP3 |
| 210010_s_at | U25147 | Hs.111024 | SLC25A1 |
| 1554600_s_at | BC033088 | Hs.594444 | LMNA |
| 204259_at | NM_002423 | Hs.2256 | MMP7 |
| 218804_at | NM_018043 | Hs.503074 | ANO1 |
| 208799_at | BC004146 | Hs.422990 | PSMB5 |
| 206915_at | NM_002350 | Hs.699154 | LYN |
| 244023_at | AW467357 | Hs.371720 | SYK |
| 226189_at | BF513121 | Hs.592171 | ITGB8 |
| 227817_at | R51324 | Hs.460355 | PRKCB |
| 203411_s_at | NM_005572 | Hs.594444 | LMNA |
| 212992_at | AI935123 | Hs.441783 | AHNAK2 |
| 211896_s_at | AF138302 | Hs.706262 | DCN |
| 215464_s_at | AK001327 | Hs.12956 | TAX1BP3 |
| 215807_s_at | AV693216 | Hs.476209 | PLXNB1 |
| 1560225_at | AI434253 | Hs.75110 | CNR1 |
| 215075_s_at | L29511 | Hs.444356 | GRB2 |
| 36711_at | AL021977 | Hs.517617 | MAFF |
| 210754_s_at | M79321 | Hs.699154 | LYN |
| 209856_x_at | U31089 | Hs.471156 | ABI2 |

TABLE 4-continued

List of probes used for tumor origin prediction

| Affymetrix Probe ID | Genbank Accession number | Unigene ID | Gene symbol |
|---|---|---|---|
| 222920_s_at | BG231515 | Hs.33187 | KIAA0748 |
| 201903_at | NM_003365 | Hs.119251 | UQCRC1 |
| 242785_at | BF663308 | Hs.656692 | FLJ42562 |
| 221602_s_at | AF057557 | Hs.58831 | FAIM3 |
| 207238_s_at | NM_002838 | Hs.654514 | PTPRC |
| 221571_at | AI721219 | Hs.510528 | TRAF3 |
| 213265_at | AI570199 | Hs.601055 | PGA3 |
| 235591_at | R62424 | Hs.248160 | SSTR1 |
| 205517_at | AV700724 | Hs.243987 | GATA4 |
| 209301_at | M36532 | Hs.155097 | CA2 |
| 206561_s_at | NM_020299 | Hs.116724 | AKR1B10 |
| 232352_at | AK001022 | Hs.444677 | ISL2 |
| 220421_at | NM_024850 | Hs.189109 | BTNL8 |
| 225330_at | AL044092 | Hs.643120 | IGF1R |
| 214510_at | NM_005293 | Hs.188859 | GPR20 |
| 202949_s_at | NM_001450 | Hs.443687 | FHL2 |
| 206262_at | NM_000669 | Hs.654537 | ADH1C |
| 203438_at | AI435828 | Hs.233160 | STC2 |
| 214133_at | AI611214 | | LOC100133432 |
| 226907_at | N32557 | Hs.486798 | PPP1R14C |
| 209950_s_at | BC004300 | Hs.103665 | VILL |
| 205009_at | NM_003225 | Hs.162807 | TFF1 |
| 214164_x_at | BF752277 | Hs.210995 | CA12 |
| 203627_at | AI830698 | Hs.643120 | IGF1R |
| 207522_s_at | NM_005173 | Hs.513870 | ATP2A3 |
| 227166_at | AK025872 | Hs.495984 | CASK |
| 227048_at | AI990816 | Hs.270364 | LAMA1 |
| 205343_at | NM_001056 | Hs.436123 | SULT1C2 |
| 214014_at | W81196 | Hs.343380 | CDC42EP2 |
| 236264_at | BF511741 | Hs.28391 | LPHN3 |
| 210735_s_at | BC000278 | Hs.210995 | CA12 |
| 205842_s_at | AF001362 | Hs.656213 | JAK2 |
| 213036_x_at | Y15724 | Hs.513870 | ATP2A3 |
| 207139_at | NM_000704 | Hs.36992 | ATP4A |
| 208250_s_at | NM_004406 | Hs.279611 | DMBT1 |
| 230135_at | AI822137 | | |
| 1557545_s_at | BF529886 | Hs.501114 | RNF165 |
| 237466_at | AW444502 | Hs.507991 | HHIP |
| 212816_s_at | BE613178 | Hs.533013 | CBS |
| 204508_s_at | BC001012 | Hs.210995 | CA12 |
| 229160_at | AI967987 | Hs.592221 | MUM1L1 |
| 209875_s_at | M83248 | Hs.313 | SPP1 |
| 206242_at | NM_003963 | Hs.184194 | TM4SF5 |
| 230923_at | AI824004 | Hs.655061 | FAM19A1 |
| 1558796_a_at | AL833240 | Hs.709829 | LOC728052 |
| 203628_at | H05812 | Hs.643120 | IGF1R |
| 223877_at | AF329839 | Hs.153714 | C1QTNF7 |
| 212713_at | R72286 | Hs.296094 | MFAP4 |
| 203131_at | NM_006206 | Hs.74615 | PDGFRA |
| 217590_s_at | AA502609 | Hs.137674 | TRPA1 |
| 229400_at | AW299531 | Hs.123070 | HOXD10 |
| 203963_at | NM_001218 | Hs.210995 | CA12 |
| 218880_at | N36408 | Hs.220971 | FOSL2 |
| 225958_at | AI554106 | Hs.305985 | PHC1 |
| 210993_s_at | U54826 | Hs.604588 | SMAD1 |
| 227798_at | AU146891 | Hs.604588 | SMAD1 |
| 202514_at | AW139131 | Hs.292549 | DLG1 |
| 225144_at | AI457436 | Hs.471119 | BMPR2 |
| 203269_at | NM_003580 | Hs.372000 | NSMAF |
| 1861_at | U66879 | Hs.370254 | BAD |
| 211464_x_at | U20537 | Hs.654616 | CASP6 |
| 208855_at | BG534245 | Hs.529862 | CSNK1A1 |
| 201464_x_at | BG491844 | Hs.714791 | JUN |
| 218338_at | NM_004426 | Hs.305985 | PHC1 |
| 210627_s_at | BC002804 | Hs.516119 | GCS1 |
| 202704_at | AA675892 | Hs.709952 | TOB1 |
| 202484_at | AF072242 | Hs.25674 | MBD2 |
| 209349_at | U63139 | Hs.655835 | RAD50 |
| 225262_at | AI670862 | Hs.220971 | FOSL2 |
| 203395_s_at | NM_005524 | Hs.250666 | HES1 |
| 209790_s_at | BC000305 | Hs.654616 | CASP6 |
| 201466_s_at | NM_002228 | Hs.714791 | JUN |
| 210512_s_at | AF022375 | Hs.73793 | VEGFA |
| 209160_at | AB018580 | Hs.78183 | AKR1C3 |
| 202351_at | AI093579 | Hs.436873 | ITGAV |
| 202417_at | NM_012289 | Hs.455870 | KEAP1 |
| 233849_s_at | AK023014 | Hs.592313 | ARHGAP5 |
| 203581_at | BC002438 | Hs.596169 | RAB4A |
| 215356_at | AK023134 | Hs.646351 | TDRD12 |
| 226852_at | AB033092 | Hs.435413 | MTA3 |
| 208891_at | BC003143 | Hs.298654 | DUSP6 |
| 214119_s_at | AI936769 | Hs.471933 | FKBP1A |
| 203132_at | NM_000321 | Hs.408528 | RB1 |
| 213980_s_at | AA053830 | Hs.208597 | CTBP1 |
| 217936_at | AW044631 | Hs.592313 | ARHGAP5 |
| 225985_at | AI935917 | Hs.43322 | PRKAA1 |
| 1552648_a_at | NM_003844 | Hs.591834 | TNFRSF10A |
| 212741_at | AA923354 | Hs.183109 | MAOA |
| 208711_s_at | BC000076 | Hs.523852 | CCND1 |
| 232149_s_at | BF056507 | Hs.372000 | NSMAF |
| 1557417_s_at | AA844689 | Hs.442339 | RSPH10B |
| 1556194_a_at | BC042959 | | |
| 225757_at | AU147564 | Hs.301478 | CLMN |
| 210896_s_at | AF306765 | Hs.622998 | ASPH |
| 202935_s_at | AI382146 | Hs.707993 | SOX9 |
| 226048_at | N92719 | Hs.138211 | MAPK8 |
| 213724_s_at | AI870615 | Hs.256667 | PDK2 |
| 228670_at | BF197089 | Hs.508835 | TEP1 |
| 214259_s_at | AI144075 | Hs.571886 | AKR7A2 |
| 208724_s_at | BC000905 | Hs.310645 | RAB1A |
| 203673_at | NM_003235 | Hs.654591 | TG |
| 214977_at | AK023852 | | |
| 210055_at | BE045816 | Hs.160411 | TSHR |
| 210342_s_at | M17755 | Hs.467554 | TPO |
| 215443_at | BE740743 | Hs.160411 | TSHR |
| 231070_at | BF431199 | Hs.310225 | IYD |
| 228715_at | AV725825 | Hs.21417 | ZCCHC12 |
| 213482_at | BF593175 | Hs.476284 | DOCK3 |
| 213228_at | AK023913 | Hs.584830 | PDE8B |
| 207144_s_at | NM_004143 | Hs.40403 | CITED1 |
| 239006_at | AI758950 | Hs.354013 | SLC26A7 |
| 229782_at | BE468066 | Hs.652568 | RMST |
| 207695_s_at | NM_001555 | Hs.22111 | IGSF1 |
| 1554789_a_at | AB085825 | Hs.584830 | PDE8B |
| 222325_at | AW974812 | | |
| 242344_at | AA772920 | Hs.303527 | GABRB2 |
| 1557136_at | BG059633 | Hs.674423 | ATP13A4 |
| 219836_at | NM_024508 | Hs.136912 | ZBED2 |
| 235460_at | AW149670 | Hs.708268 | SNX22 |
| 209824_s_at | AB000812 | Hs.65734 | ARNTL |
| 227238_at | W93847 | Hs.407152 | MUC15 |
| 210971_s_at | AB000815 | Hs.65734 | ARNTL |
| 238047_at | AA405456 | Hs.22905 | RP13-102H20.1 |
| 219529_at | NM_004669 | Hs.64746 | CLIC3 |
| 227241_at | R79759 | Hs.407152 | MUC15 |
| 235251_at | AW292765 | | |
| 221795_at | AI346341 | Hs.494312 | NTRK2 |
| 214680_at | BF674712 | Hs.494312 | NTRK2 |
| 1557122_s_at | BC036592 | Hs.303527 | GABRB2 |
| 206457_s_at | NM_000792 | Hs.251415 | DIO1 |
| 219949_at | NM_024512 | Hs.657345 | LRRC6 |
| 1565936_a_at | T24091 | Hs.504908 | LMO3 |
| 202219_at | NM_005629 | Hs.540696 | SLC6A8 |
| 200832_s_at | AB032261 | Hs.558396 | SCD |
| 222294_s_at | AW971415 | Hs.654978 | RAB27A |
| 228984_at | AB037815 | Hs.502982 | KIAA1394 |
| 221796_at | AA707199 | Hs.494312 | NTRK2 |
| 210621_s_at | M23612 | Hs.664080 | RASA1 |
| 205728_at | AL022718 | | |
| 1555404_a_at | BC029819 | Hs.356664 | DUOXA1 |
| 235766_x_at | AA743462 | Hs.654978 | RAB27A |
| 221539_at | AB044548 | Hs.411641 | EIF4EBP1 |
| 223623_at | AF325503 | Hs.43125 | C2orf40 |
| 223572_at | AB042554 | Hs.476041 | HHATL |
| 209292_at | AL022726 | Hs.519601 | ID4 |
| 228173_at | AA810695 | Hs.125898 | GNAS |
| 205954_at | NM_006917 | Hs.26550 | RXRG |
| 201587_s_at | NM_001569 | Hs.522819 | IRAK1 |

TABLE 4-continued

List of probes used for tumor origin prediction

| Affymetrix Probe ID | Genbank Accession number | Unigene ID | Gene symbol |
|---|---|---|---|
| 219597_s_at | NM_017434 | Hs.272813 | DUOX1 |
| 209515_s_at | U38654 | Hs.654978 | RAB27A |
| 231240_at | AI038059 | Hs.202354 | DIO2 |
| 230585_at | AI632692 | | |
| 219727_at | NM_014080 | Hs.71377 | DUOX2 |
| 203413_at | NM_006159 | Hs.505326 | NELL2 |
| 213106_at | AI769688 | Hs.435052 | ATP8A1 |
| 232424_at | AI623202 | Hs.99500 | PRDM16 |
| 208892_s_at | BC003143 | Hs.298654 | DUSP6 |
| 209683_at | AA243659 | Hs.467769 | FAM49A |
| 232478_at | AU146021 | | |
| 235977_at | BF433341 | Hs.21380 | LONRF2 |
| 225911_at | AL138410 | Hs.518921 | NPNT |
| 230276_at | AI934342 | Hs.46779 | FAM49A |
| 230290_at | BE674338 | Hs.12923 | SCUBE3 |
| 225433_at | AU144104 | Hs.592334 | GTF2A1 |
| 215240_at | AI189839 | Hs.218040 | ITGB3 |
| 37986_at | M60459 | Hs.631624 | EPOR |
| 203699_s_at | U53506 | Hs.202354 | DIO2 |
| 202788_at | NM_004635 | Hs.234521 | MAPKAPK3 |
| 205721_at | U97145 | Hs.441202 | GFRA2 |
| 228955_at | AL041761 | | |
| 225996_at | AV709727 | Hs.21380 | LONRF2 |
| 231348_s_at | BF508869 | Hs.504908 | LMO3 |
| 225380_at | BF528878 | Hs.408542 | LOC91461 |
| 202787_s_at | U43784 | Hs.234521 | MAPKAPK3 |
| 222901_s_at | AF153815 | Hs.463985 | KCNJ16 |
| 227449_at | AI799018 | Hs.371218 | EPHA4 |
| 222830_at | BE566136 | Hs.418493 | GRHL1 |
| 208078_s_at | NM_030751 | Hs.124503 | ZEB1 |
| 223278_at | M86849 | Hs.524894 | GJB2 |
| 204225_at | NM_006037 | Hs.20516 | HDAC4 |
| 220751_s_at | NM_016348 | Hs.519694 | C5orf4 |
| 212224_at | NM_000689 | Hs.76392 | ALDH1A1 |
| 212983_at | NM_005343 | Hs.37003 | HRAS |
| 35846_at | M24899 | Hs.724 | THRA |
| 201116_s_at | AI922855 | Hs.712551 | CPE |
| 205220_at | NM_006018 | Hs.458425 | GPR109B |
| 200863_at | AI215102 | Hs.321541 | RAB11A |
| 204420_at | BG251266 | Hs.283565 | FOSL1 |
| 208760_at | AL031714 | Hs.302903 | UBE2I |
| 203625_x_at | BF105365 | Hs.23348 | SKP2 |
| 236523_at | BF435831 | Hs.480371 | LOC285556 |
| 227705_at | BF591534 | Hs.21861 | TCEAL7 |
| 209904_at | AF020769 | Hs.118845 | TNNC1 |
| 235004_at | AI677701 | Hs.519904 | RBM24 |
| 207302_at | NM_000231 | Hs.37167 | SGCG |
| 233364_s_at | AK021804 | | |
| 206717_at | NM_002472 | Hs.700484 | MYH8 |
| 34471_at | M36769 | Hs.700484 | MYH8 |
| 219186_at | NM_020224 | Hs.591384 | ZBTB7A |
| 219728_at | NM_006790 | Hs.84665 | MYOT |
| 217057_s_at | AF107846 | Hs.125898 | GNAS |
| 220359_s_at | NM_016300 | Hs.475902 | ARPP-21 |
| 243346_at | BF109621 | Hs.350621 | LMOD3 |
| 200604_s_at | M18468 | Hs.280342 | PRKAR1A |
| 232010_at | AA129444 | Hs.591707 | FSTL5 |
| 233949_s_at | AI160292 | Hs.414122 | MYH7B |
| 217404_s_at | X16468 | Hs.408182 | COL2A1 |
| 204776_at | NM_003248 | Hs.211426 | THBS4 |
| 213492_at | X06268 | Hs.408182 | COL2A1 |
| 242856_at | AI291804 | | |
| 231935_at | AL133109 | Hs.475902 | ARPP-21 |
| 212092_at | BE858180 | Hs.147492 | PEG10 |
| 235355_at | AL037998 | | |
| 206394_at | NM_004533 | Hs.85937 | MYBPC2 |
| 206373_at | NM_003412 | Hs.598590 | ZIC1 |
| 202688_at | NM_003810 | Hs.478275 | TNFSF10 |
| 205817_at | NM_005982 | Hs.714419 | SIX1 |
| 205163_at | NM_013292 | Hs.50889 | MYLPF |
| 212688_at | BC003393 | Hs.239818 | PIK3CB |
| 201349_at | NM_004252 | Hs.711846 | SLC9A3R1 |
| 235077_at | BF956762 | Hs.525589 | MEG3 |
| 211537_x_at | AF218074 | Hs.714773 | MAP3K7 |
| 207148_x_at | NM_016599 | Hs.381047 | MYOZ2 |
| 218974_at | NM_018013 | Hs.445244 | SOBP |
| 205940_at | NM_002470 | Hs.440895 | MYH3 |
| 205388_at | NM_003279 | Hs.182421 | TNNC2 |
| 219772_s_at | NM_014332 | Hs.86492 | SMPX |
| 206117_at | NM_000366 | Hs.133892 | TPM1 |
| 226913_s_at | BF527050 | Hs.243678 | SOX8 |
| 229374_at | AI758962 | Hs.371218 | EPHA4 |
| 205676_at | NM_000785 | Hs.524528 | CYP27B1 |
| 219894_at | NM_019066 | Hs.141496 | MAGEL2 |
| 211536_x_at | AB009358 | Hs.714773 | MAP3K7 |
| 205736_at | NM_000290 | Hs.632642 | PGAM2 |
| 226554_at | AW445134 | Hs.591384 | ZBTB7A |
| 235927_at | BE350122 | Hs.370770 | XPO1 |
| 212558_at | BF508662 | Hs.436944 | SPRY1 |
| 226856_at | BF793701 | Hs.556077 | MUSTN1 |
| 211793_s_at | AF260261 | Hs.471156 | ABI2 |
| 239537_at | AW589904 | Hs.302341 | ST8SIA2 |
| 205693_at | NM_006757 | Hs.73454 | TNNT3 |
| 222919_at | AA192260 | Hs.654601 | TRDN |
| 209190_s_at | AF051782 | Hs.529451 | DIAPH1 |
| 205577_at | NM_005609 | Hs.154084 | PYGM |
| 220260_at | NM_018317 | Hs.479403 | TBC1D19 |
| 232955_at | AU144397 | Hs.611431 | FLJ41170 |
| 230915_at | AI741629 | Hs.61684 | DHRS7C |
| 231721_at | AF356518 | Hs.150718 | JAM3 |
| 207293_s_at | U16957 | Hs.405348 | AGTR2 |
| 219804_at | NM_024875 | Hs.645273 | SYNPO2L |
| 210794_s_at | AF119863 | Hs.525589 | MEG3 |
| 244839_at | AW975934 | Hs.134602 | TTN |
| 206657_s_at | NM_002478 | Hs.181768 | MYOD1 |
| 227823_at | BE348679 | Hs.512180 | RGAG4 |
| 212094_at | AL582836 | Hs.147492 | PEG10 |
| 202687_s_at | U57059 | Hs.478275 | TNFSF10 |
| 205902_at | AJ251016 | Hs.490765 | KCNN3 |
| 1559965_at | BC037827 | | |
| 1729_at | L41690 | Hs.460996 | TRADD |
| 207066_at | NM_002152 | Hs.436885 | HRC |
| 218824_at | NM_018215 | Hs.8395 | PNMAL1 |
| 205900_at | NM_006121 | Hs.80828 | KRT1 |
| 207324_s_at | NM_004948 | Hs.567260 | DSC1 |
| 206642_at | NM_001942 | Hs.2633 | DSG1 |
| 220664_at | NM_006518 | Hs.2421 | SPRR2C |
| 207356_at | NM_004942 | Hs.105924 | DEFB4 |
| 205724_at | NM_000299 | Hs.497350 | PKP1 |
| 215704_at | AL356504 | Hs.654510 | FLG |
| 237732_at | AI432195 | | |
| 41469_at | L10343 | Hs.112341 | PI3 |
| 230193_at | AI479075 | Hs.709837 | WDR66 |
| 203691_at | NM_002638 | Hs.112341 | PI3 |
| 1553081_at | NM_080869 | Hs.352180 | WFDC12 |
| 239853_at | AI279514 | Hs.298079 | KLC3 |
| 231033_at | AI819863 | | |
| 241813_at | BG252318 | Hs.405610 | MBD1 |
| 205109_s_at | NM_015320 | Hs.469935 | ARHGEF4 |

TABLE 5

200 genes used in conjunction with clinical variables to predict breast cancer recurrence risk status. P-value is testing the hypothesis if the expression data is predictive of survival over and above the clincal variable covariates.

| Affymetrix Probe ID | Gene symbol | Genbank | Entrez Gene ID |
|---|---|---|---|
| 209856_x_at | ABI2 | U31089 | 10152 |
| 202502_at | ACADM | NM_000016 | 34 |
| 210838_s_at | ACVRL1 | L17075 | 94 |
| 205746_s_at | ADAM17 | U86755 | 6868 |
| 206807_s_at | ADD2 | NM_017482 | 119 |

TABLE 5-continued 200 genes used in conjunction with clinical variables to predict breast cancer recurrence risk status. P-value is testing the hypothesis if the expression data is predictive of survival over and above the clincal variable covariates.

| Affymetrix Probe ID | Gene symbol | Genbank | Entrez Gene ID |
|---|---|---|---|
| 212224_at | ALDH1A1 | NM_000689 | 216 |
| 204174_at | ALOX5AP | NM_001629 | 241 |
| 201302_at | ANKA4 | NM_001153 | 307 |
| 205083_at | AOX1 | NM_001159 | 316 |
| 208074_s_at | AP2S1 | NM_021575 | 1175 |
| 202120_x_at | AP2S1 | NM_004069 | 1175 |
| 211047_x_at | AP2S1 | BC006337 | 1175 |
| 203526_s_at | APC | M74088 | 324 |
| 214995_s_at | APOBEC3F | BF508948 | 200316/// 60489 |
| 213702_x_at | ASAH1 | AI934569 | 427 |
| 210980_s_at | ASAH1 | U47674 | 427 |
| 218659at | ASXL2 | NM_018263 | 55252 |
| 212072_at | ATM | U82828 | 472 |
| 217014_s_at | AZGP1 | AC004522 | 563/// 646282 |
| 209311_at | BCL2L2 | D87461 | 599 |
| 209974_s_at | BUB3 | AF047473 | 9184 |
| 218614_at | C12orf35 | NM_018169 | 55196 |
| 221434_s_at | C14orf156 | NM_031210 | 81892 |
| 203830_at | C17orf75 | NM_022344 | 64149 |
| 209006_s_at | C1orf63 | AF247168 | 57035 |
| 219288_at | C3orf14 | NM_020685 | 57415 |
| 220324_at | C6orf155 | NM_024882 | 79940 |
| 219223_at | C9orf7 | NM_017586 | 11094 |
| 207243_s_at | CALM2 | NM_001743 | 805 |
| 214845_s_at | CALU | AF257659 | 813 |
| 200756_x_at | CALU | U67280 | 813 |
| 211922_s_at | CAT | AY028632 | 847 |
| 214710_s_at | CCNB1 | BE407516 | 891 |
| 215784_at | CD1E | AA309511 | 913 |
| 211574_s_at | CD46 | D84105 | 4179 |
| 207319_s_at | CDC2L5 | NM_003718 | 8621 |
| 218592_s_at | CECR5 | NM_017829 | 27440 |
| 40020_at | CELSR3 | AB011536 | 1951 |
| 209508_x_at | CFLAR | AF005774 | 8837 |
| 210564_x_at | CFLAR | AF009619 | 8837 |
| 203975_s_at | CHAF1A | BF000239 | 10036 |
| 204170_s_at | CKS2 | NM_001827 | 1164 |
| 64486_at | CORO1B | AI341234 | 57175 |
| 205538_at | CORO2A | NM_003389 | 7464 |
| 210687_at | CPT1A | BC000185 | 1374 |
| 214513_s_at | CREB1 | M34356 | 1385 |
| 204313_s_at | CREB1 | AA161486 | 1385 |
| 202978_s_at | CREBZF | AW204564 | 58487 |
| 201200_at | CREG1 | NM_003851 | 8304 |
| 218924_s_at | CTBS | NM_004388 | 1486 |
| 205898_at | CX3CR1 | U20350 | 1524 |
| 219969_at | QXorf15 | NM_018360 | 55787 |
| 205417_at | DAG1 | NM_004393 | 1605 |
| 201571_s_at | DCTD | AI656493 | 1635 |
| 219328_at | DDX31 | NM_022779 | 64794 |
| 221509_at | DENR | AB014731 | 8562 |
| 202865_at | DNAJB12 | AI695173 | 54788 |
| 209059_s_at | EDF1 | AB002282 | 8721 |
| 213614_x_at | EEF1A1 | BE786672 | 1915 |
| 222314_x_at | EGO | AW970881 | |
| 208688_x_at | EIF3B | U78525 | 8662 |
| 200005_at | EIF3D | NM_003753 | 8664 |
| 201726_at | ELAVL1 | BC003376 | 1994 |
| 212087_at | ERAL1 | AL562733 | 26284 |
| 204817_at | ESPL1 | NM_012291 | 9700 |
| 213007_at | FANCI | W74442 | 55215 |
| 213008_at | FANCI | BG403615 | 55215 |
| 209456_s_at | FBXW11 | AB033281 | 23291 |
| 204767_s_at | FEN1 | BC000323 | 2237 |
| 208228_s_at | FGFR2 | M87771 | 2263 |
| 203638_s_at | FGFR2 | NM_022969 | 2263 |
| 204236_at | FLI1 | NM_002017 | 2313 |
| 202838_at | FUCA1 | NM_000147 | 2517 |
| 217370_x_at | FUS | S75762 | 2521 |
| 207112_s_at | GAB1 | NM_002039 | 2549 |
| 203725_at | GADD45A | NM_001924 | 1647 |
| 210872_x_at | GAS7 | BC001152 | 8522 |
| 208503_s_at | GATAD1 | NM_021167 | 57798 |
| 219777_at | GIMAP6 | NM_024711 | 474344 |
| 207387_s_at | GK | NM_000167 | 2710 |
| 212241_at | GRINL1A | AI632774 | 145781/// 339970/// 81488 |
| 210981_s_at | GRK6 | AF040751 | 2870 |
| 205436_s_at | H2AFX | NM_002105 | 3014 |
| 221976_s_at | HDGFRP3 | AW207448 | 50810 |
| 206313_at | HLA-DOA | NM_002119 | 3111 |
| 203744_at | HMGB3 | NM_005342 | 3149 |
| 201277_s_at | HNRNPAB | NM_004499 | 3182 |
| 213619_at | HNRNPH1 | AV753392 | 3187 |
| 204785_x_at | IFNAR2 | NM_000874 | 3455 |
| 212196_at | IL6ST | AW242916 | 3572 |
| 208930_s_at | 1LF3 | BG032366 | 3609 |
| 217732_s_at | ITM2B | AF092128 | 9445 |
| 214098_at | KIAA1107 | AB029030 | 23285 |
| 218755_at | KIF20A | NM_005733 | 10112 |
| 209680_s_at | KIFC1 | BC000712 | 3833 |
| 213507_s_at | KPNB1 | BG249565 | 3837 |
| 34031_i_at | KRIT1 | U90269 | 889 |
| 205269_at | LCP2 | AI123251 | 3937 |
| 203713_s_at | LLGL2 | NM_004524 | 3993 |
| 203276_at | LMNB1 | NM_005573 | 4001 |
| 201383_s_at | LOC100133166 | AL044170 | 4077/// 727732 |
| 208633_s_at | MACF1 | W61032 | 23499 |
| 203266_s_at | MAP2K4 | NM_003010 | 6416 |
| 207292_s_at | MAPK7 | NM_002749 | 5598 |
| 208403_x_at | MAX | NM_002382 | 4149 |
| 212023_sat | MKI67 | AU147044 | 4288 |
| 220526_s_at | MRPL20 | NM_017971 | 55052 |
| 212093_s_at | MTUS1 | AI695017 | 57509 |
| 214753_at | N4BP2L2 | AW084068 | 10443 |
| 221242_at | | NM_025051 | |
| 217591_at | | BF725121 | 6498 |
| 205732_s_at | NCOA2 | NM_006540 | 10499 |
| 219961_s_at | NCRNA00153 | NM_018474 | 55857 |
| 203606_at | NDUFS6 | NM_004553 | 4726 |
| 218318_s_at | NLK | NM_016231 | 51701 |
| 209750_at | NR1D2 | N32859 | 9975 |
| 211671_s_at | NR3C1 | U01351 | 2908 |
| 201865_x_at | NR3C1 | AI432196 | 2908 |
| 212181_s_at | NUDT4 | AF191654 | 11163 |
| 218039_at | NUSAP1 | NM_016359 | 51203 |
| 219582_at | OGFRL1 | NM_024576 | 79627 |
| 205233_s_at | PAFAH2 | NM_000437 | 5051 |
| 209431_s_at | PATZ1 | AF254083 | 23598 |
| 211807_x_at | PCDHGB5 | AF152521 | 56101 |
| 212094_at | PEG10 | AL582836 | 23089 |
| 215832_x_at | PICALM | AV722190 | 8301 |
| 203134_at | PICALM | NM_007166 | 8301 |
| 201115_at | POLD2 | NM_006230 | 5425 |
| 217806_s_at | POLDIP2 | NM_015584 | 26073 |
| 209502_at | POLR2H | U37689 | 5437 |
| 218009_s_at | PRC1 | NM_003981 | 9055 |
| 201494_at | PRCP | NM_005040 | 5547 |
| 202545_at | PRKCD | NM_006254 | 5580 |
| 206445_s_at | PRMT1 | NM_001536 | 3276 |
| 211921_x_at | PTMA | AF348514 | 5757 |
| 200772_x_at | PTMA | BF686442 | 5757 |
| 208549_x_at | PTMAP7 | NM_016171 | 441454/// 442347/// 442727 |
| 207419_s_at | RAC2 | NM_002872 | 5880 |
| 222077_s_at | RACGAP1 | AU153848 | 29127 |
| 220338_at | RALGPS2 | NM_018037 | 55103 |
| 200749_at | RAN | BF112006 | 5901 |
| 204188_s_at | RARG | M57707 | 5916 |

TABLE 5-continued 200 genes used in conjunction with clinical variables to predict breast cancer recurrence risk status. P-value is testing the hypothesis if the expression data is predictive of survival over and above the clincal variable covariates.

| Affymetrix Probe ID | Gene symbol | Genbank | Entrez Gene ID |
|---|---|---|---|
| 204178_s_at | RBM14 | NM_006328 | 10432 |
| 200997_at | RBM4 | NM_002896 | 5936 |
| 212398_at | RDX | AI057093 | 5962 |
| 221643_s_at | RERE | AF016005 | 473 |
| 218194_at | REXO2 | NM_015523 | 25996 |
| 204402_at | RHBDD3 | NM_012265 | 25807 |
| 212742_at | RNF115 | AL530462 | 27246 |
| 220985_s_at | RNF170 | NM_030954 | 81790 |
| 200717_x_at | RPL7 | NM_000971 | 6129 |
| 200741_s_at | RPS27 | NM_001030 | 6232 |
| 221523_s_at | RRAGD | AL138717 | 58528 |
| 201459_at | RUVBL2 | NM_006666 | 10856 |
| 202026_at | SDHD | NM_003002 | 6392 |
| 203123_s_at | SLC11A2 | AU154469 | 4891 |
| 207057_at | SLC16A7 | NM_004731 | 9194 |
| 205097_at | SLC26A2 | AI025519 | 1836 |
| 202667_s_at | SLC39A7 | NM_006979 | 7922 |
| 213720_s_at | SMARCA4 | AI831675 | 6597 |
| 208794_s_at | SMARCA4 | D26156 | 6597 |
| 220368_s_at | SMEK1 | NM_017936 | 55671 |
| 210465_s_at | SNAPC3 | U71300 | 6619 |
| 202567_at | SNRPD3 | NM_004175 | 6634 |
| 201416_at | SOX4 | BG528420 | 6659 |
| 206748_s_at | SPAG9 | NM_003971 | 9043 |
| 213441_x_at | SPDEF | AI745526 | 25803 |
| 212526_at | SPG20 | AK002207 | 23111 |
| 205542_at | STEAP1 | NM_012449 | 26872 |
| 212084_at | TEX261 | AV759552 | 113419 |
| 208700_s_at | TKT | L12711 | 7086 |
| 202195_s_at | TMED5 | NM_016040 | 50999 |
| 219674_at | TMEM184C | NM_018241 | 55751 |
| 200847_s_at | TMEM66 | NM_016127 | 51669 |
| 209754_s_at | TMPO | AP113682 | 7112 |
| 201291_s_at | TOP2A | AU159942 | 7153 |
| 214299_at | TOP3A | AI676092 | 7156 |
| 214196_s_at | TPP1 | AA602532 | 1200 |
| 202871_at | TRAF4 | NM_004295 | 9618 |
| 200990_at | TRIM28 | NM_005762 | 10155 |
| 204033_at | TRIP13 | NM_004237 | 9319 |
| 212656_at | TSFM | AF110399 | 10102 |
| 202835_at | TXNL4A | BC001046 | 10907 |
| 200684_s_at | UBE2L3 | AI819709 | 7332 |
| 215533_s_at | UBE4B | AF091093 | 10277 |
| 2015134_s_at | UBL3 | AF044221 | 5412 |
| 212008_at | UBXN4 | N29889 | 23190 |
| 209103_s_at | UFD1L | BC001049 | 7353 |
| 214843_s_at | USP33 | AK022864 | 23032 |
| 211749_s_at | VAMP3 | BC005941 | 9341 |
| 212324_s_at | VPS13D | BF111962 | 55187 |
| 219679_s_at | WAC | NM_018604 | 51322 |
| 208453_s_at | XPNPEP1 | NM_006523 | 7511 |
| 213376_at | ZBTB1 | AI656706 | 22890 |
| 204216_s_at | ZC3H14 | NM_024824 | 79882 |
| 214670_at | ZKSCAN1 | AA653300 | 7586 |
| 210282_at | ZMYM2 | AL136621 | 7750 |
| 213698_at | ZMYM6 | AI805560 | 9204 |
| 219924_s_at | ZMYM6 | NM_007167 | 9204 |
| 207304_at | ZNF45 | NM_003425 | 7596 |

The invention claimed is:

1. A system for classifying a biological test sample, including:
   a database populated with reference expression data, the reference expression data including expression levels of a plurality of molecules in a plurality of reference samples, the molecules including a set of marker molecules that includes any combination of 100 or more of the polynucleotides listed in Table 4, each reference sample having a pre-assigned value for each of one or more clinically significant variables;
   at least one processor; and
   at least one storage medium containing program instructions for execution by said processor, said program instructions causing said processor to execute the steps of:
   accepting input expression data, the input expression data including a test vector of expression levels of the set of marker molecules in the biological test sample; and
   passing the input expression data to one or more analysis programs, the analysis programs including at least one statistical classification program which has been trained to distinguish among said pre-assigned values on the basis of that part of the reference data corresponding to expression levels of the set of marker molecules; and
   assigning one of said pre-assigned values to the test sample for at least one of said clinically significant variables using the statistical classification program,
   wherein the one or more clinically significant variables is selected from the group including disease state, disease prognosis, and treatment response.

2. The system according to claim 1, wherein the database is in communication with a server computer which is interconnected to at least one client computer by a data network, said server computer being configured to accept the input expression data from the client computer.

3. The system according to claim 1, wherein the disease is cancer.

4. The system according to claim 3, wherein the one or more clinically significant variables are organized according to a hierarchy.

5. The system according to claim 4, wherein the levels of the hierarchy are selected from the group consisting of anatomical system, tissue type and tumor subtype.

6. The system according to claim 5, wherein the classification program includes a multi-level classifier which classifies the test sample according to anatomical system, then tissue type, then tumor subtype.

7. The system according to claim 3, wherein the disease is breast cancer.

8. The system according to claim 7, wherein one of the one or more clinically significant variables is risk of recurrence.

9. The system according to claim 8, wherein the marker molecules include the polynucleotides listed in Table 5.

10. The system according to claim 1, wherein the reference expression data are generated using a platform selected from the group including cDNA microarrays, oligonucleotides microarrays, protein microarrays, microRNA (miRNA) arrays, and high-throughput quantitative polymerase chain reaction (qPCR).

11. The system according to claim 10, wherein each molecule is a polynucleotide represented by multiple probes, each probe having a different nucleotide sequence corresponding to part of the polynucleotide.

12. The system according to claim 11, wherein one of said analysis programs includes instructions for summarizing the expression levels of the multiple probes into a single expression level for the polynucleotide.

13. The system according to any one of claims 10 to 12, wherein the input expression data are generated using the same platform as the reference expression data.

14. The system according to claim 1, wherein the statistical classification program selected from the group including k-nearest neighbours (kNN), linear discriminant analysis, principal components analysis, nearest centroid classification and support vector machines.

15. The system according to claim 1, wherein the marker molecules include the polynucleotides listed in Table 5.

* * * * *